US009458161B1

(12) United States Patent
Manning et al.

(10) Patent No.: US 9,458,161 B1
(45) Date of Patent: Oct. 4, 2016

(54) TSPO LIGANDS FOR CANCER IMAGING AND TREATMENT

(71) Applicant: Vanderbilt University, Nashville, TN (US)

(72) Inventors: H. Charles Manning, Nashville, TN (US); Jason R. Buck, Nashville, TN (US); Dewei Tang, Nashville, TN (US)

(73) Assignee: Vanderblit University, Nashville, TN (US)

( * ) Notice: Subject to any disclaimer, the term of this patent is extended or adjusted under 35 U.S.C. 154(b) by 0 days.

(21) Appl. No.: 13/669,437

(22) Filed: Nov. 5, 2012

Related U.S. Application Data

(60) Provisional application No. 61/555,278, filed on Nov. 3, 2011.

(51) Int. Cl.
| | |
|---|---|
| *C07D 487/04* | (2006.01) |
| *A61K 31/519* | (2006.01) |
| *A61K 45/06* | (2006.01) |
| *A61K 51/04* | (2006.01) |
| *G01N 33/92* | (2006.01) |

(52) U.S. Cl.
CPC .......... *C07D 487/04* (2013.01); *A61K 31/519* (2013.01); *A61K 45/06* (2013.01); *A61K 51/0459* (2013.01); *G01N 33/92* (2013.01)

(58) Field of Classification Search
CPC ........................... C07D 487/04; A61K 31/519
USPC ....................................... 544/281; 514/259.3
See application file for complete search history.

(56) References Cited

U.S. PATENT DOCUMENTS

| | | | |
|---|---|---|---|
| 3,278,594 | A | 10/1966 | Sweeny |
| 5,114,944 | A | 5/1992 | Taylor, Jr. et al. |
| 5,399,703 | A | 3/1995 | Yoshimoto et al. |
| 6,380,203 | B1 | 4/2002 | Bilodeau et al. |
| 6,410,561 | B1 | 6/2002 | Shinkai et al. |
| 6,903,094 | B2 | 6/2005 | Shinkai et al. |
| 2002/0061897 | A1 | 5/2002 | Elliott et al. |
| 2003/0055087 | A1 | 3/2003 | Shinkai et al. |
| 2009/0028858 | A1 | 1/2009 | Wang et al. |
| 2009/0069321 | A1 | 3/2009 | Wortmann et al. |
| 2009/0311176 | A1 | 12/2009 | Kassiou et al. |
| 2010/0209345 | A1 | 8/2010 | Katsifis et al. |

FOREIGN PATENT DOCUMENTS

| | | |
|---|---|---|
| JP | 2000-001476 | 1/2007 |
| WO | 2008/022396 | 2/2008 |

OTHER PUBLICATIONS

Selleri et al., 2-Arylpyrazolo[1,5-a]pyrimidin-3-yl Acetamides, Bioorganic & Medicinal Chemistry 9 (2001), pp. 2661-2671.*
Selleri et al., A Novel Selective GABA α1 Receptor Agonist Displaying Sedative and Anxiolytic-like Properties in Rodents, J. Med. Chem. 2005, 48, pp. 6756-6760.*
Tang et al., Microwave-assisted organic synthesis of a high-affinity pyrazolo-pyrimidinyl TSPO ligand, Tetrahedron Letters 51 (2010), pp. 4595-4598.*
Menard et al., Biologic and Therapeutic Role of HER2 in Cancer; 2003, Oncogene 22:6570-6578.
Bange et al., Molecular Targets for Breast Cancer Therapy and Prevention; 2001, Nature Medicine 7:548-552.
Okubo, T., Yoshikawa, R., Chaki, S., Okuyama, S., Nakazato, A. "Design, synthesis and structure-affinity relationships of aryloxyanilide derivatives as novel peripheral benzodiazepine receptor ligands." Bioorganic Medicinal Chemistry 2004, 12(2), 423.
Tang, et al., Synthesis and Structure—Activity Relationships of 5,6,7-Substituted Pyrazolopyrimidines: Discovery of a Novel TSPO PET Ligand for Cancer Imaging; Journal of Medicinal Chemistry; 2013; 56; pp. 3429-3433.
Tang et al., Synthesis and Structure—Activity Relationships of 5,6,7-Substituted Pyrazolopyrimidines: Discovery of a Novel TSPO PET Ligand for Cancer Imaging. J Med Chem. Apr. 25, 2013; 56(8): 3429-3433.

* cited by examiner

*Primary Examiner* — Deepak Rao
(74) *Attorney, Agent, or Firm* — Stites & Harbison PLLC; Richard S. Myers, Jr.

(57) ABSTRACT

Embodiments of the present invention relates to compounds of the following formula:

(I)

as well as compositions, methods of imaging and methods of treating subjects comprising the use of the compound, wherein the variables are defined herein.

17 Claims, 21 Drawing Sheets

US 9,458,161 B1

TSPO LIGANDS FOR CANCER IMAGING AND TREATMENT

PRIOR APPLICATIONS

This application claims benefit of U.S. Patent Application 61/555,278, filed Nov. 3, 2011, the contents of which are incorporated herein by reference in their entirety.

FIELD OF THE INVENTION

Generally, the present invention relates to translocator protein (TSPO) positron emission tomography (PET) imaging ligands and their use as cancer imaging probes.

Other aspects of the present invention include methods of treating cancer, comprising administering a compound of the present invention to a subject in need thereof.

BACKGROUND OF THE INVENTION

Cancer accounts for ~23% of all deaths each year and is the second leading cause of death in the United States. Because of its high mortality and preceding morbidity rates, cancer has a significant social and economic impact upon our society. Given that five-year survival rates drastically plummet with tumor stage at the time of detection, there is a pressing public health need to develop and rigorously validate sensitive and robust non-invasive imaging biomarkers capable of identifying tumors at the earliest possible time and to predict patients likely to respond to therapeutic interventions.

Thus, there is a critical need to develop and rigorously validate quantitative biomarkers capable of interrogating the underlying pathophysiology of tumors, as well as to predict the clinical outcome of therapeutic interventions. Assay of conventional cancer biomarkers typically requires invasive procurement of limited quantities of tumor tissue with attendant risks and sampling errors due to heterogeneity. Furthermore, serial tumor biopsies, as are required to assess treatment response longitudinally, are clinically impractical in many instances. Non-invasive imaging circumvents these limitations and offers potential advantages over traditional biopsy-based procedures. Imaging techniques routinely used in clinical oncology include magnetic resonance imaging (MRI), x-ray computed tomography (CT), ultrasound imaging (US), and PET. Of these, the sensitivity and quantitative nature of PET, coupled with the ability to readily produce biologically active compounds bearing positron emitting isotopes, renders PET one the most attractive techniques for detecting tumors and profiling their genetic and molecular features. Despite this, the number of PET tracers currently available for profiling tumors, and accordingly the diversity of biological questions addressable with PET, is limited. By far the most widely used PET tracer in oncology is [$^{18}$F]FDG, a probe that measures glucose utilization and established tool for cancer diagnosis and staging. However, [$^{18}$F]FDG has important limitations, including modest uptake in some tumors (e.g. prostate) and elevated background uptake in certain normal tissues (e.g. brain). Furthermore, a plethora of metabolic processes affect [$^{18}$F]FDG uptake, highlighting a currently unmet need to explore and validate additional molecular targets for cancer imaging.

Formerly referred to as peripheral benzodiazepine receptor (PBR), TSPO is an 18 kDa high-affinity cholesterol- and drug-binding protein that participates in regulation of numerous cellular processes, including cholesterol metabolism, steroid biosynthesis, proliferation and apoptosis. Elevated TSPO expression is well documented in neuroscience and oncology. To date, many preclinical and human studies have shown that tumors arising in the breast, prostate, oral cavity, colon, liver, and brain can express high levels of TSPO, suggesting a role for this molecule in carcinogenesis. Given the role of TSPO in regulation of proliferation and Bcl-2-mediated apoptosis, it is not surprising that TSPO expression tends to correlate with tumor proliferation and aggressive, invasive tumor behavior. Clinically, TSPO levels predict metastatic potential, disease progression and diminished survival in patients with breast, oral, colorectal, and brain tumors.

Embodiments of the present invention include candidates from aryloxyanilides, pyrazolopyrimidines, indoleacetamides, and indolylglyoxylylamides that exhibit significant improvements over classic TSPO ligands such as the isoquinoline carboxamide, PK 11195. While a few of these ligands have been developed as PET imaging probes for neuroscience applications, they have not been explored in cancer imaging.

Malignant gliomas are the most common primary brain tumor and are characterized by invasive growth and recalcitrance to therapy. Currently, diagnosis and grading of gliomas are based upon the pathology of resected specimens with limitations inherent to sampling errors and heterogeneity. Given these limitations, clinical decisions are routinely guided by imaging. The most common imaging metrics employed to detect and diagnose brain tumors are computed tomography (CT) and magnetic resonance imaging (MRI). These modalities provide little, if any, molecular information attributable to the pathological status of the disease. Furthermore, numerous studies document the inherent difficulty associated with determination of brain tumor extent using CT and/or MRI, particularly with infiltrative disease. Positron emission tomography (PET) imaging using [$^{18}$F]FDG is an important technique for brain tumor detection, however, high glucose uptake in normal brain results in modest tumor-to-background ratios, which can confound delineation of disease margins and subsequent grading. Therefore, there is a considerable need to develop and validate improved molecular imaging techniques suitable for detection and/or molecular profiling of brain tumors.

TSPO is typically localized to the outer mitochondrial membrane. TSPO participates in regulation of numerous cellular processes, including cholesterol metabolism, steroid biosynthesis, cellular proliferation, and apoptosis. In normal tissues, TSPO expression tends to be highest in steroid-producing and mitochondrial-enriched tissues such as skeletal muscle, renal tissue, and myocardium, while tissues such as liver and brain exhibit comparatively modest expression. Elevated TSPO expression is found in numerous disease states, including neuroinflammation and psychiatric disorders such as Alzheimer's and Huntington's diseases, as well as cancers of the breast, prostate, oral cavity, colon, liver, and brain. Elevated TSPO expression has also been linked with disease progression and diminished survival in patients with oral, colorectal, breast, and brain cancer. Additionally, elevated TSPO levels appear to be associated with aggressive, metastatic behavior in breast, colorectal, and prostate cancer. Collectively, these data illuminate TSPO expression as a potentially important prognostic biomarker in oncology and suggest the potential utility of tumor-selective TSPO PET ligands for cancer imaging.

Clinically, two of the most common imaging metrics employed to detect and diagnose brain tumors are computed tomography (CT) and magnetic resonance imaging (MRI).

These modalities provide little, if any, molecular information attributable to the pathological status of the disease. Furthermore, numerous studies document the inherent difficulty associated with visualization of the true extent of brain tumor pathology using CT and/or MRI, particularly with highly infiltrative disease. Positron emission tomography (PET) using [$^{18}$F]FDG is among the most powerful imaging approaches currently available for tumor detection in nearly all organ sites, including the brain. However, high glucose uptake in normal brain results in modest tumor-to-background ratios, which can confound delineation of disease margins and subsequent grading. An alternative and potentially superior approach to [$^{18}$F]FDG PET is L-[methyl-$^{11}$C] methionine ([$^{11}$C]methionine). Though promising, the half-life of $^{11}$C limits the broad implementation of this technique. Therefore, there is a considerable need to develop and validate improved molecular imaging techniques suitable for detection and/or molecular profiling of brain tumors.

Given its elevated expression and correlation with aggressive tumor phenotypes, cellular proliferation, and grade in glioma, imaging TSPO expression in brain tumors has been suggested and explored previously. Almost exclusively, these studies employed the well-known TSPO ligand, (R)—N—[$^3$H/$^{11}$C]methyl-N-(1-methylpropyl)-1-(2-chlorophenyl)-isoquinoline-3-carboxamide), [3H/$^{11}$C](R)-PK 11195, for either autoradiographic methods or PET imaging. These studies highlighted important limitations of PK 11195 as a molecular imaging probe. For example, despite the fact that TSPO expression can be up to 12-fold higher in brain tumors compared to normal brain, [$^{11}$C](R)-PK 11195 uptake was shown to be relatively modest in tumors compared to normal brain tissue (≤2:1 T/N,). The high degree of non-displaceable PK 11195 binding documented in both normal brain and tumors limits the ability of [$^{11}$C](R)-PK 11195 to directly reflect TSPO expression.

SUMMARY OF THE INVENTION

One embodiment of the present invention is novel, high-affinity TSPO ligands suitable as cancer imaging probes. High-throughput parallel synthesis and automated sequential microwave-assisted organic synthesis (MAOS) methodologies developed in our laboratory are applied towards the assembly of focused libraries of novel aryloxyanilides and pyrazolopyrimidines. Candidates are triaged using physical and biochemical assays relevantly applied to TSPO expressed in tumors.

Another embodiment of the present invention is high-throughput methods for labeling TSPO ligands with the positron emitting isotopes, including the isotope fluorine-18. Included in this embodiment is the implementation of high-throughput, microfluidic radiochemical techniques for labeling promising ligands with $^{18}$F. Data utilizing microfluidics demonstrate the feasibility of producing high-specific activity preparations of TSPO ligands in sufficient radiochemical yield and quantity for receptor imaging in rodents. Given the high-throughput nature of this approach, methods of the present invention will drastically accelerate the pace of PET imaging probe development.

Anther embodiment of the present invention is the use of TSPO imaging ligands in vivo. TSPO ligands of the present invention can be used to monitor tumor growth and proliferation quantitatively in vivo. Compounds of the present invention are evaluated and validated using established (C6 glioma) and innovative (human-derived glioma xenografts) preclinical brain tumor models. Quantitative PET imaging data is complemented by coregistered MRI metrics and subsequently correlated with coregistered histological and immunohistochemical sections of imaging-matched tumor specimens. Correlative biology emphasizes markers of tumor proliferation, apoptosis, and TSPO regulatory machinery.

Another embodiment is a method for imaging the presence of cancer in a subject, comprising administering a TSPO ligand of the present invention, or a pharmaceutically acceptable salt thereof or pharmaceutically acceptable derivative thereof.

Another embodiment of the present invention is a method of monitoring the progression of cancer in a subject, comprising administering a TSPO ligand of the present invention, or a pharmaceutically acceptable salt thereof or pharmaceutically acceptable derivative thereof.

Another embodiment of the present invention is a method of determining the likelihood of success of cancer treatment in a subject.

Another embodiment of the present invention is compounds of the following formula:

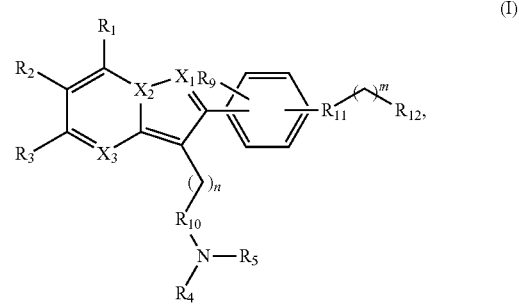

(I)

wherein the variables are defined herein.

Another embodiment of the present invention is compounds of the following formula:

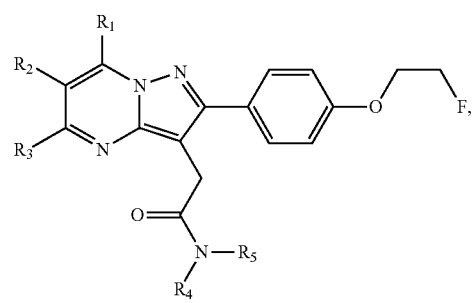

wherein the variables are defined herein.

Another embodiment of the present invention is compounds of the following formula:

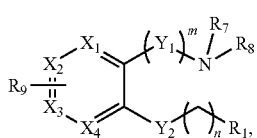

(II)

wherein the variables are defined herein.

Another embodiment of the present invention is a pyrazolopyrimidine compound of the following formula (I):

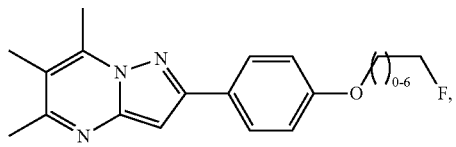

wherein the variables are defined herein.

Another embodiment of the present invention is a method of imaging translocator protein (18 kDa) (TSPO) in a subject, comprising administering to the subject a compound of formula (I) radiolabelled with a radioisotope selected from $^{18}F$, $^{123}I$, $^{76}Br$, $^{124}I$ and $^{75}B$, or a pharmaceutically acceptable salt thereof, and obtaining an image of the location of the radioisotope in the subject.

Another embodiment of the present invention is a pharmaceutical composition comprising a compound of formula (I) or a pharmaceutically acceptable salt thereof, and a pharmaceutically acceptable carrier.

Another embodiment of the present invent is an aryloxyanilide compound of the following:

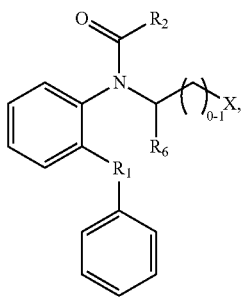

wherein the variables are defined herein.

Another embodiment of the present invention is a method of imaging translocator protein (18 kDa) (TSPO) in a subject, comprising administering to the subject a compound of formula (II) radiolabelled with a radioisotope selected from $^{18}F$, $^{123}I$, $^{76}Br$, $^{124}I$ and $^{75}B$, or a pharmaceutically acceptable salt thereof, and obtaining an image of the location of the radioisotope in the subject.

Another embodiment of the present invention is a method of imaging translocator protein (18 kDa) (TSPO) in a subject, comprising administering to the subject a compound of the present invention radiolabelled with a radioisotope selected from $^{18}F$, $^{123}I$, $^{76}Br$, $^{124}I$ and $^{75}B$, or a pharmaceutically acceptable salt thereof, and obtaining an image of the location of the radioisotope in the subject.

Another embodiment of the present invention is a pharmaceutical composition comprising a compound of the present invention or a pharmaceutically acceptable salt thereof, and a pharmaceutically acceptable carrier.

When mentioning compounds herein, it is assumed that includes pharmaceutically acceptable isotopically-labeled derivatives of the compound. That is, for example, embodiments of the present invention include pharmaceutically acceptable isotopically-labeled/radiolabelled compounds of the present invention. Examples of radiolabeled compounds of the present invention include those listed above, such as ones radiolabeled with $^{18}F$, $^{123}I$, $^{76}Br$, $^{124}I$ and $^{75}B$.

Other embodiments of the present invention include methods for the treatment of disease states associated with expression of TSPO.

Other embodiments of the present invention include methods for the treatment of disease states associated with expression of TSPO comprising the step of co-administering to the mammal at least one compound in a dosage and amount effective to treat the disease state in the animal.

DESCRIPTION OF THE INVENTION

Figure 1:
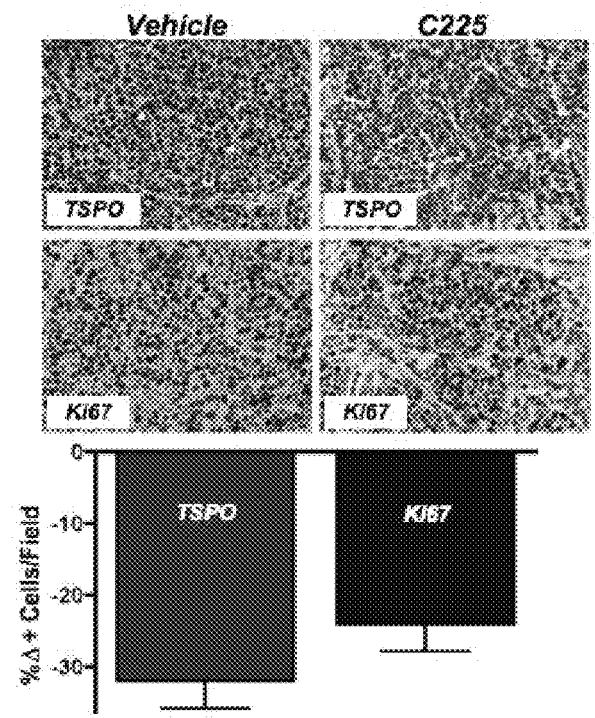
FIG. 1 shows that TSPO levels can predict treatment response. TSPO expression and Ki67 (proliferation) are significantly reduced in responsive human CRC xenografts (DiFi, WT KRAS) after a single therapeutic dose of mAb-C225.

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "combination" or "combinatorial" therapy or treatment, as used herein means the administration of at least two different therapeutics to treat a disorder, condition or symptom, e.g., a cancer condition. Such combination therapy may involve the administration of one therapeutic before, during, and/or after the administration of the other therapeutic. The administrations of the therapeutics may be separated in time by up to several weeks, but more commonly within 48 hours, and most commonly within 24 hours.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$R_1$," "$R_2$," "$R_3$," and "$R_4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups. One example is polyethylene glycol (PEG). Additionally, the —OA$^1$ group may be bonded to a second alkyl group (encompassing ether groups in the definition of alkoxy).

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by a formula —C(O)H. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by a formula —C(O)OH.

The term "ester" as used herein is represented by a formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by a formula -($A^1$O(O)C-$A^2$-C(O)O)$_a$— or -($A^1$O(O)C-$A^2$-OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by a formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by a formula -($A^1$O-$A^2$O)$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole,thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by a formula —OH.

The term "ketone" as used herein is represented by a formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by a formula —$N_3$.

The term "nitro" as used herein is represented by a formula —$NO_2$.

The term "nitrile" as used herein is represented by a formula —CN.

The term "sulfo-oxo" as used herein is represented by a formulas —S(O)$A^1$, —S(O)$_2A^1$, —OS(O)$_2A^1$, or —OS(O)$_2$O$A^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by a formula —S(O)$_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by a formula A'S(O)$_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by a formula A'S(O)$A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by a formula —SH.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Embodiments of the present invention include compounds of the following formula:

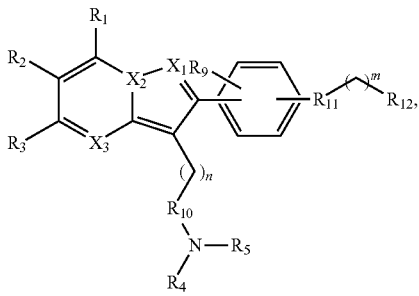

wherein:

$X_1$ is independently C, N, O, or S;

$R_1$ is H, halogen, $CF_3$, $C_1$-$C_8$ alkyl, $C_1$-$C_6$ alkoxy, CO—($C_1$-$C_6$ alkyl), C—O—($C_1$-$C_6$ alkyl), $C_3$-$C_{10}$ cycloalkyl, C—O—($C_3$-$C_{10}$ cycloalkyl); aryl optionally substituted with one or more $R_6$, heteroaryl optionally substituted with one or more $R_6$, or may optionally cyclize with $R_2$ to form a $C_{3-10}$ member ring containing C, O, S or N, optionally substituted with one or more $R_9$;

$R_2$ is H, halogen, $CF_3$, $C_1$-$C_8$ alkyl, $C_1$-$C_6$ alkoxy, CO—($C_1$-$C_6$ alkyl), C—O—($C_1$-$C_6$ alkyl), $C_3$-$C_{10}$ cycloalkyl, C—O—($C_3$-$C_{10}$ cycloalkyl); aryl optionally substituted with one or more $R_6$, heteroaryl optionally substituted with one or more $R_6$, or may optionally cyclize with $R_2$ to form a $C_{3-10}$ member ring containing C, O, S or N, optionally substituted with one or more $R_9$;

$R_3$ is H, halogen, $CF_3$, $C_1$-$C_8$ alkyl, $C_1$-$C_6$ alkoxy, CO—($C_1$-$C_6$ alkyl), C—O—($C_1$-$C_6$ alkyl), $C_3$-$C_{10}$ cycloalkyl, C—O—($C_3$-$C_{10}$ cycloalkyl); aryl optionally substituted with one or more $R_6$, heteroaryl optionally substituted with one or more $R_6$, or may optionally cyclize with $R_2$ to form a $C_{3-10}$ member ring containing C, O, S or N, optionally substituted with one or more $R_9$;

$R_4$ is H, halogen, $CF_3$, $C_1$-$C_8$ alkyl, $C_1$-$C_6$ alkoxy, CO—($C_1$-$C_6$ alkyl), C—O—($C_1$-$C_6$ alkyl), $C_3$-$C_{10}$ cycloalkyl, C—O—($C_3$-$C_{10}$ cycloalkyl); aryl optionally substituted with one or more $R_6$, heteroaryl optionally substituted with one or more $R_6$, or may optionally cyclize with $R_5$ to form a $C_{3-10}$ member ring containing C, O, S or N, optionally substituted with one or more $R_9$;

$R_5$ is H, halogen, $CF_3$, $C_1$-$C_8$ alkyl, $C_1$-$C_6$ alkoxy, CO—($C_1$-$C_6$ alkyl), C—O—($C_1$-$C_6$ alkyl), $C_3$-$C_{10}$ cycloalkyl, C—O—($C_3$-$C_{10}$ cycloalkyl); aryl optionally substituted with one or more $R_6$, heteroaryl optionally substituted with one or more $R_6$, or may optionally cyclize with $R_4$ to form a $C_{3-10}$ member ring containing C, O, S or N, optionally substituted with one or more $R_9$;

$R_9$ is selected from H, OH, $NR_1R_2$, halogen, $C_{1-8}$ alkyl, $C_{3-10}$ cycloalkyl, $OC_{1-6}$ alkyl, $CF_3$, CO—($C_1$-$C_6$ alkyl), C—O—($C_1$-$C_6$ alkyl), C—O—($C_3$-$C_{10}$ cycloalkyl);

$R_{10}$ is selected from $C_1$-$C_6$ alkyl, CO, O, S, $SO_2$, SO, and N;

$R_{11}$ is selected from $C_1$-$C_6$ alkyl, CO, O, S, SO, $SO_2$, N, C;

$R_{12}$ is selected from F, H, OH, $NR_1R_2$, halogen, $C_{1-8}$ alkyl, $C_{3-10}$ cycloalkyl, $OC_{1-6}$ alkyl, $CF_3$, CO—($C_1$-$C_6$ alkyl), C—O—($C_1$-$C_6$ alkyl), C—O—($C_3$-$C_{10}$ cycloalkyl), CN;

m is 0-10;

n is 0-10;

or a pharmaceutically acceptable salt thereof, or a pharmaceutically acceptable derivative thereof.

In other embodiments, each $X_1$ cannot be N when $R_1$ is $CH_3$, $R_2$ is H, $R_3$ is $CH_3$, $R_4$ and $R_5$ are both ethyl, and $R_{ii}$ is O.

Other embodiments of the preset invention include compounds of formula (I), of the following formula:

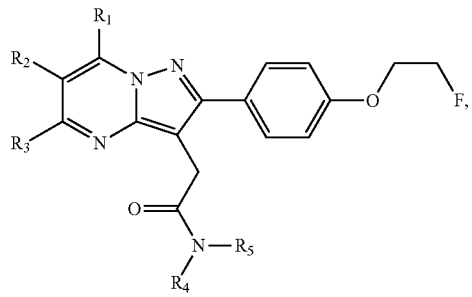

wherein:

$R_1$ is H, halogen, $CF_3$, $C_1$-$C_6$ alkyl, $C_1$-$C_6$ alkoxy, C—O—($C_1$-$C_6$ alkyl), $C_3$-$C_{10}$ cycloalkyl, C—O—($C_3$-$C_{10}$ cycloalkyl); aryl optionally substituted with one or more $R_6$, heteroaryl optionally substituted with one or more $R_6$, or may optionally cyclize with $R_2$ and/or $R_3$ to form a $C_{3-10}$ member ring containing C, O, S or N, optionally substituted with one or more $R_9$;

$R_2$ is H, halogen, $CF_3$, $C_1$-$C_6$ alkyl, $C_1$-$C_6$ alkoxy, C—O—($C_1$-$C_6$ alkyl), $C_3$-$C_{10}$ cycloalkyl, C—O—($C_3$-$C_{10}$ cycloalkyl); aryl optionally substituted with one or more $R_6$, heteroaryl optionally substituted with one or more $R_6$, or may optionally cyclize with $R_2$ and/or $R_3$ to form a $C_{3-10}$ member ring containing C, O, S or N, optionally substituted with one or more $R_9$;

$R_3$ is H, halogen, $CF_3$, $C_1$-$C_6$ alkyl, $C_1$-$C_6$ alkoxy, C—O—($C_1$-$C_6$ alkyl), $C_3$-$C_{10}$ cycloalkyl, C—O—($C_3$-$C_{10}$ cycloalkyl); aryl optionally substituted with one or more $R_6$, heteroaryl optionally substituted with one or more $R_6$, or may optionally cyclize with $R_2$ and/or $R_3$ to form a $C_{3-10}$ member ring containing C, O, S or N, optionally substituted with one or more $R_9$;

$R_4$ is H, halogen, $CF_3$, $C_1$-$C_6$ alkyl, $C_1$-$C_6$ alkoxy, C—O—($C_1$-$C_6$ alkyl), $C_3$-$C_{10}$ cycloalkyl, C—O—($C_3$-$C_{10}$ cycloalkyl); aryl optionally substituted with one or more $R_6$, heteroaryl optionally substituted with one or more $R_6$, or may optionally cyclize with $R_2$ and/or $R_3$ to form a $C_{3-10}$ member ring containing C, O, S or N, optionally substituted with one or more $R_9$;

$R_5$ is H, halogen, $CF_3$, $C_1$-$C_6$ alkyl, $C_1$-$C_6$ alkoxy, C—O—($C_1$-$C_6$ alkyl), $C_3$-$C_{10}$ cycloalkyl, C—O—($C_3$-$C_{10}$ cycloalkyl); aryl optionally substituted with one or more $R_6$, heteroaryl optionally substituted with one or more $R_6$, or may optionally cyclize with $R_2$ and/or $R_3$ to form a $C_{3-10}$ member ring containing C, O, S or N, optionally substituted with one or more $R_9$;

$R_9$ is selected from: H, OH, $NR_1R_2$, halogen, $C_1$-6 alkyl, $C_{3-10}$ cycloalkyl, $OC_1$-6 alkyl, $CF_3$, C—O—($C_1$-$C_6$ alkyl), C—O—($C_3$-$C_{10}$ cycloalkyl);

or a pharmaceutically acceptable salt thereof, or a pharmaceutically acceptable derivative thereof;

provided that when $R_1$ and $R_3$ are $CH_3$, both $R_4$ and $R_5$ are not ethyl.

Other embodiments of the present invention include compounds of formula (I), wherein $R_1$ and $R_3$ are independently $CF_3$, or $C_1$-$C_6$ alkyl, aryl or heteroaryl.

Other embodiments of the present invention include compounds of formula (I), wherein $R_1$ and $R_3$ are independently thiophene, benzene, furan, pyridine, pyrrole, oxazole, or pyrimidine.

Other embodiments of the present invention include compounds of formula (I), wherein $R_2$ is H, alkyl, halogen.

Other embodiments of the present invention include compounds of formula (I), wherein $R_4$ and $R_5$ are independently H, alkyl, aryl, C—O—($C_3$-$C_{10}$ cycloalkyl).

Embodiments of the present invention also include compounds of the following formula:

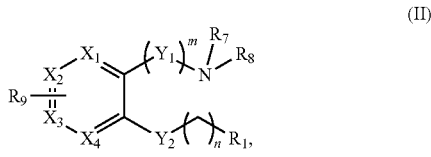

(II)

wherein $X_1$, $X_2$, $X_3$, $X_4$ are independently C, N, O, or S;

$R_1$ is H, halogen, $CF_3$, $C_1$-$C_8$ alkyl, $C_1$-$C_6$ alkoxy, CO—($C_1$-$C_6$ alkyl), C—O—($C_1$-$C_6$ alkyl), $C_3$-$C_{10}$ cycloalkyl, C—O—($C_3$-$C_{10}$ cycloalkyl); aryl optionally substituted with one or more $R_9$, heteroaryl optionally substituted with one or more $R_9$;

$R_7$ is H, halogen, $CF_3$, $C_1$-$C_8$ alkyl, $C_1$-$C_6$ alkoxy, CO—($C_1$-$C_6$ alkyl), C—O—($C_1$-$C_6$ alkyl), $C_3$-$C_{10}$ cycloalkyl, C—O—($C_3$-$C_{10}$ cycloalkyl), aryl optionally substituted with one or more $R_9$, heteroaryl optionally substituted with one or more $R_9$, CO—$R_3$, or may optionally cyclize with $R_8$ to form a $C_{3-10}$ member ring containing C, O, S or N, optionally substituted with one or more $R_9$;

$R_8$ is H, halogen, $CF_3$, $C_1$-$C_8$ alkyl, $C_1$-$C_6$ alkoxy, CO—($C_1$-$C_6$ alkyl), C—O—($C_1$-$C_6$ alkyl), $C_3$-$C_{10}$ cycloalkyl, C—O—($C_3$-$C_{10}$ cycloalkyl), aryl optionally substituted with one or more $R_9$, heteroaryl optionally substituted with one or more $R_9$, $Y_3$—$R_2$, or may optionally cyclize with $R_7$ to form a $C_{3-10}$ member ring containing C, O, S or N, optionally substituted with one or more $R_9$ $Y_1$ is alkyl, O, S, NH;
$Y_2$ is alkyl, O, S, NH;
$Y_3$ is alkyl, O, S, NH;

$R_2$ is H, halogen, $CF_3$, $C_1$-$C_8$ alkyl, $C_1$-$C_6$ alkoxy, CO—($C_1$-$C_6$ alkyl), C—O—($C_1$-$C_6$ alkyl), $C_3$-$C_{10}$ cycloalkyl, C—O—($C_3$-$C_{10}$ cycloalkyl); aryl optionally substituted with one or more $R_9$, heteroaryl optionally substituted with one or more $R_9$;

$R_3$ is H, halogen, $CF_3$, fluoroalkyl, $C_1$-$C_6$ alkyl, $C_1$-$C_6$ alkoxy, CO—($C_1$-$C_6$ alkyl), C—O—($C_1$-$C_6$ alkyl), $C_3$-$C_{10}$ cycloalkyl, C—O—($C_3$-$C_{10}$ cycloalkyl); aryl optionally substituted with one or more $R_9$, heteroaryl optionally substituted with one or more $R_9$;

$R_9$ is selected from: H, OH, $NR_1R_2$, halogen, $C_{1-6}$ alkyl, $C_{3-10}$ cycloalkyl, $OC_{1-6}$ alkyl, $CF_3$, CO—($C_1$-$C_6$ alkyl), C—O—($C_1$-$C_6$ alkyl), $C_3$-$C_{10}$ cycloalkyl;

m is 0-10;
n is 0-10;

or a pharmaceutically acceptable salt thereof, or a pharmaceutically acceptable derivative thereof.

In other embodiments, when $Y_2$ is O, n is 0, $R_1$ is phenyl, $R_7$ is $COCH_3$, $Y_3$ is C, $X_3$ is C or N, then $R_2$ is not chosen from:

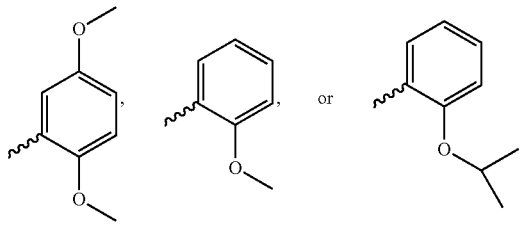

Other embodiments of the present invention include compounds of formula (II), wherein

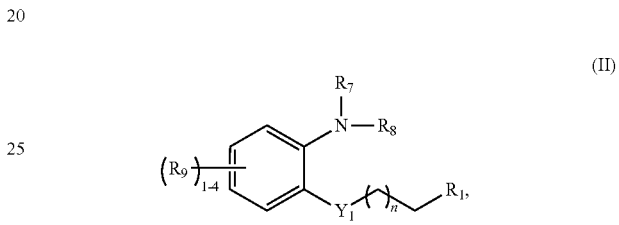

(II)

wherein $R_1$ is H, halogen, $CF_3$, $C_1$-$C_6$ alkyl, $C_1$-$C_6$ alkoxy, C—O—($C_1$-$C_6$ alkyl), $C_3$-$C_{10}$ cycloalkyl, C—O—($C_3$-$C_{10}$ cycloalkyl); aryl optionally substituted with one or more $R_9$, heteroaryl optionally substituted with one or more $R_9$;

$R_7$ is H, halogen, $CF_3$, $C_1$-$C_6$ alkyl, $C_1$-$C_6$ alkoxy, C—O—($C_1$-$C_6$ alkyl), $C_3$-$C_{10}$ cycloalkyl, C—O—($C_3$-$C_{10}$ cycloalkyl); aryl optionally substituted with one or more $R_9$, heteroaryl optionally substituted with one or more $R_9$, C—O—$R_3$, $R_8$ is H, halogen, $CF_3$, $C_1$-$C_6$ alkyl, $C_1$-$C_6$ alkoxy, C—O—($C_1$-$C_6$ alkyl), $C_3$-$C_{10}$ cycloalkyl, C—O—($C_3$-$C_{10}$ cycloalkyl); aryl optionally substituted with one or more $R_9$, heteroaryl optionally substituted with one or more $R_9$, $Y_2$—$R_2$;

$Y_1$ is alkyl, O, S, NH;
$Y_2$ is alkyl, O, S, NH;

$R_2$ is H, halogen, $CF_3$, $C_1$-$C_6$ alkyl, $C_1$-$C_6$ alkoxy, C—O—($C_1$-$C_6$ alkyl), $C_3$-$C_{10}$ cycloalkyl, C—O—($C_3$-$C_{10}$ cycloalkyl); aryl optionally substituted with one or more $R_9$, heteroaryl optionally substituted with one or more $R_9$;

$R_3$ is H, halogen, $CF_3$, fluoroalkyl, $C_1$-$C_6$ alkyl, $C_1$-$C_6$ alkoxy, C—O—($C_1$-$C_6$ alkyl), $C_3$-$C_{10}$ cycloalkyl, C—O—($C_3$-$C_{10}$ cycloalkyl); aryl optionally substituted with one or more $R_9$, heteroaryl optionally substituted with one or more $R_9$;

$R_9$ is independently selected from: H, OH, $NR_1R_2$, halogen, $C_{1-6}$ alkyl, $C_{3-10}$ cycloalkyl, $OC_{1-6}$ alkyl, $CF_3$, C—O—($C_1$-$C_6$ alkyl), $C_3$-$C_{10}$ cycloalkyl;

or a pharmaceutically acceptable salt thereof, or a pharmaceutically acceptable derivative thereof.

Other embodiments of the present invention include compounds of formula (II), wherein $R_7$ and $R_8$ are H.

Other embodiments of the present invention include compounds of formula (II), wherein $R_7$ is CO—$R_3$. In other embodiments, $R_3$ is fluoroalkyl.

Other embodiments of the present invention include compounds of formula (II), wherein $R_7$ is CO—$R_3$, and $R_8$ is Y$_2$—R$_2$. In other embodiments, Y$_2$ is alkyl and R$_2$ is alkyl, aryl optionally substituted with at least one R$_9$, heteroaryl optionally substituted with at least one R$_9$, or cycloalkyl.

In other embodiments, R$_2$ is alkyl, cyclopropane, cyclobutane, cyclopentane, cyclyhexane, benzene, benzene substituted with R$_9$, pyridine, pyridine substituted with R$_9$, pyrrole, oxazole, or pyrimidine.

Other embodiments include compounds of the following formula:

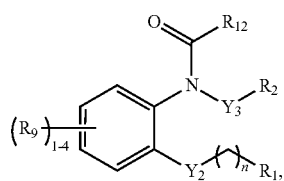

wherein:
R$_1$ is optionally substituted phenyl, optionally substituted alkyl;
R$_2$ is optionally substituted phenyl, optionally substituted alkyl;
R$_{12}$ is optionally substituted alkyl;
R$_9$ is independently selected from: H, OH, NR$_1$R$_2$, halogen, C$_{1-6}$ alkyl, C$_{3-10}$ cycloalkyl, OC$_{1-6}$ alkyl, CF$_3$, C—O—(C$_1$-C$_6$ alkyl), C$_3$-C$_{10}$ cycloalkyl;
Y$_2$ is O, S;
Y$_3$ is (—CH$_2$—)$_{0-10}$;
n is 0-10.

In other embodiments, R$_{12}$ is not —CH$_2$F when Y$_3$ is —CH$_2$—, R$_2$ is 2,4-methoxyphenyl, Y$_2$ is O, n is 0, and R$_1$ is phenyl.

In other embodiments, R$_3$ is substituted with at least one heterocycle.

In other embodiments, the heterocycle is morpholine, piperidine, pyrrolidine.

Other embodiments of the present invention are compounds of the following formula:

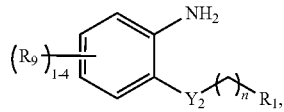

wherein:
R$_1$ is aryl, heteroaryl;
R$_9$ is H, halogen, alkyl, alkoxy, —CO-alkyl;
Y$_2$ is O, S, NH;
n is 0-10.

Embodiments of the present invention include pyrazolopyrimidine compounds of the following formula (I):

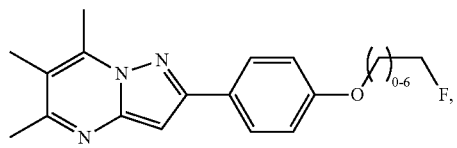

wherein
R$_1$ is CH$_3$, CH(CH$_3$)$_2$, C(CH$_3$)$_3$, phenyl (substituted or unsubstituted), CF$_3$, CF$_2$CF$_2$CF$_3$, CH$_2$CH$_3$;
R$_2$ is CH$_3$, CH(CH$_3$)$_2$, C(CH$_3$)$_3$, phenyl (substituted or unsubstituted), CF$_3$, CF$_2$CF$_2$CF$_3$, CH$_2$CH$_3$; and
R$_3$ is H, CH$_3$, Cl.

Other embodiments of the present invention include the following compounds:

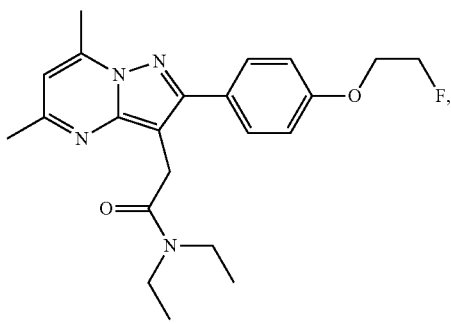

DPA-714

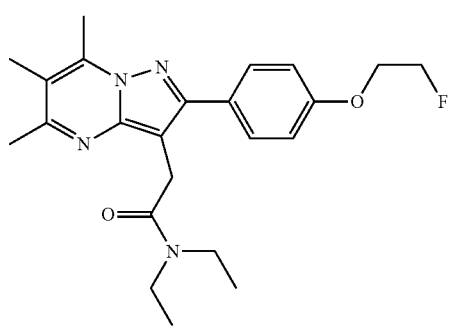

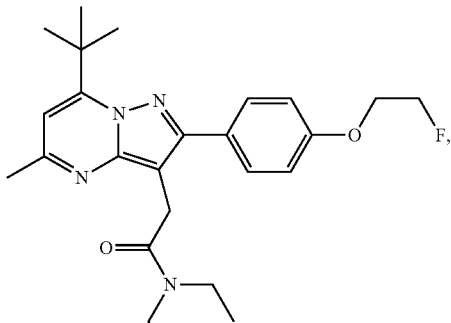

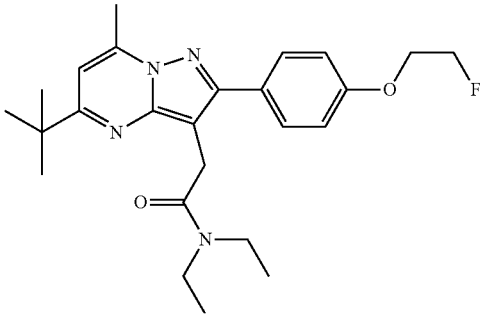

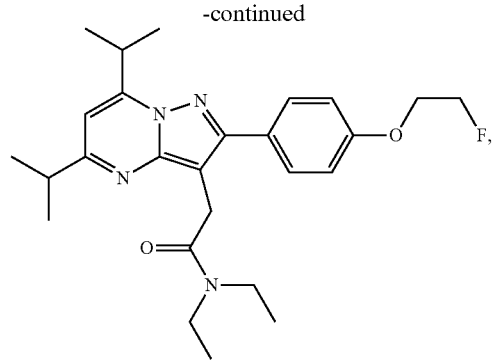
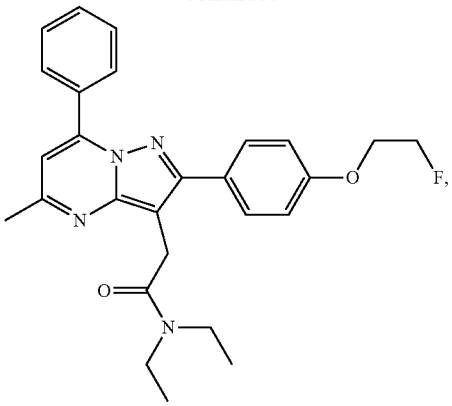

25
-continued
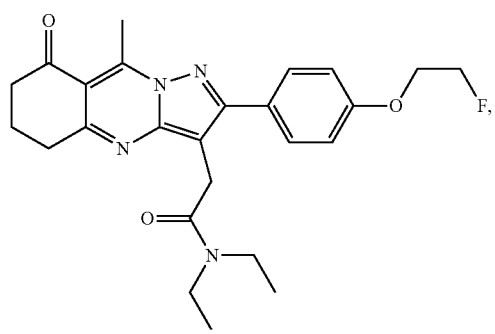
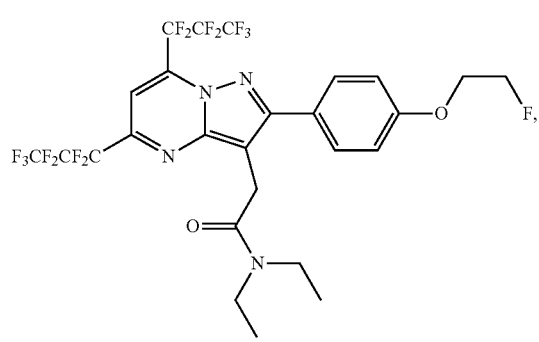
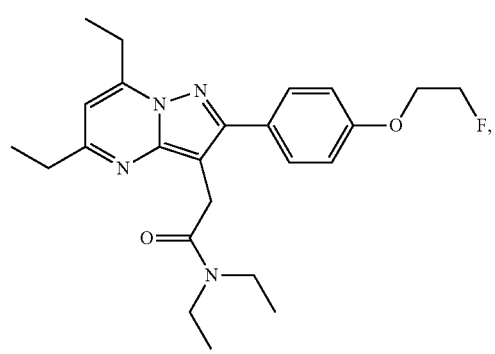
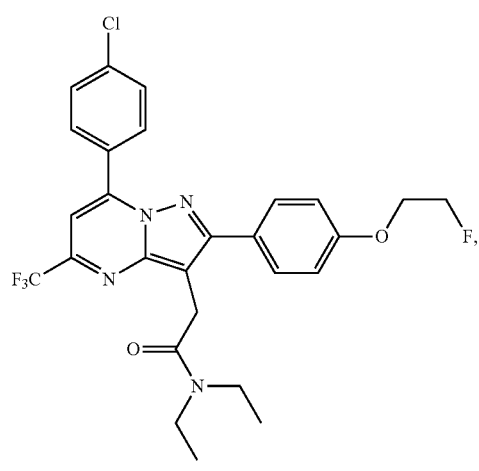
26
-continued
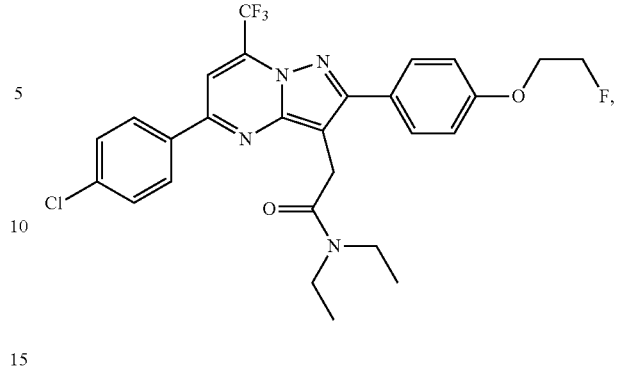
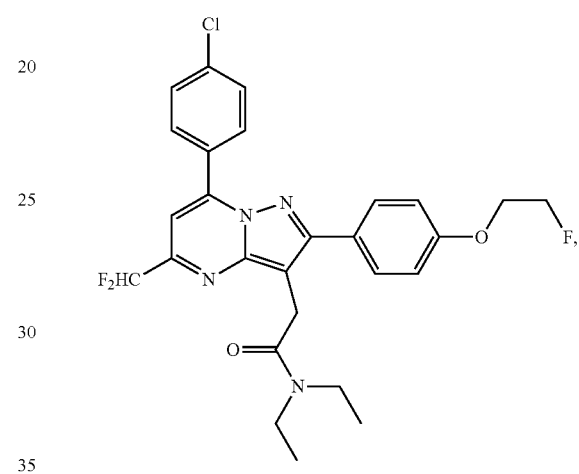
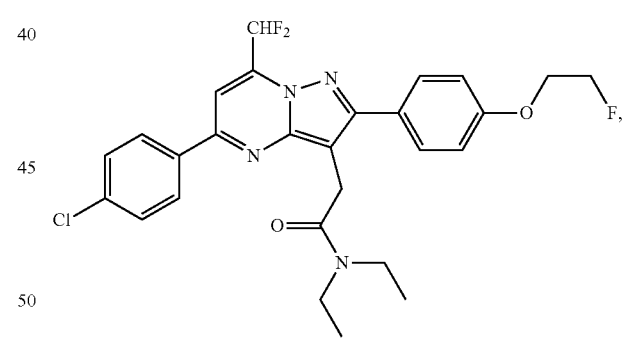
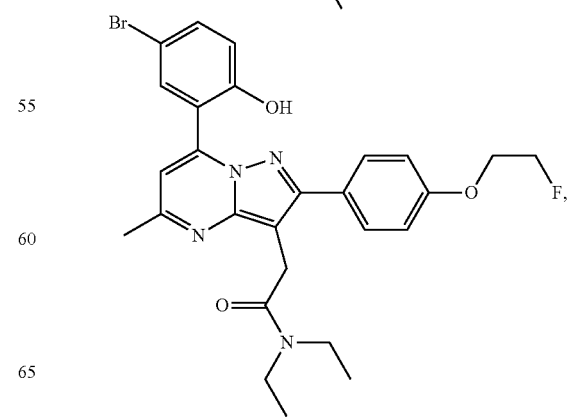

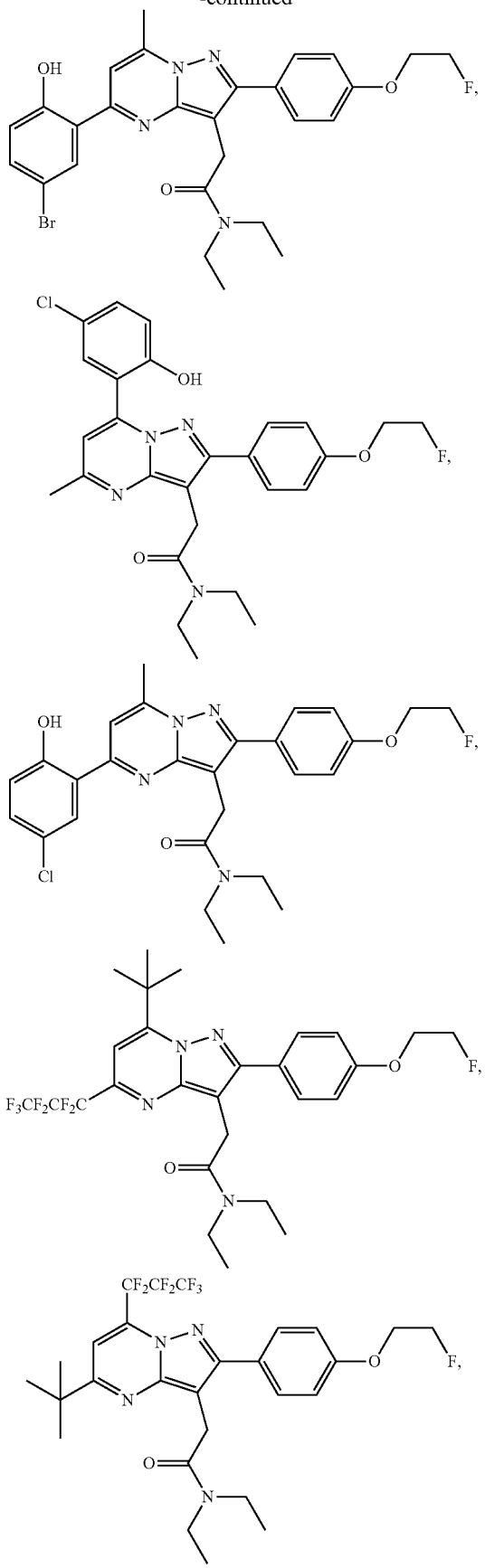
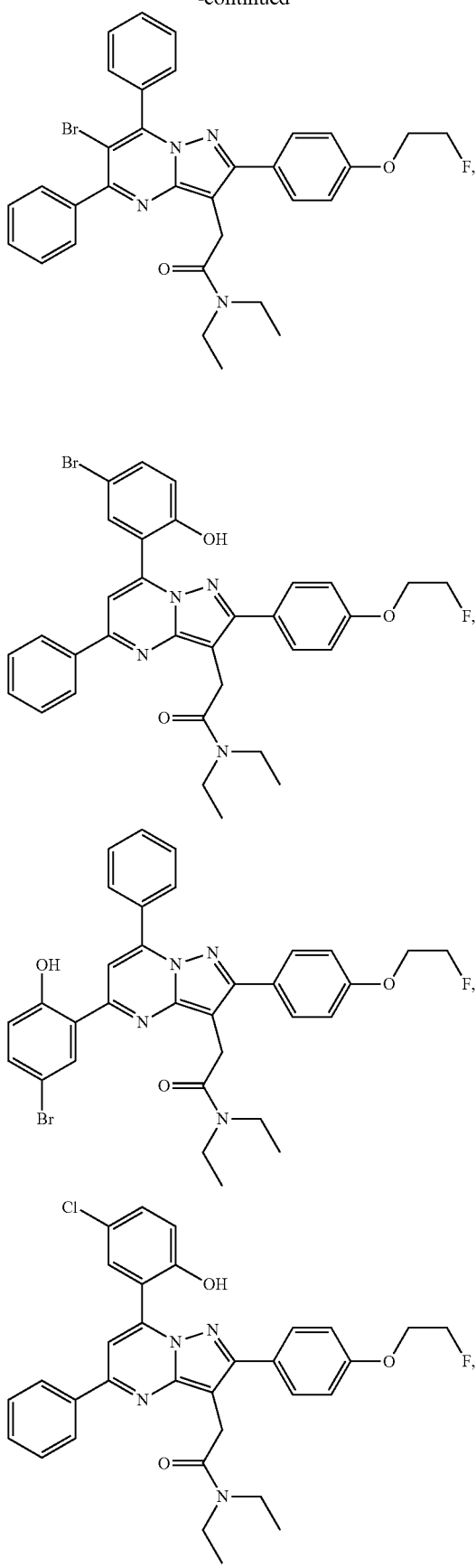

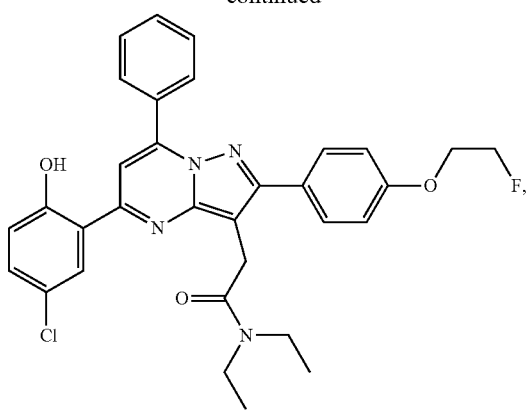
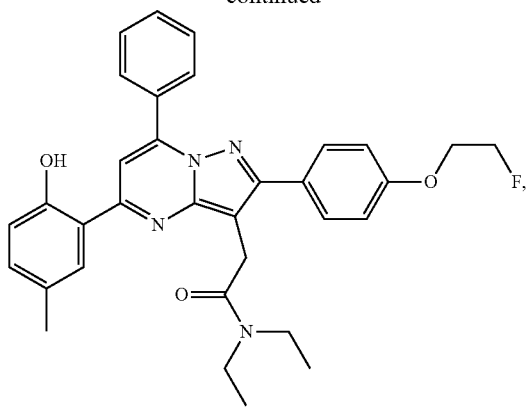
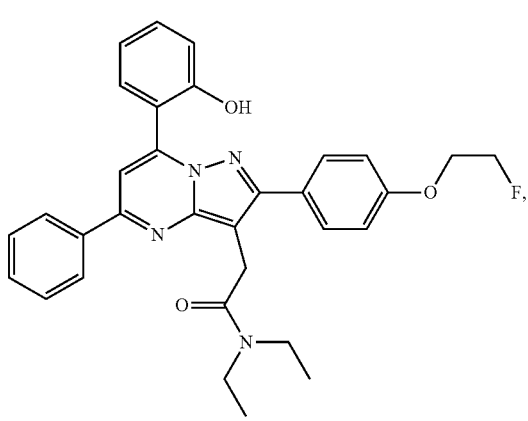
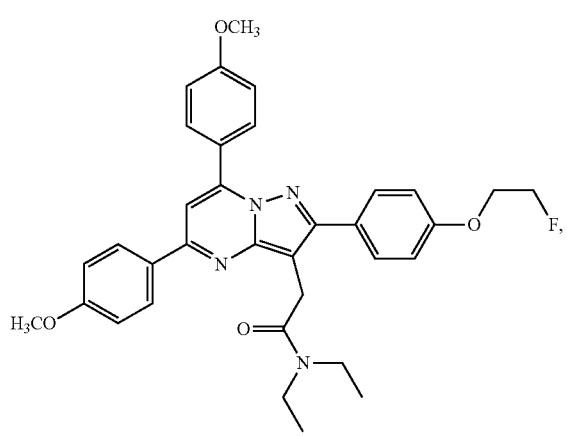
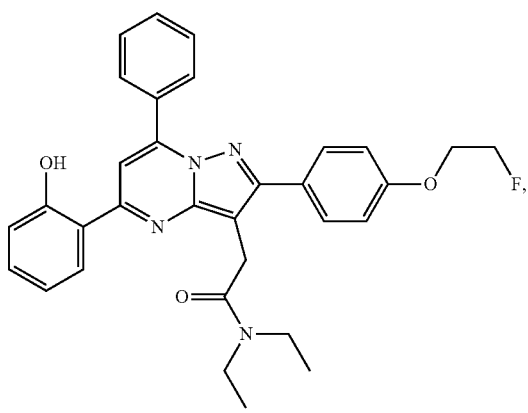
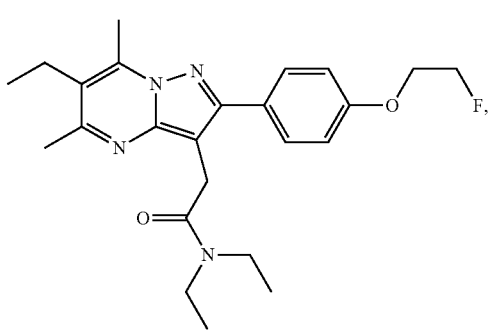
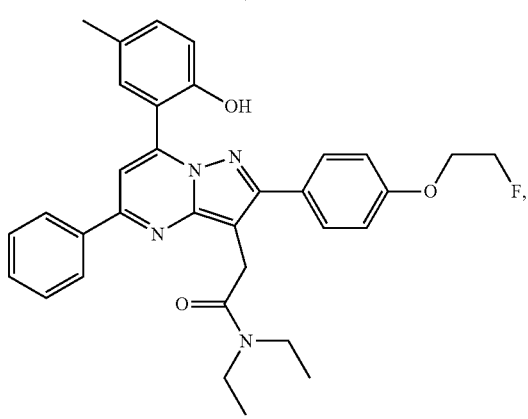
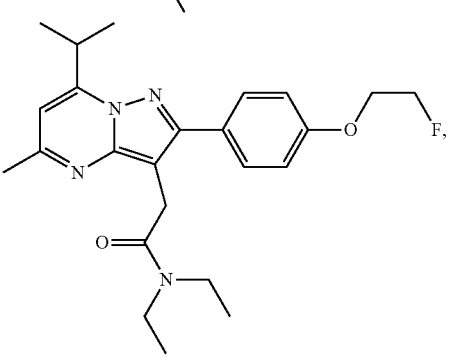

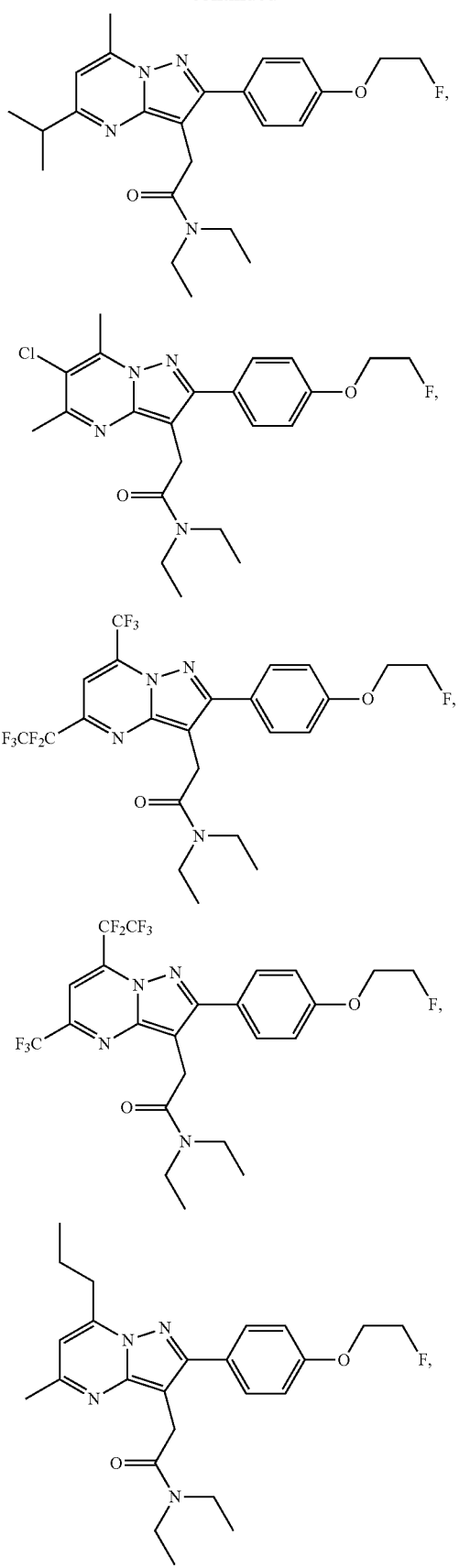
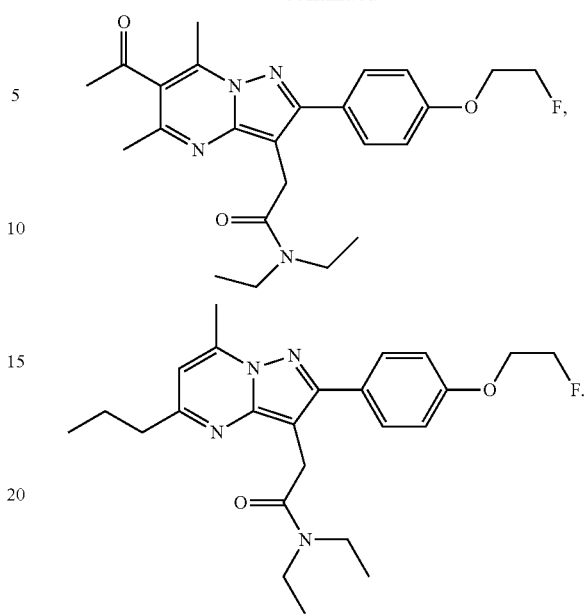
Another embodiment of the present invent is an aryloxyanilide compound of the following formula:
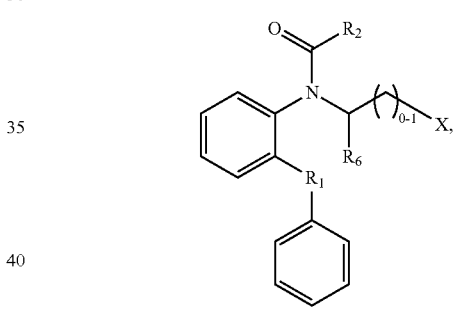
wherein
$R_1$ is O, $CH_2$, S;
$R_2$ is H, F, Br;
$R_3$ is H, $OCH_3$;
$R_4$ is H, F, $C(CH_3)$, Br, Cl, $CH(CH_3)_2$, $NO_2$;
$R_5$ is H, $OCH_3$;
$R_6$ is H, $OCH_3$;
X is chosen from
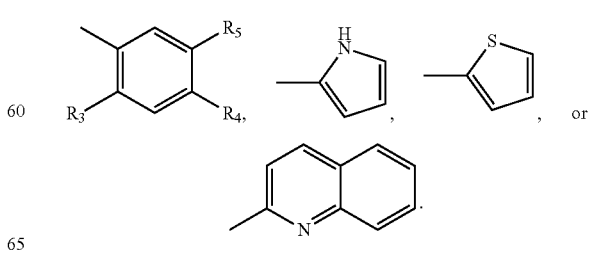

Other embodiments of the present invention include the following compounds:
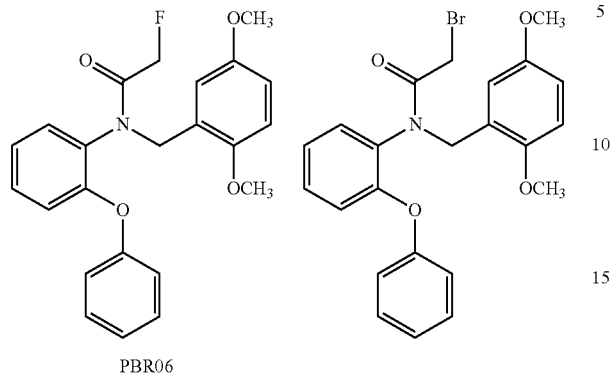
PBR06
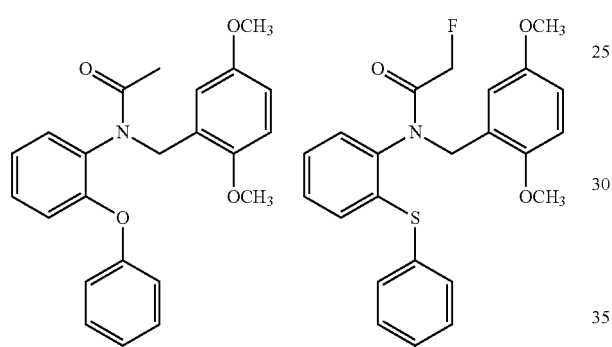
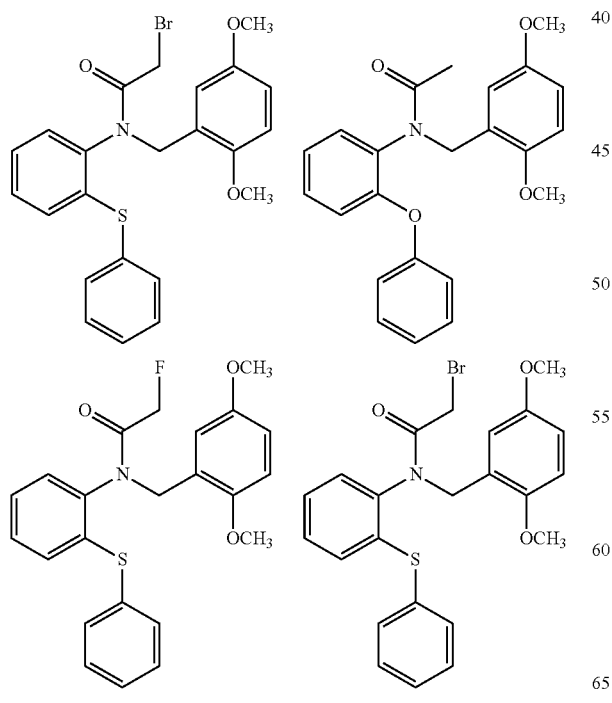
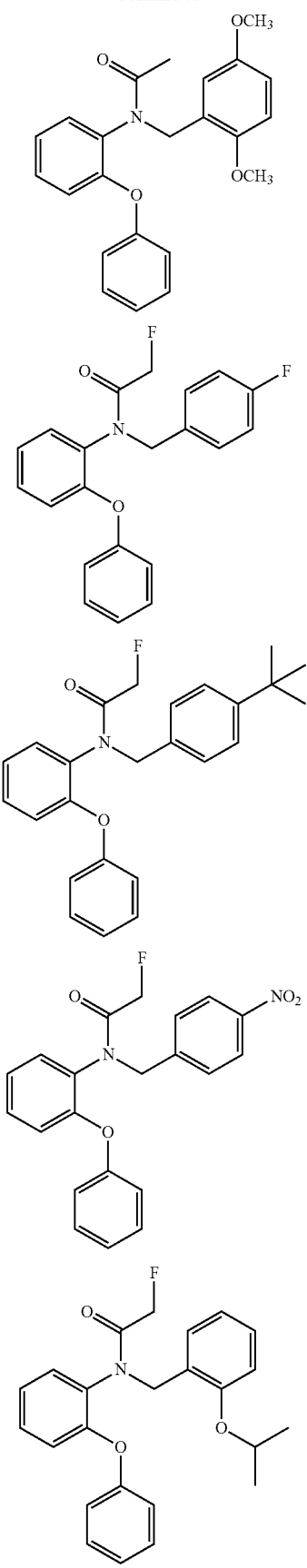

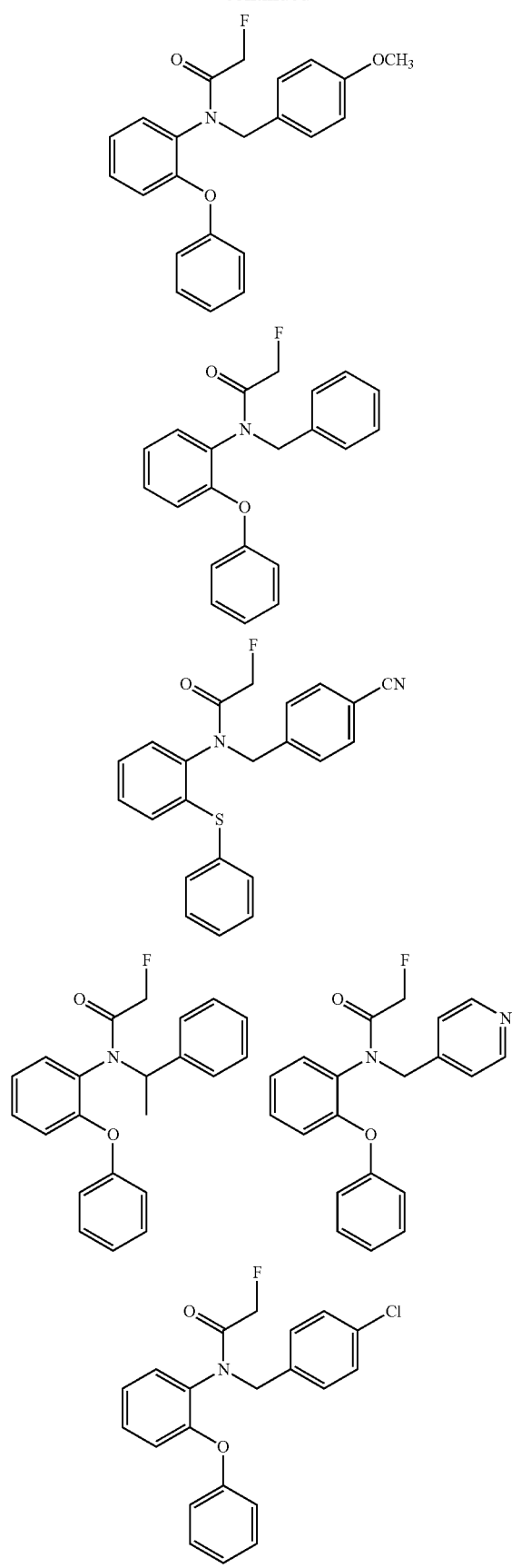
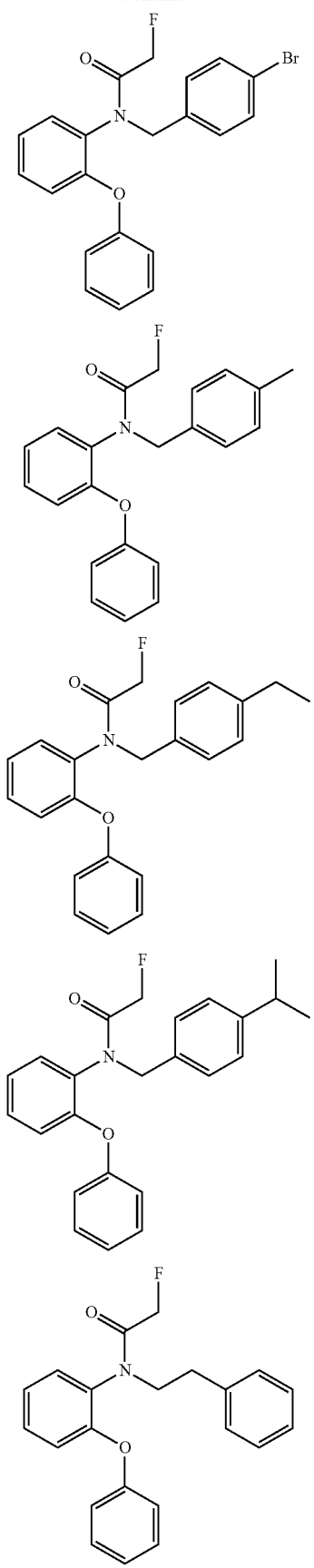

37
-continued
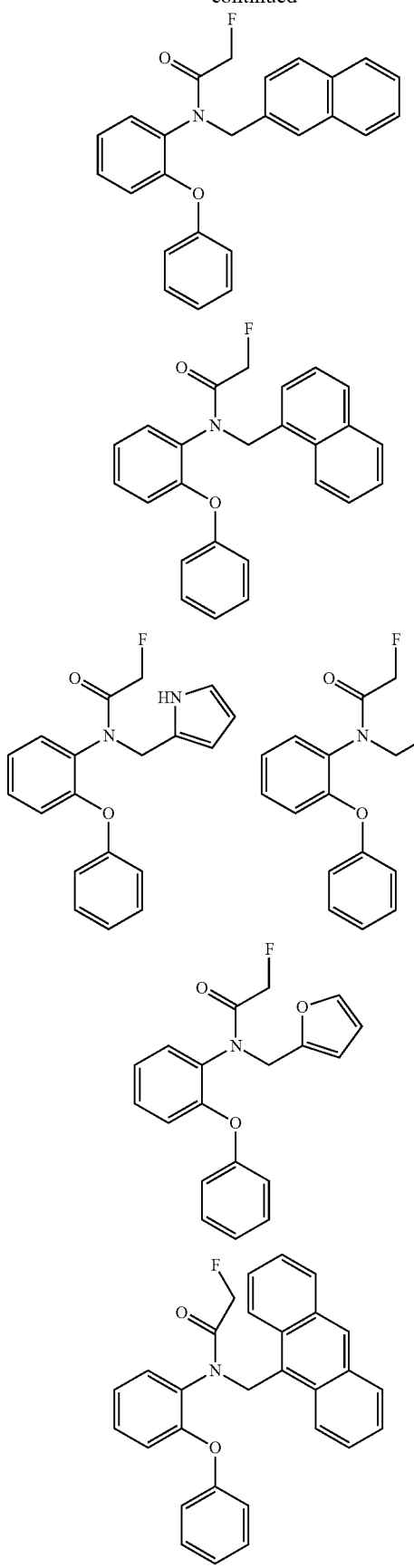
38
-continued
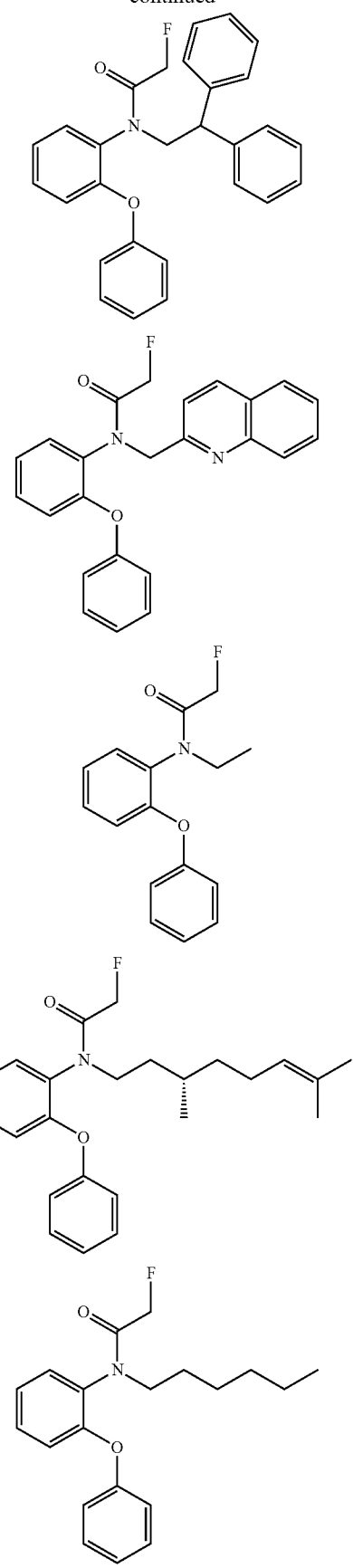

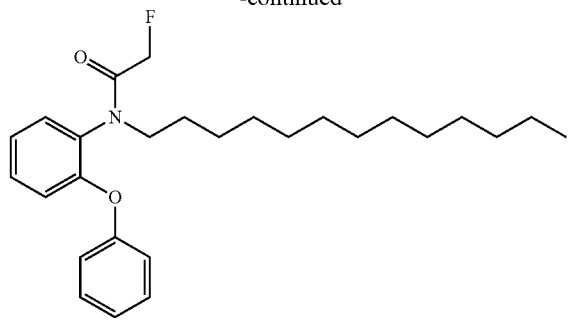
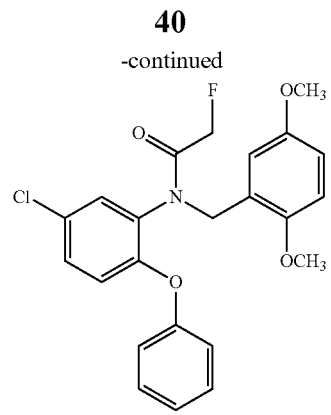
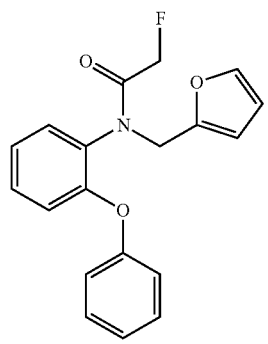
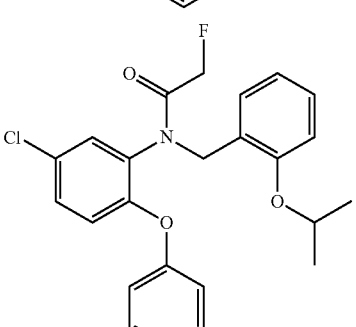
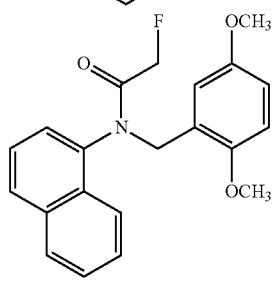
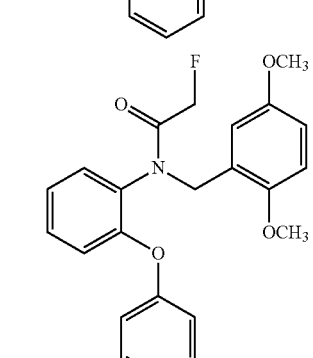
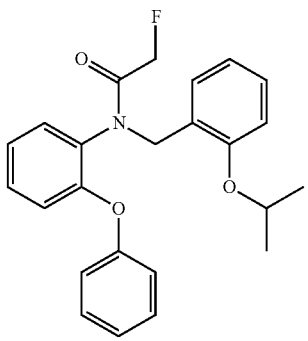
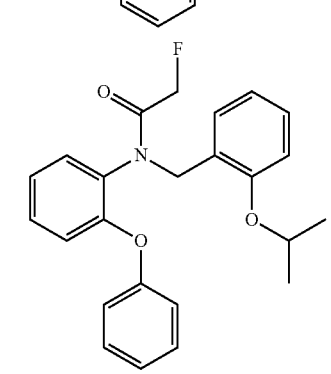
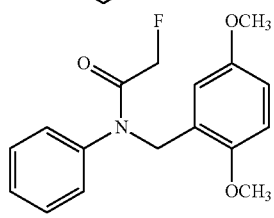
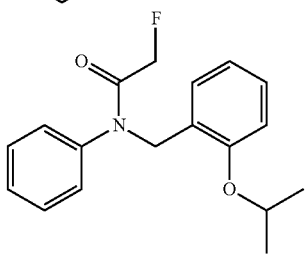
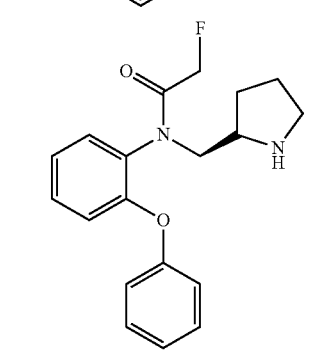

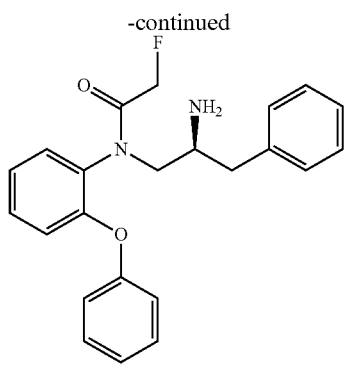

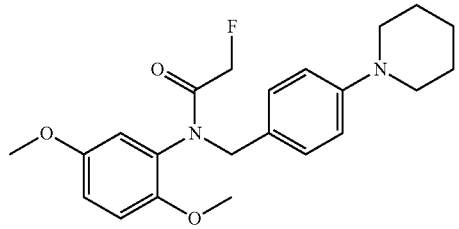

89D

Chemical Formula: C$_{22}$H$_{27}$FN$_2$O$_3$
Exact Mass: 386.2006
Molecular Weight: 386.4598

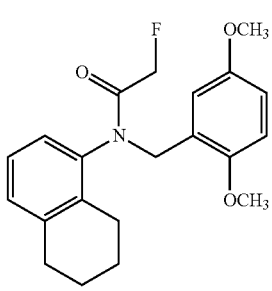

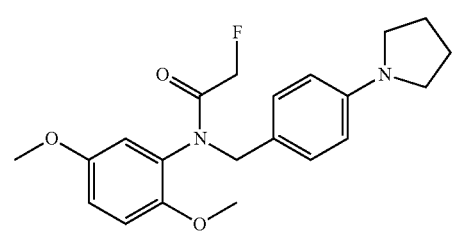

89E

Chemical Formula: C$_{21}$H$_{25}$FN$_2$O$_3$
Exact Mass: 372.1849
Molecular Weight: 372.4332

89A

Chemical Formula: C$_{14}$H$_{20}$FNO$_3$S
Exact Mass: 301.1148
Molecular Weight: 388.3769

89B

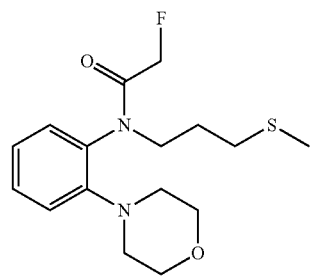

87A

Chemical Formula: C$_{16}$H$_{23}$FN$_2$O$_2$S
Exact Mass: 326.1464
Molecular Weight: 326.4294

Chemical Formula: C$_{21}$H$_{25}$FN$_2$O$_4$
Exact Mass: 388.1798
Molecular Weight: 388.4326

89C

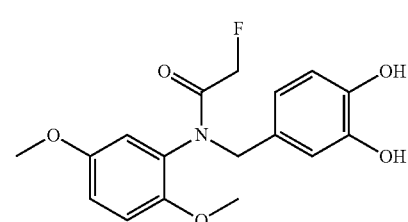

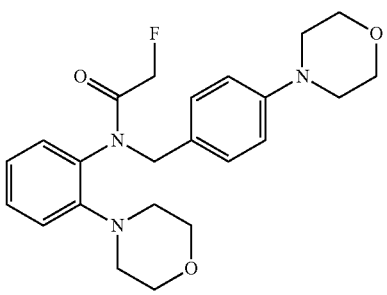

87B

Chemical Formula: C$_{17}$H$_{18}$FNO$_5$
Exact Mass: 335.1169
Molecular Weight: 335.3269

Chemical Formula: C$_{23}$H$_{28}$FN$_3$O$_3$
Exact Mass: 413.2115
Molecular Weight: 413.7851

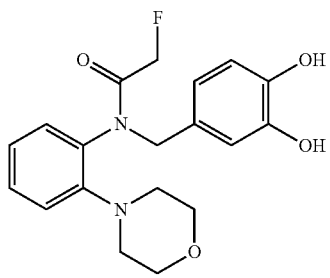

Chemical Formula: C₁₉H₂₁FN₂O₄
Exact Mass: 360.1485
Molecular Weight: 360.3794

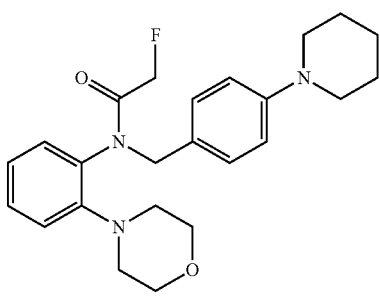

Chemical Formula: C₂₄H₃₀FN₃O₂
Exact Mass: 411.2322
Molecular Weight: 411.5123

87E

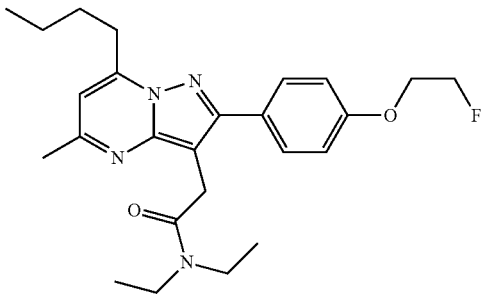

Chemical Formula: C₂₃H₂₈FN₃O₂
Exact Mass: 397.2166
Molecular Weight: 397.4857

VUIIS-1018

87C

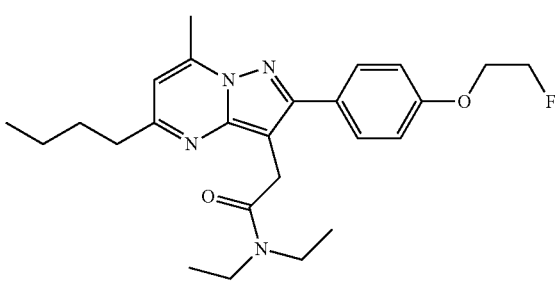

VUIIS-1019

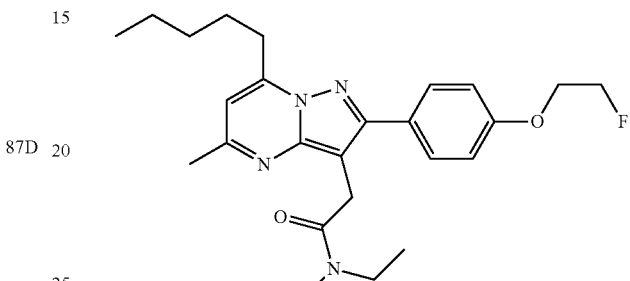

VUISS-1020

87D

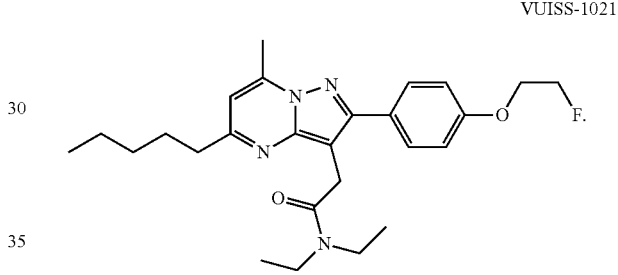

VUISS-1021

As indicated above, each compound of the present invention may be radiolabeled. More specifically, a compound of the present invention can be radiolabelled with, for example, $^{18}$F, $^{123}$I, $^{76}$Br, $^{124}$I or $^{75}$Br by standard techniques known in organic chemistry for modifying an organic compound to replace a hydrogen or halo group in the compound $^{18}$F, $^{123}$I, $^{76}$Br, $^{124}$I or $^{75}$Br. Alternatively, compounds of the present invention radiolabelled with a radioisotope selected from $^{18}$F, $^{123}$I, $^{76}$Br, $^{124}$I or $^{75}$Br may be prepared by incorporating $^{18}$F, $^{123}$I, $^{76}$Br, $^{124}$I or $^{75}$Br as a substituent in one of the starting materials or in an intermediate used in the synthesis of a compound of the present invention.

A compound of the present invention radiolabelled with, for example, $^{18}$F, $^{123}$I, $^{76}$Br, $^{124}$I or $^{75}$Br may, for example, be prepared by preparing a compound of the present invention defined above, but in which a substituent is substituted with a leaving group, such as tosylate, mesylate, Br or I, that allows an aliphatic nucleophilic substitution reaction to occur at the leaving group, and then subjecting the compound to conditions under which an aliphatic nucleophilic substitution reaction occurs to replace the leaving group with $^{18}$F, $^{123}$I, $^{76}$Br, $^{124}$I or $^{75}$Br. For example, when the leaving group is Br or tosylate, the compound may be reacted with the [$^{18}$F]-kryptofix-K222 complex in acetonitrile at about 80° C. for 10 minutes to form a compound of the present invention radiolabelled with $^{18}$F.

Compounds of the present invention radiolabelled with $^{18}$F, $^{123}$I, $^{76}$Br, $^{124}$I or $^{75}$Br may also be formed by forming a compound of the present invention, but as a substituent, stannyl, silyl or halogen (the halogen substituent is usually different to the radioisotope), and subjecting the compound to an electrophilic substitution reaction in acetic media using an oxidizing agent such as chloramine-T to form a compound of the present invention radiolabelled with $^{123}$I, $^{76}$Br, $^{124}$I or $^{75}$Br. In some embodiments, this reaction may be carried out at room temperature, and in other embodiments, the reaction mixture is heated to about 80-100° C. A compound of formula (I) as defined above, but in which one of the substituents substituted with a leaving group, may be prepared by analogous processes to the processes for preparing compounds of the present invention described in Selleri et al. (2001) or Selleri et al. (2005) but in which an appropriate reactant is substituted with the leaving group. Alternatively, a compound of the present invention may be modified by reactions known in organic chemistry to introduce a leaving group as a substituent.

The compound of the present invention may be radiolabelled with $^{18}$F (half-life 110 minutes), $^{123}$I (half-life 13.2 hours), $^{76}$Br (half-life 16.2 hours), $^{124}$I (half-life 4.2 days) or $^{75}$Br (half-life 1.6 hours). Typically, compounds of the present invention are radiolabelled with $^{18}$F. However, compounds of the present invention can be radiolabelled with, for example, $^{18}$F, $^{123}$I, $^{76}$Br, $^{124}$I or $^{75}$Br by standard techniques known in organic chemistry for modifying an organic compound to replace a hydrogen or halo group in the compound $^{18}$F, $^{123}$I, $^{76}$Br, $^{124}$I or $^{75}$Br. Alternatively, compounds of the present invention radiolabelled with a radioisotope selected from $^{18}$F, $^{123}$I, $^{76}$Br, $^{124}$I or $^{75}$Br may be prepared by incorporating $^{18}$F, $^{123}$I, $^{76}$Br, $^{124}$I or $^{75}$Br as a substituent in one of the starting materials or in an intermediate used in the synthesis of a compound of the present invention.

Preparations for parenteral administration are typically in the form of a sterile aqueous or non-aqueous solution, suspension or emulsion. Examples of suitable non-aqueous solvents are propylene glycol, polyethylene glycol, vegetable oils such as olive oil, and injectable organic esters such as ethyl oleate. Suitable aqueous carriers include water and alcoholic/aqueous solutions, emulsions or suspensions, including saline and buffered media. Suitable parenteral vehicles include sodium chloride solution.

One embodiment of the present invention is measuring TSPO expression in tumors to evaluate treatment response. Emerging data from our laboratory suggests that TSPO expression is significantly reduced in human CRC xenograft tumors that are responding to molecularly targeted therapy. For example, we recently treated athymic nude mice bearing DiFi colorectal cancer xenografts with mAb-C225 (Cetuximab, Erbitux, C225), a clinically approved therapeutic monoclonal that blocks ligand-induced activation of the epidermal growth factor receptor (EGFR). We have considerable previous experience with the DiFi model (wt KRAS), which was derived from a rectal tumor arising in a patient with familial polyposis. Following C225, DiFi tumors apoptose in a FOXO3A/Bim-dependent manner and cell cycle is regulated through p27, especially at elevated dosages (data not shown). The present inventors found that TSPO expression in DiFi tumors is significantly decreased following treatment with C225 compared with similar vehicle treated cohorts (FIG. 1). A close relationship between TSPO expression and Ki67 was noted, suggesting that TSPO levels are reflecting proliferation, showing that imaging probes capable of assaying TSPO expression could be potentially inform tumor responses to treatment.

The earliest published evidence supporting the hypothesis that TSPO ligands could be useful for detection and possibly grading of human brain tumors emerged more than twenty years ago, easily pre-dating molecular studies seeking elucidation of TSPO's role in tumorogenesis, many of which continue today. The first proof-of-principle imaging studies employed [$^3$H]PK 11195 and autoradiography to visualize TSPO expression in experimental models of glioma and post-mortem human brain sections. These ex vivo studies established that [$^3$H]PK 11195, a highly selective TSPO ligand without appreciable affinity for the central benzodiazepine receptor, could discriminate brain tumors from normal cortex. Furthermore, the amount of ligand uptake appeared to be proportional to tumor aggressiveness, cell proliferation, and tumor grade. Supported by these data, the first human PET studies using [$^{11}$C]PK 11195 to image brain tumors were conducted, and these seminal investigations led to a number of important observations. In one report, Junck et al. imaged a range of human gliomas with [$^{11}$C]PK 11195, as well as a different TSPO ligand, [$^{11}$C]Ro5-4864. While both PK 11195 and Ro5-4864 are potent and selective TSPO ligands with in vitro affinity in the low nanomolar range, this study established the clear superiority of [$^{11}$C]PK 11195 over [$^{11}$C]Ro5-4864 for brain tumor imaging. Surprisingly, PET scans with [$^{11}$C]Ro5-4864 failed to demonstrate higher levels of radioactivity in tumor tissue than in normal brain, supporting an earlier autoradiography study comparing [$^3$H] PK 11195 with [$^3$H]Ro5-4864. In contrast, [$^{11}$C]PK 11195 demonstrated significantly elevated uptake in gliomas in 8/10 patients when compared to contralateral normal brain, with tumor/gray matter ratios approaching 2 in 3/10 patients. In addition to the tumor-selective nature of [$^{11}$C]PK 11195, these data illustrate that chemical, biochemical, and pharmacological determinant are not well understood regarding the rational selection of TSPO ligands as potential cancer imaging probes. In subsequent investigations, Pappata et al. found similar levels of [$^{11}$C]PK 11195 uptake in a glioma study when compared to the study reported by Junck et al. However, these authors also performed a displacement study using nonradioactive ligand in this patient and demonstrated that slightly less than 30% of the [$^{11}$C]PK 11195 was displaceable. Although both of these studies suggest the utility of TSPO ligands for brain tumor imaging, the relatively modest uptake and attendant contrast afforded by [$^{11}$C]PK 11195 in tumor tissue compared to normal brain, despite considerably larger differences in relative TSPO expression, coupled with high levels of non-displaceable ligand binding, suggest that exploration and development of novel TSPO ligands could improve the prospects of advancing TSPO as a cancer imaging biomarker.

Additionally, embodiments of the present invention are methods for predicting response to therapy. Data from the present invention suggest that tumor TSPO expression could be used to predict response to therapy. For example, we have observed that TSPO expression is significantly reduced in responsive human colorectal cancer (CRC) xenograft tumors following the first dose of an effective molecularly targeted therapy. For example, treatment of DiFi CRC xenografts with mAb-C225 (Cetuximab, Erbitux, C225), a therapeutic monoclonal antibody that blocks ligand-induced activation of the epidermal growth factor receptor (EGFR), results in a significant reduction of TSPO as measured by immunohistochemistry (FIG. 1). We have considerable experience with DiFi xenografts (wt KRAS), derived from a rectal tumor arising in a patient with familial polyposis. Following C225, DiFi tumors apoptose in a FOXO3A/Bim-dependent manner and cell cycle is regulated through p27 (data not shown). In these studies, we noted a close relationship between TSPO expression and Ki67, suggesting a correlation between TSPO levels and proliferation in this model. Though preliminary, this data suggests, for the first time, a potential role for assaying TSPO expression to predict response to treatment in tumors.

Additionally, TSPO expression could have the most immediate impact on glioma. Malignant gliomas are the most common primary brain tumors and represent a particularly lethal form of cancer. They are characterized by invasive growth and recalcitrance to therapy, thus patients with malignant gliomas currently have a very poor prognosis. Malignant gliomas are classified according to histological appearance and degree of malignancy according to criteria established by the World Health Organization (WHO). General survival times are 5-15 years for grade II gliomas, 2-5 years for grade III, and one year for grade IV. TSPO expression levels correlate with glioma tumor grade; accordingly, we hypothesize that TSPO imaging ligands will be instrumental assets for glioma diagnosis and therapeutic trials. Currently, the diagnosis and grading of gliomas are based upon the pathology of biopsy or resected specimens, with limitations inherent to sampling heterogeneous tumors. In the absence of repeat biopsies, clinical decisions to continue or discontinue therapies are routinely guided by imaging. Clinically, two of the most common imaging metrics employed to detect and diagnose brain tumors are computed tomography (CT) and magnetic resonance imaging (MRI). These modalities provide little, if any, molecular information attributable to the pathological status of the disease. Furthermore, numerous studies document the inherent difficulty associated with visualization of the true extent of brain tumor pathology using CT and/or MRI, particularly with highly infiltrative disease. Positron emission tomography imaging using $^{18}$FDG is an important technique for brain tumor detection, but high glucose uptake in normal brain results in modest tumor-to-background ratios, which can confound delineation of disease margins and subsequent grading. An alternative and potentially superior approach is L-[methyl-$^{11}$C] methionine ($^{11}$C-methionine). Though promising, the half-life of $^{11}$C (20.4 min) limits the broad implementation of this technique when compared to $^{18}$F (109.8 min). Therefore, there is a considerable need to develop and validate improved molecular imaging techniques suitable for detection and/or molecular profiling of brain tumors.

Several TSPO specific ligand scaffolds are currently known including the aryloxyanilides (1), indolacetamides-indoleacetamides (2), pyrazolopyrimidines (3), indolylglyoxylylamides (4), benzodiazepines (5), and isoquinoline carboxamides (6).

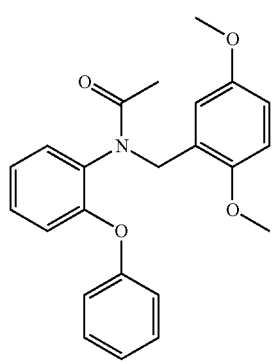

Aryloxyanilide

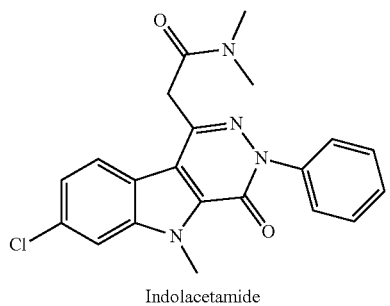

Indolacetamide

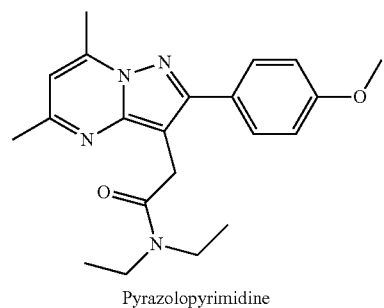

Pyrazolopyrimidine

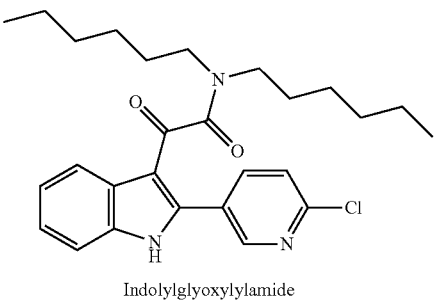

Indolylglyoxylylamide

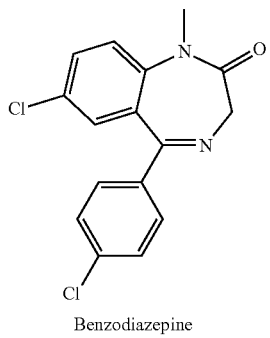

Benzodiazepine

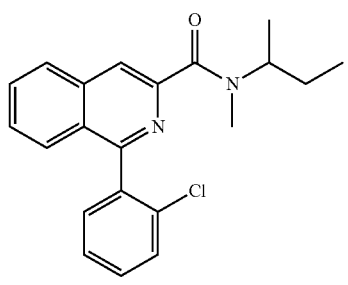

Isoquinoline Carboxamide

Based upon these relatively diverse scaffolds, several PET imaging probes have been previously developed for evaluating neuroinflammation. Some of these imaging probes include [11C]PK11195 and [18F]PK14105, [11C]VC195, [11C]VC193M, [11C]Ro5-4864, [11C]DPA-713, [18F]DPA-714, [11C]DAA1106, [18F]FMDAA1106 and [18F]FEDAA1106, [11C]PBR28, and [11C]PBR01.

Examples of aryloxyanilide and pyrazolopyrimidine derivatives of the present invention are outlined below.

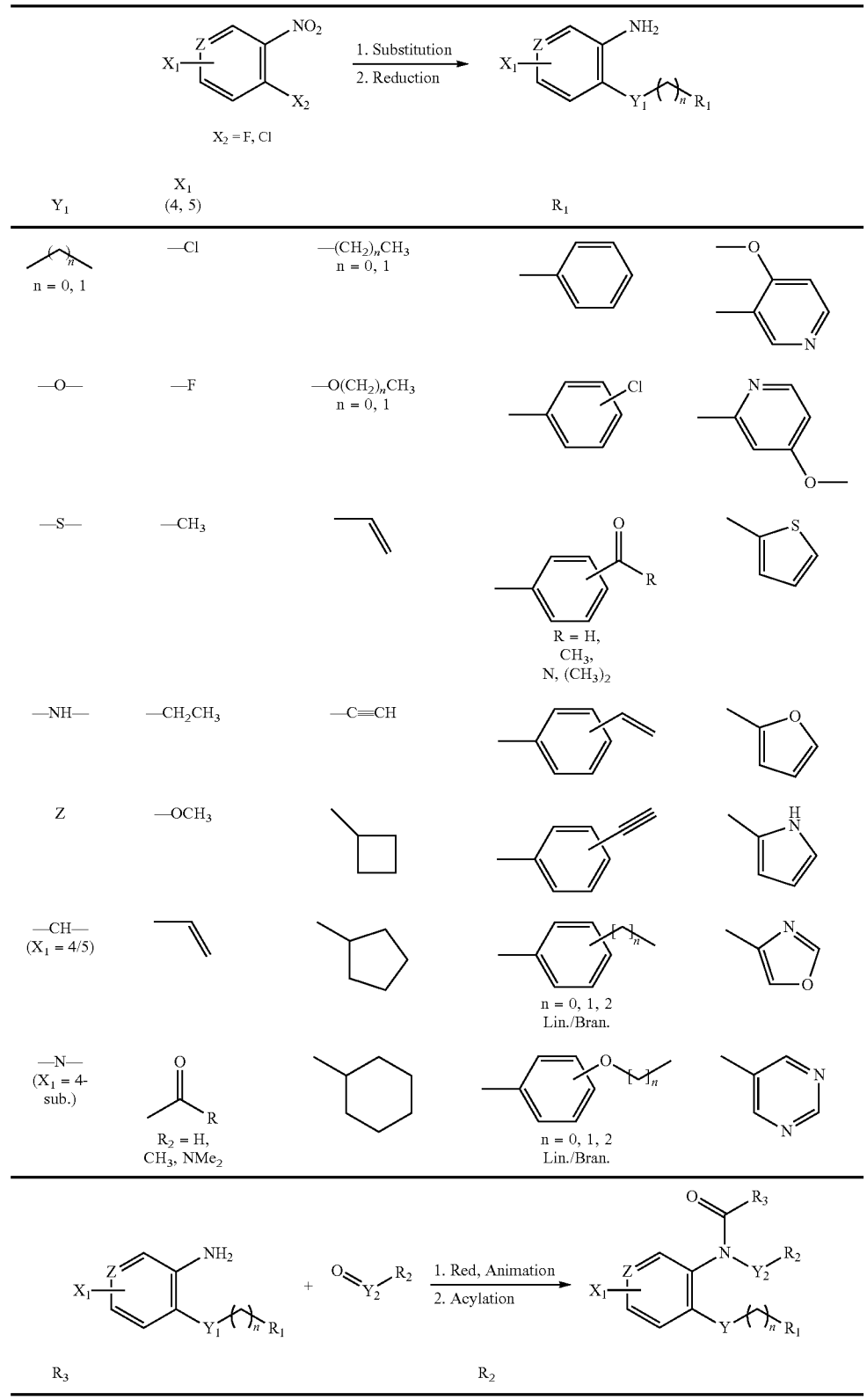

-continued
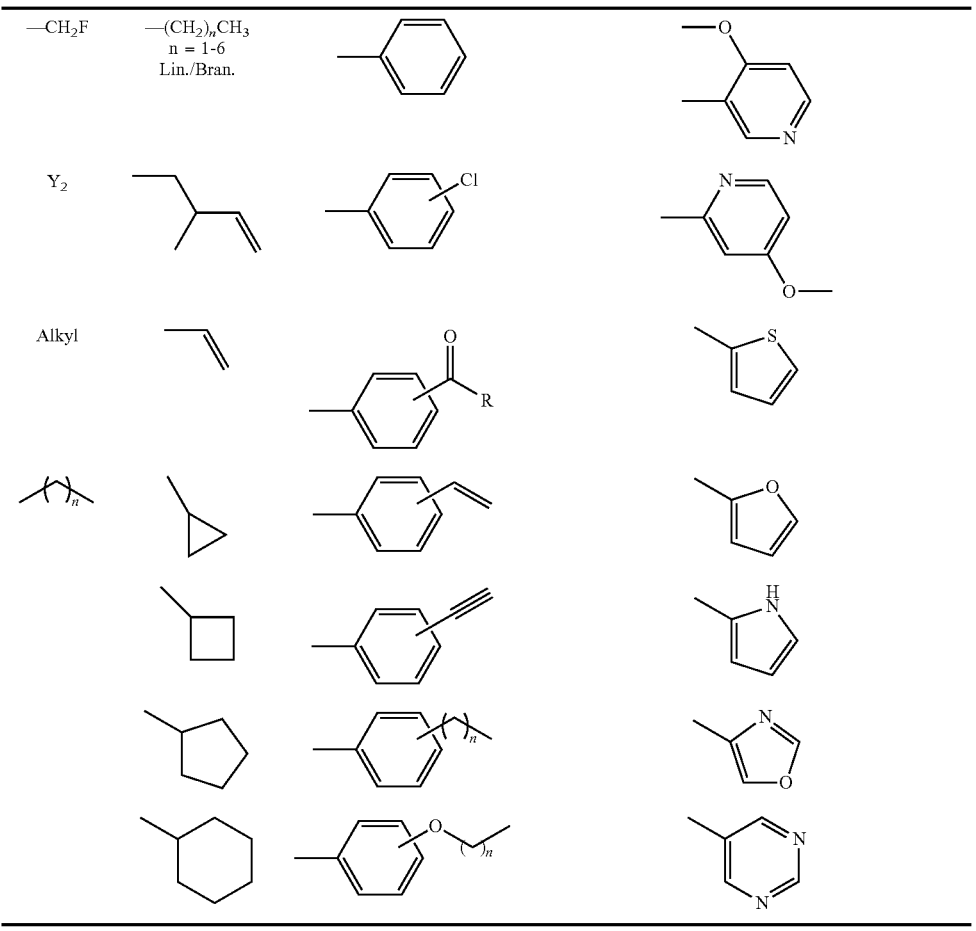
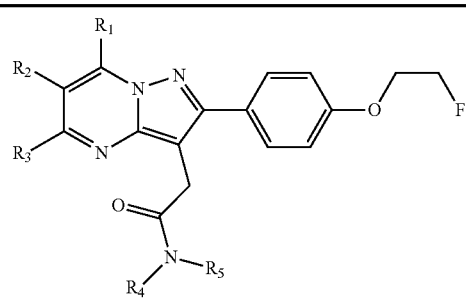
| $R_1/R_3$ | | $R_2$ | $R_4/R_5$ | |
|---|---|---|---|---|
| —CH$_3$ | (thiophene) | —H | —H | (phenyl) |
| —CH$_2$CH$_3$ | (phenyl) | —CH$_3$ | —CH$_3$ | (phenyl ketone) |
| —CF$_3$ | (furan) | —CH$_2$CH$_3$ | —CH$_2$CH$_3$ | |
| —(CH$_2$)$_2$CH$_3$ | (pyridine) | —(CH$_2$)$_2$CH$_3$ | —(CH$_2$)$_2$CH$_3$ | |
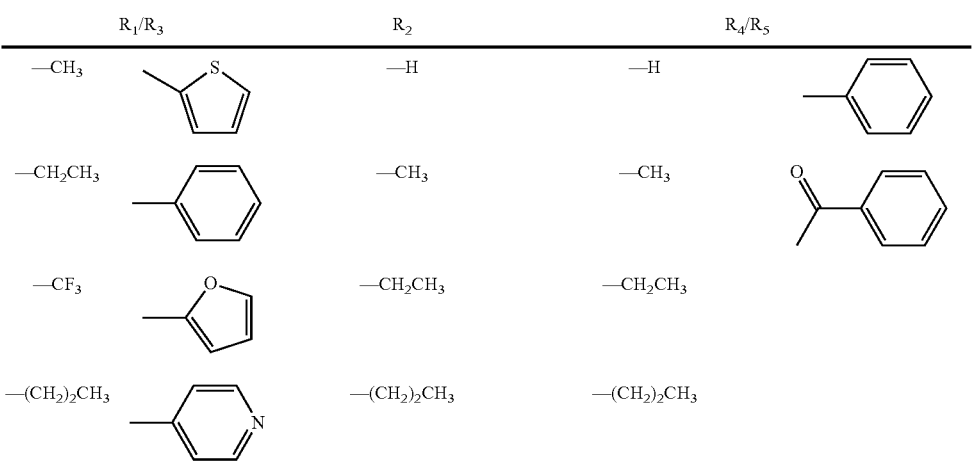

-continued

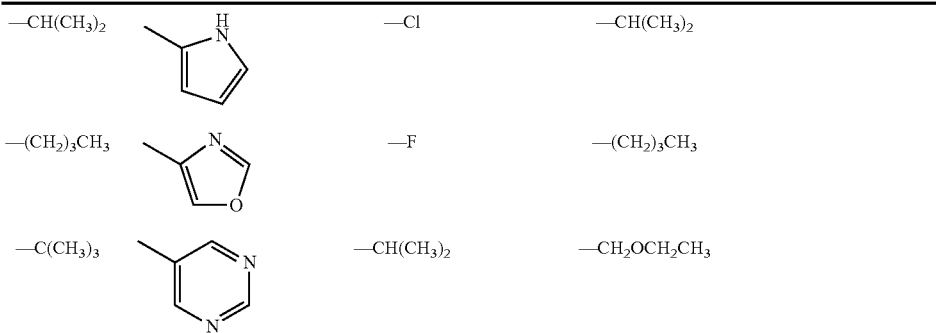

Pyrazolopyrimidines of the Present Invention

Figure 4:
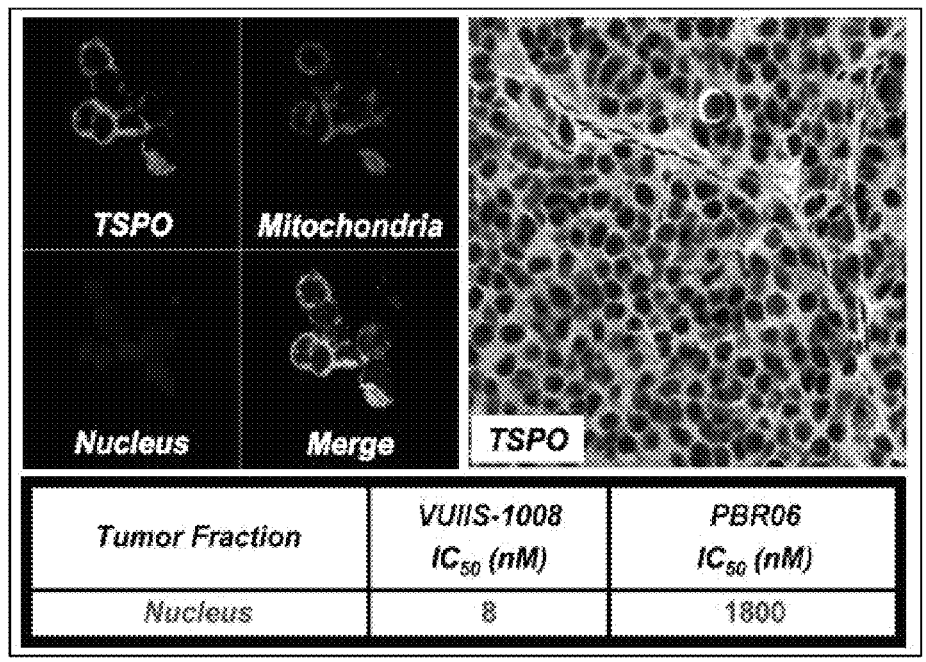
FIG. 4 shows that TSPO compartmentalization in tumors can favor certain TSPO ligands for cancer imaging studies. Confocal immunofluorescence images of cultured DiFi human CRC cells demonstrate exclusive localization of TSPO to the mitochondria (left). When propagated as DiFi xenografts in nude mice, TSPO is mitochondrial and strongly nuclear (TSPO IHC, right). Fractional displacement assay shows VUIIS-1008, but not PBR06, targets nuclear TSPO.

TSPO is typically localized to the mitochondria in most normal tissues. However, in aggressive, potentially metastatic tumors TSPO can also be found in the nucleus, an important departure from normal tissues. Indeed, not all tumors exhibit nuclear TSPO, but those that do are clearly the most important to identify. A major step forward in TSPO ligand discovery for cancer imaging is the selection of ligands capable of binding nuclear TSPO with high affinity. The present inventors have made discoveries involving nuclear TSPO expression in tumors. First, in vitro and in vivo TSPO localization can vary dramatically in a single cell line. For example, as shown in FIG. 4, TSPO is exclusively mitochondrial in cultured DiFi cells, a human CRC cell line, yet primarily nuclear in DiFi xenografts. We have capitalized upon this observation in our screening assays, whereby compounds can be easily triaged based upon their ability to target exclusively one, or both TSPO compartments. Compartmentalization is central to the present inventor's discovery that TSPO imaging ligands that are effective probes in neuroscience may not be ideally suited for cancer imaging studies. Evidence supporting this hypothesis can be found in our discovery of [$^{18}$F]VUIIS-1008, a novel, high-affinity (~1 nM) TSPO ligand that appears to bind TSPO in certain tumors in an irreversible fashion, yet reversibly binds many normal tissues.

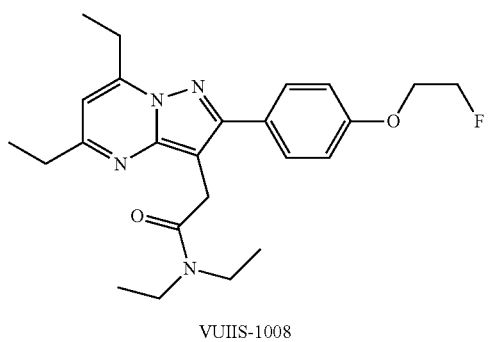

VUIIS-1008

VUIIS-1008 was initially prioritized for probe development because we observed in fractional, nuclear binding assays, that this compound displaced [$^3$H]PK 11195 with nanomolar binding affinity (FIG. 4). In contrast, the aryloxyanilide PBR06 does not exhibit appreciable affinity for nuclear TSPO, despite exhibiting excellent binding affinity (~12 nM) in whole tumor lysate. The difference in compartmentalization between these two compounds is only discernible in fractional studies. Based upon this observation, we developed [$^{18}$F]VUIIS-1008 and have evaluated this agent in preclinical cancer imaging studies. In vivo performance of this agent suggests that targeting nuclear and mitochondrial fractions manifests in significantly greater discrimination between neoplastic and normal tissue. It is also conceivable that the nuclear compartmentalization of this agent is at least partially responsible for the irreversible binding observed in tumors.

Another example of a compound of the present invention is VUIIS-0005.

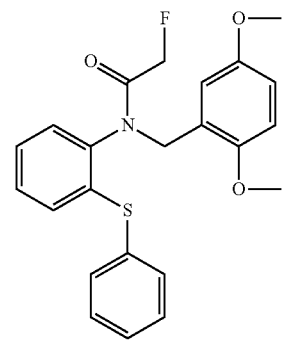

VUIIS-0005

Figure 5:
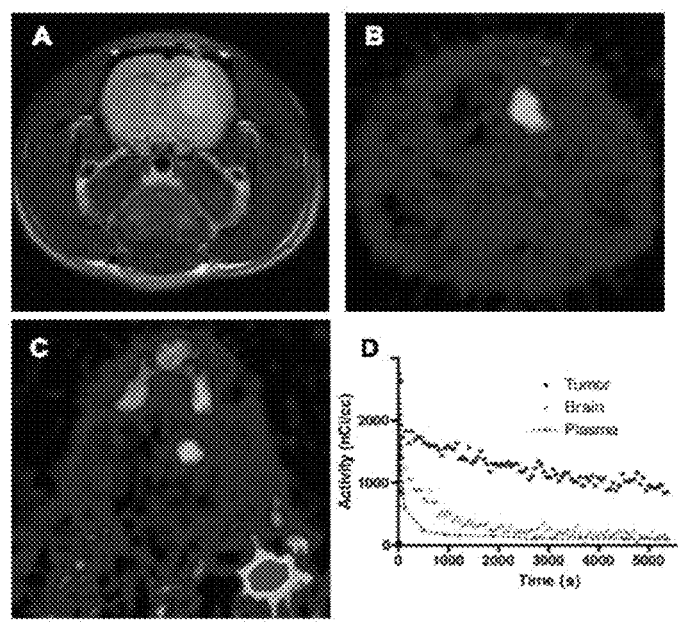
FIG. 5 shows an in vivo evaluation of [$^{18}$F]VUIIS-0005, a high-affinity aryloxyanilide, in a C6 glioma. In vivo uptake of this TSPO ligand is primarily confined to tumor tissue, with significantly less normal brain uptake compared to $^{18}$F-PBR06.
Figure 6:
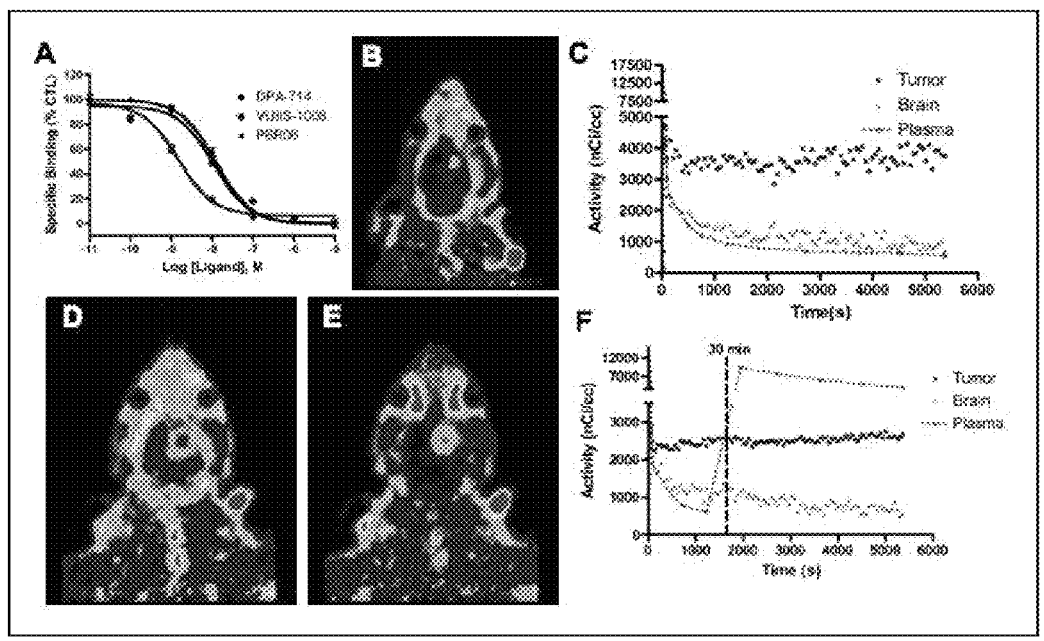
FIG. 6 shows an in vivo evaluation of [$^{18}$F]VUIIS-1008, a high-affinity, TSPO ligand. (A) Shows that in vitro $IC_{50}$ of VUIIS-1008 against $^3$H-PK 11195 in tumor lysate is approximately 10-fold lower than either PBR06 or DPA-714 (~1 nM vs. 12 nM). (B) and (C) shows that [$^{18}$F]VUIIS-1008 exhibits robust tumor uptake, yet very little normal brain uptake, facilitating excellent contrast between tumor and surrounding normal brain. (D), (E), and (F) show that in vivo displacement of [$^{18}$F]VUIIS-1008 with 'cold' VUIIS-1008 results a 25-fold increase in tracer levels in plasma and displacement from various normal tissues. Tumor localization may be irreversible.

Both [$^{18}$F]VUIIS-0005 and [$^{18}$F]VUIIS-1008 exhibit improved binding affinity in tumor lysate compared to PBR06 or DPA-714, as well as additional, 'tumor-centric' qualities such as nuclear targeting. Evaluation of both of these agents suggests these are superior cancer imaging probes. Compared to [$^{18}$F]PBR06 or [$^{18}$F]DPA-714, [$^{18}$F]VUIIS-0005 and [$^{18}$F]VUIIS-1008 exhibit significantly reduced normal brain uptake, facilitating improved contrast between tumor and surrounding normal tissue (FIGS. 5 and 6). Furthermore, $^{18}$F-VUIIS-1008 has the attractive feature of exhibiting selective, irreversible binding to tumor tissues. As shown in FIG. 6(D-F), infusion of 'cold' VUIIS-1008 following [$^{18}$F]VUIIS-1008 results in a 25-fold increase in tracer-plasma levels and displacement from various normal tissues, yet no detectable displacement from the tumor. For brain tumor imaging, as proposed in these studies, both of these tracers appear to be highly promising candidates worthy of additional in vivo evaluation. Importantly, this preliminary data demonstrates the feasibility of preparing increasingly tumor-specific TSPO ligands using approaches outlined in this application.

Figure 7:
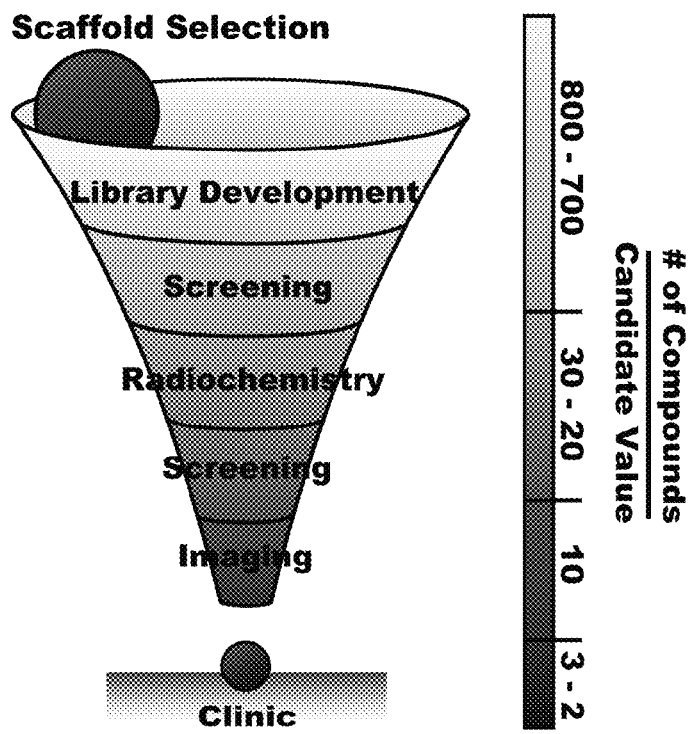
FIG. 7 shows a schematic overview of the overall research strategy for the development of novel TSPO ligands for cancer imaging.

FIG. 7 represents an example of a schematic overview of the proposed research workflow. Examples of the present invention include libraries of novel aryloxyanilides and pyrazolopyrimidines and aggressively triage candidates based upon tumor-centric' TSPO ligand activity. Tumor-selective leads are labeled with fluorine-18. Leads that are labeled and produced in high-specific activity are evaluated as imaging probes in preclinical models of human cancer.

Embodiments of the present invention include methods of making and using compounds having a parent scaffold of DPA-713/DPA-714, a pyrazolopyrimidine compound with nanomolar binding affinity against [$^3$H]PK11195.

Further embodiments include novel pyrazolopyrimidine compounds that demonstrate improved TSPO activity when compared to existing TSPO ligands.

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids" includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient.

Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent.

Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As examples, pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms. Additionally, pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Further disclosed herein are pharmaceutical compositions comprising one or more of the disclosed TSPO receptor ligands and a pharmaceutically acceptable carrier.

Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient can be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be coadministered, either in concomitant therapy or in a fixed combination.

Additionally, the compounds of the present invention inhibit the activity of ERK. Thus, this invention further provides a method of inhibiting ERK in mammals, especially humans, by the administration of an effective amount (e.g., a therapeutically effective amount) of one or more (e.g., one) compounds of this invention. The administration of the compounds of this invention to patients, to inhibit ERK, pERK, ERK1 and/or ERK2, is useful in the treatment of cancer.

Additionally, the present invention further provides a method of inhibiting HER2 in mammals, especially humans. HER2 is a transmembrane surface-bound receptor tyrosine kinase and is normally involved in the signal transduction pathways leading to cell growth and differentiation. HER2, also known as epidermal growth factor receptor 2, belongs to a family of epidermal growth factor receptors (EGFRs) including HER1 (ErbB1), HER3 (ErbB3), and HER4 (ErbB4) (Hudis, 2007, N Engl J Med 357(1):39-51). Overexpression of HER2 results in the induction of angiogenesis, a component of cancer growth, and the evocation of an antitumor T-cell response (Menard et al., 2003, Oncogene 22:6570-6578). HER2 is overexpressed in about one-quarter of breast cancer patients (Bange et al., 2001, Nature Medicine 7:548-552). Thus, as stated above, compounds of the present invention are useful in treating cancer, particularly breast cancer.

In any of the methods of treating cancer described herein, unless stated otherwise, the methods can optionally include the administration of an effective amount of one or more chemotherapeutic agents. The chemotherapeutic agents can be administered currently or sequentially with the compounds of this invention.

Examples of these agents include the administration of a compound of the present invention in combination with an anti-HER2 compound. The development of a monoclonal antibody therapy based on the discovery of the role of HER2 in breast cancer first involved the development of a murine-based antibody. Researchers discovered that the murine monoclonal antibody 4D5 had a significant and dose dependent efficacy specifically for HER2 overexpressing cancer cells, while having no effect on cells expressing physiological levels of HER2. However, murine antibodies elicit an immunogenic response in human patients. Murine monoclonal antibodies can be humanized (thereby reducing the murine-induced immune response) by identification of a minimum set of amino acid residues in the complementarity determining regions (CDRs) of the murine antibody required for antigen specificity and antigen binding affinity and substituting these regions into the CDRs of a consensus human IgG framework. The framework regions are the non-CDR regions in the variable chains of the antibody. Accordingly, the murine (4D5) monoclonal antibody was humanized, resulting in a recombinant, humanized monoclonal antibody directed against HER2. This drug is commercially known as Herceptin® (trastuzumab), which gained FDA marketing approval in late 1998.

Herceptin® is known to bind with high affinity to the extracellular domain of the Her2 protein, thereby inhibiting the proliferation of human tumor cells that overexpress HER2. Herceptin® is also a mediator of antibody-dependent cellular cytotoxicity (ADCC) which has been shown to be preferentially exerted on Her2 overexpressing cancer cells compared with cancer cells that do not overexpress Her2.

Thus, an embodiment of the present invention includes a combination of a compound of the present invention with Trastuzumab or other monoclonal antibody, including those that interfere with the Her2 receptor. In various embodiments, the HER-2 inhibitor is selected from trastuzumab (Herceptin), pertuzumab (Omnitarg®), gefitinib, erlotinib, lapatinib, HKI-272, CI-1033, PKI-166, PD168393, and PD12878. In some embodiments, the HER-2 inhibitor is trastuzumab.

Additionally, the methods of treating cancer described herein include methods wherein a combination of drugs (i.e., compounds, or pharmaceutically active ingredients, or pharmaceutical compositions) are used (i.e., the methods of treating cancer of this invention include combination therapies). Those skilled in the art will appreciate that the drugs are generally administered individually as a pharmaceutical composition. The use of a pharmaceutical composition comprising more than one drug is within the scope of this invention.

In any of the methods of treating cancer described herein, unless stated otherwise, the methods can optionally include the administration of an effective amount of radiation therapy.

Examples of cancers which may be treated by the methods of this invention include, but are not limited to: (A) lung cancer (e.g., lung adenocarcinoma and non small cell lung cancer), (B) pancreatic cancers (e.g., pancreatic carcinoma such as, for example, exocrine pancreatic carcinoma), (C) colon cancers (e.g., colorectal carcinomas, such as, for example, colon adenocarcinoma and colon adenoma), (D) myeloid leukemias (for example, acute myelogenous leukemia (AML), CML, and CMML), (E) thyroid cancer, (F) myelodysplastic syndrome (MDS), (G) bladder carcinoma, (H) epidermal carcinoma, (I) melanoma, (J) breast cancer, (K) prostate cancer, (L) head and neck cancers (e.g., squamous cell cancer of the head and neck), (M) ovarian cancer, (N) brain cancers (e.g., gliomas, such as glioma blastoma multiforme), (O) cancers of mesenchymal origin (e.g., fibrosarcomas and rhabdomyosarcomas), (P) sarcomas, (Q) tetracarcinomas, (R) nuroblastomas, (S) kidney carcinomas, (T) hepatomas, (U) non-Hodgkin's lymphoma, (V) multiple myeloma, and (W) anaplastic thyroid carcinoma.

Accordingly, another embodiment of this invention is directed to a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, in a patient in need of such treatment, said method comprising administering to said patient an effective amount of at least one (e.g., 1, 2 or 3, 1 or 2, and usually 1) compound of the present invention.

Another embodiment of this invention is directed to a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of at least one compound of the present invention in combination with an effective amount of at least one chemotherapeutic agent.

In the methods of this invention wherein at least one chemotherapeutic agent is used, examples of such chemotherapeutic agents include, but are not limited to: taxanes such as paclitaxel (TAXOL®) and/or docetaxel (Taxotere®); platinum coordinator compounds, such as, for example, carboplatin, cisplatin and oxaliplatin (e.g. Eloxatin); EGF inhibitors that are antibodies, such as: HER2 antibodies (such as, for example trastuzumab (Herceptin®0, Genentech, Inc.), Cetuximab (Erbitux, IMC-C225, ImClone Systems), EMD 72000 (Merck KGaA), anti-EFGR monoclonal antibody ABX (Abgenix), TheraClM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), CI 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA); EGF inhibitors that are small molecules, such as, Tarceva (OSI-774, OSI Pharmaceuticals, Inc.), and Iressa (ZD 1839, Astra Zeneca); VEGF inhibitors that are antibodies such as: bevacizumab (Genentech, Inc.), and IMC-1C11 (ImClone Systems), DC 101 (a KDR VEGF Receptor 2 from ImClone Systems); VEGF kinase inhibitors that are small molecules such as SU 5416 (from Sugen, Inc), SU 6688 (from Sugen, Inc.), Bay 43-9006 (a dual VEGF and bRAF inhibitor from Bayer Pharmaceuticals and Onyx Pharmaceuticals); estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.); anti-tumor nucleoside derivatives such as 5-fluorouracil, gemcitabine, capecitabine, cytarabine (Ara-C), fludarabine (F-Ara-A), decitabine, and chlorodeoxyadenosine (Cda, 2-Cda); epothilones such as BMS-247550 (Bristol-Myers Squibb), and EP0906 (Novartis Pharmaceuticals); topoisomerase inhibitors such as topotecan (GlaxoSmithKline), and Camptosar (Pharmacia); *vinca* alkaloids, such as, navelbine (Anvar and Fabre, France), vincristine and vinblastine; antibodies that are inhibitors of aVβ 3 integrins, such as, LM-609 (see, Clinical Cancer Research, Vol. 6, page 3056-3061, August 2000, the disclosure of which is incorporated herein by reference thereto); folate antagonists, such as Methotrexate (MTX), and Premetrexed (Alimta); ribonucleotide reductase inhibitors, such as Hydroxyurea (HU); anthracyclines, such as Daunorubicin, Doxorubicin (Adriamycin), and Idarubicin; biologics, such as interferon (e.g., Intron-A and Roferon), pegylated interferon (e.g., Peg-Intron and Pegasys), and Rituximab (Rituxan, antibody used for the treatment of non-Hodgkin's lymphoma); thalidomide (or related imid); Bcr/abl kinase inhibitors, such as, for example Gleevec (STI-571), AMN-17, ONO 12380, SU11248 (Sunitinib) and BMS-354825; MEK1 and/or MEK2 inhibitors, such as PD0325901 and Arry-142886 (AZD6244); IGF-1 and IGF-2 inhibitors that are small molecules, such as, for example, NVP-AEW541; small molecule inhibitors of RAF and BRAF kinases, such as, for example, BAY 43-9006 (Sorafenib); small molecule inhibitors of cell cycle dependent kinases such as CDK1, CDK2, CDK4 and CDK6, such as, for example, CYC202, BMS387032, and Flavopiridol; alkylating agents, such as, for example, Temodar® brand of temozolornide; farnesyl protein transferase inhibitors, such as, for example:

(a) Sarasar® brand of Lonafarnib (i.e., 4-[2-[4-(3,10-dibromo-8-chloro-6,11-dihydro-5H-benzo [5,6]cyclohepta [1,2-b-]hyridin-11-yl)-1-piperidinyl)-2-oxoethyl]-1-piperidinecarboxamide (b) Zarnestra® brand of tipifarnib (i.e., (R)-6-amino[(4-chlorophenyl)(1-methyl-1H-imidazol-5-yl) methyl]-4-(3-chlor-ophenyl)-1-methyl-2(1H)-quinolinone and (c) Bristol-Myers Squibb 214662:

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56th Edition, 2002 (published by Medical Economics company, Inc. Montvale, N.J. 07645-1742), the Physician's Desk Reference, 57th Edition, 2003 (published by Thompson PDR, Montvale, N.J. 07645-1742); and the Physician's Desk Reference, 60th Edition, 2006 (published by Thompson P D R, Montvale, N.J. 07645-1742); the disclosures of which are incorporated herein by reference thereto.

For example, a compound of the present invention (e.g., a pharmaceutical composition comprising the compound of that inhibits Her2); can be administered orally (e.g., as a capsule), and the chemotherapeutic agents (e.g., an additional pharmaceutical compound that inhibits Her2) can be administered intravenously, usually as an IV solution. The use of a pharmaceutical composition comprising more than one drug is within the scope of this invention.

The compound of the present invention and the chemotherapeutic agents are administered in therapeutically effective dosages to obtain clinically acceptable results, e.g., reduction or elimination of symptoms or of the tumor. Thus, the compound of the present invention and the chemotherapeutic agent(s) can be administered concurrently or consecutively in a treatment protocol. The administration of the chemotherapeutic agents can be made according to treatment protocols already known in the art.

When two or more chemotherapeutic agents are used, the chemotherapeutic agents are generally administered on the same day; however, those skilled in the art will appreciate that the chemotherapeutic agents can be administered on different days and in different weeks. The skilled clinician can administer the chemotherapeutic agents according to their recommended dosage schedule from the manufacturer of the agent and can adjust the schedule according to the needs of the patient, e.g., based on the patient's response to the treatment.

However, those skilled in the art will appreciate that treatment protocols can be varied according to the needs of the patient. Thus, the combination of compounds (drugs) used in the methods of this invention can be administered in variations of the protocols described above. For example, the compounds of this invention can be administered discontinuously rather than continuously during the treatment cycle.

EXAMPLES

The following examples are intended to show certain embodiments of the present invention. They are exemplary of the present invention and are not to be construed as being limiting thereof.

Example 1A

This example demonstrates an example of a synthesis of a library of the present invention. In this example, the inventors employ Biotage Initiator 60 microwave system equipped with robotic sample manipulator to synthesize compounds.

Previous structure-activity studies show that substitution on the pyrimidine ring is an important determinant for the TSPO selectivity over the CBR and is important for developing high binding and highly selective compounds. Therefore, synthetic activities of this example focus on this portion of the molecule and will extend to additional potentially lipophilic pockets thought assist with TSPO binding. See below:

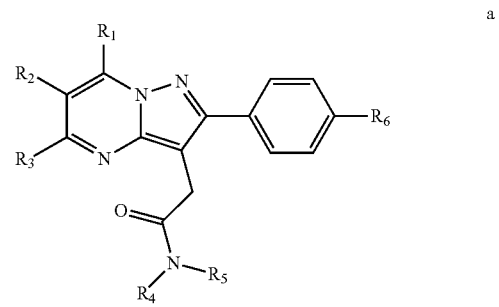

-continued

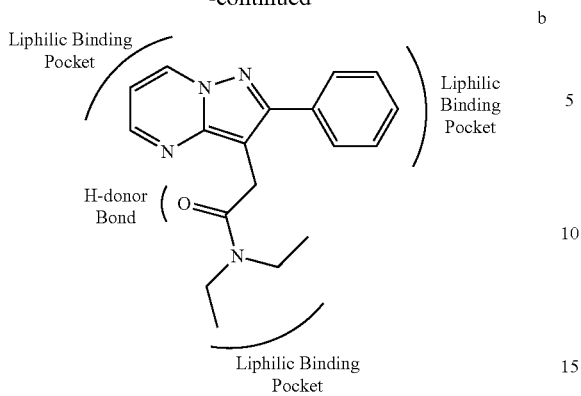

b

Modification of pyrazolopyrimidine and postulated binding area to TSPO.(Adapted from Reference (46)).

Generally, all of the analogues of this example can be synthesized in three steps, each utilizing MAOS. Our overall library-based approach emphasizes the introduction of chemical diversity applied at each of the three steps. As shown in Table 1, various starting materials utilized in the first step are greatly complemented by the diversity of commercially available diones utilized in the third reaction. Modified pyrazolopyrimidine ligands from this approach contain a variety of substitutions at the six positions (R1 to R6) (Scheme 1).

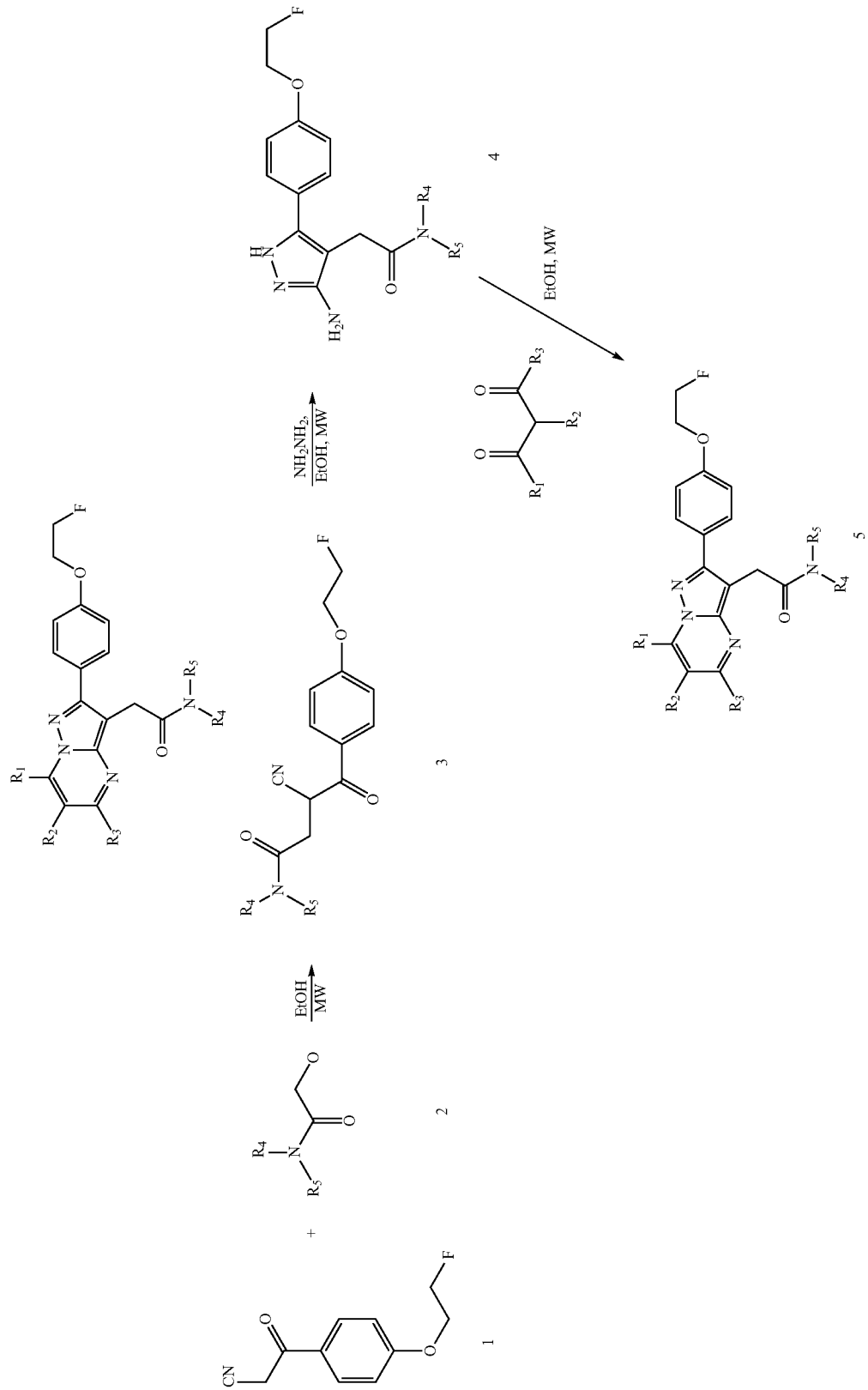
Scheme 1. Synthetic approach of pyrazolopyrimidines

With available reagents and reagents synthesized by the inventors, libraries of different pyrazolopyrimidines are created that include compounds exemplified in the table below. Following synthesis, compounds are purified using flash chromatography, HPLC and/or crystallization and rigorously characterized using high-resolution mass-spectrometry, NMR, and elemental analysis.

| $R_1/R_2$ | $R_2$ | $R_4/R_5$ |
|---|---|---|
| —$CH_3$ | —H | —H, —C₆H₅ |
| —$CH_2CH_3$ | —$CH_3$ | —$CH_3$ |
| —$CF_3$ | —$CH_2CH_3$ | —$CH_2CH_3$ |
| —$(CH_2)_2CH_3$ | —$(CH_2)_2CH_3$ | —$(CH_2)_2CH_3$ |
| —$CH(CH_3)_2$ | —Cl | —$CH(CH_3)_2$ |

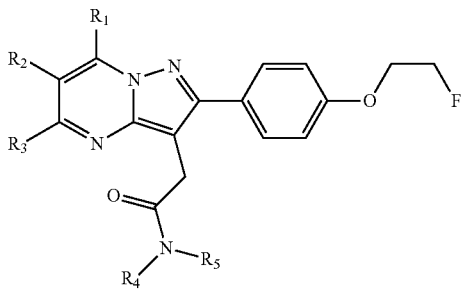

| $R_1/R_2$ | $R_2$ | $R_4/R_5$ |
|---|---|---|
| —$(CH_2)_3CH_3$ | | —$(CH_2)_3CH_3$ |
| —$CH(CH_3)_3$ | | —$CH_2OCH_3$ |

Proposed pyrazdopyrinvdines.

Example 1B

This example demonstrates synthesizing precursor/cold analogue pairs of the present invention. Ligands with high binding affinity will be chosen as lead for following probe discovery. Corresponding precursor and cold analogue can produced with suitable modification on these ligands. For example, in order to insert $^{18}F$ in to the DPA-714 scaffold, a precursor 8 with a tosyl group need to be prepared in advance (Scheme 2). With this precursor, further radiosynthesis can be performed to form [$^{18}F$]DPA-714.

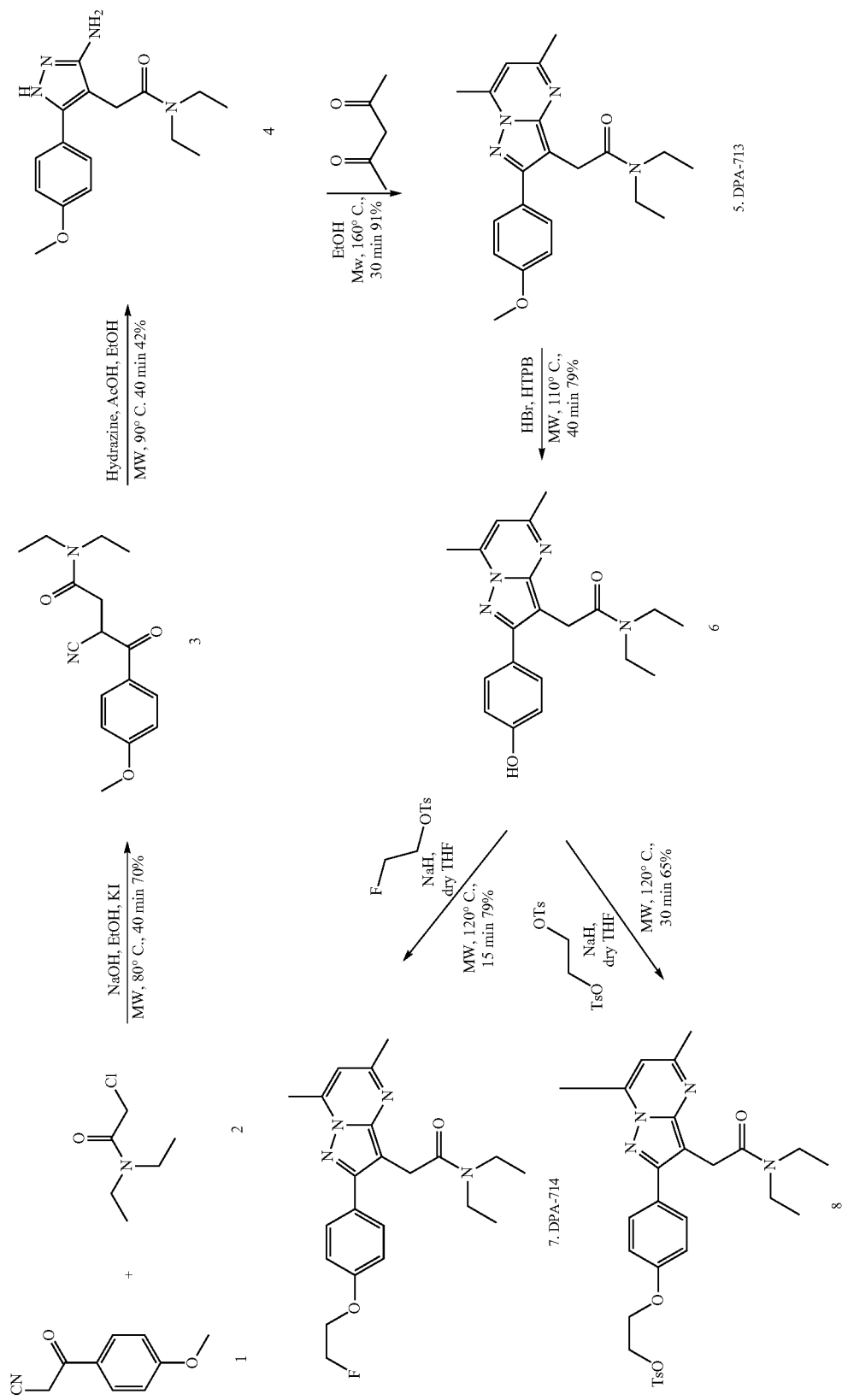
Scheme 2. Precursor and nonradioactive analogue synthesis for [18F]DPA-714

Example 1C

The tables below present further examples of the general synthetic methods used in route to novel aryloxyanilides. We will employ the methodology of Okubo et al. (Okubo, T., Yoshikawa, R., Chaki, S., Okuyama, S., Nakazato, A. "Design, synthesis and structure-affinity relationships of aryloxyanilide derivatives as novel peripheral benzodiazepine receptor ligands." Bioorganic Medicinal Chemistry 2004, 12(2), 423) with minor adaptations such as implementation of MAOS and solid-phase reagents. Synthesis of the proposed aryloxyanilides can be simplified into three primary steps: synthesis of the substituted aryloxyaniline (first table, below); reductive amination with the corresponding aldehyde; acylation with an acid halide (second table, below). We have applied these methodologies towards high-throughput synthesis of novel aryloxyanilides, as well as the synthesis of PBR06. The use of commercially available substituted 2-phenoxyanilines and aldehydes may be used, or noncommercial 2-phenoxyanilines can be generated de novo through substitution of an appropriate 2-halonitrobenzene with a hydroxyphenyl compound under basic conditions, followed by hydrogenation to the target 2-phenoxyaniline starting material.

The third table, below, presents the proposed pyrazolopyrimidines. We will utilize methodology similar to our published work featuring the pyrazolo[1,5-a]pyrimidine scaffold. Briefly, the synthesis consists of five steps, which includes consecutive pyrazole and pyrimidine ring formations. The approach enables the production of pyrazolo[1,5-a]pyrimidines with unique points of variation in the $R_1$, $R_2$, and $R_3$ positions of the pyrimidine ring and the $R_4$ and $R_5$ positions of the amide. Conveniently, the $R_1$, $R_2$, and $R_3$ positions can be varied through utilization of structurally diverse diones during pyrimidine ring formation. The $R_4$ and $R_5$ variations are achieved through use of various acetamides during pyrazole ring formation.

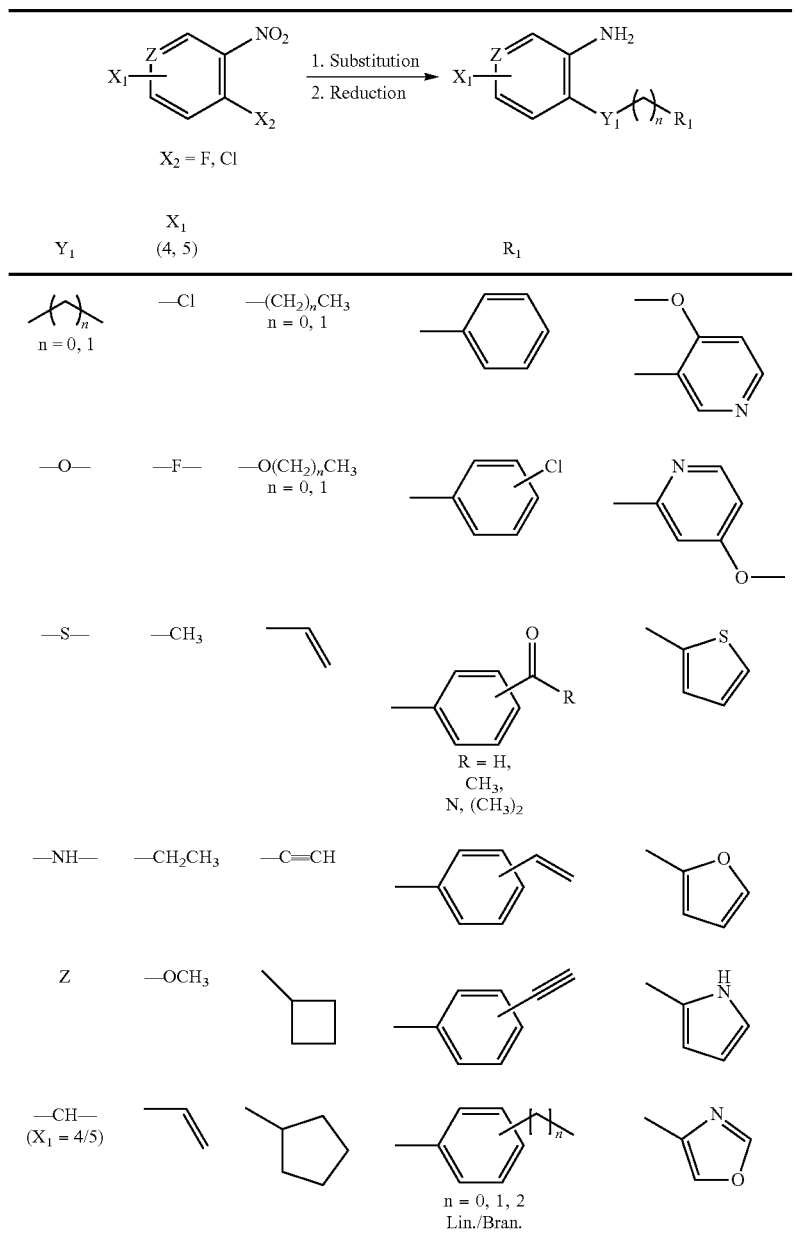

-continued
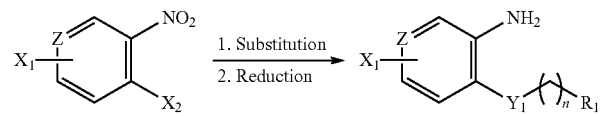
| Y₁ | X₁ (4, 5) | | R₁ | |
|---|---|---|---|---|
| —N— (X₁ = 4-sub.) | 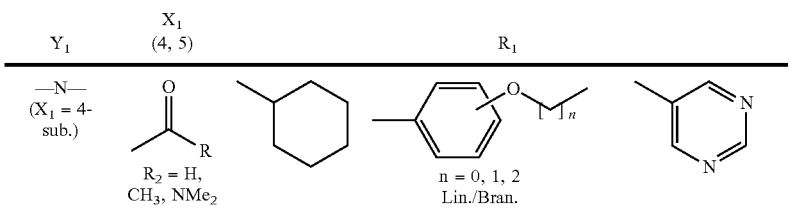 | | | |
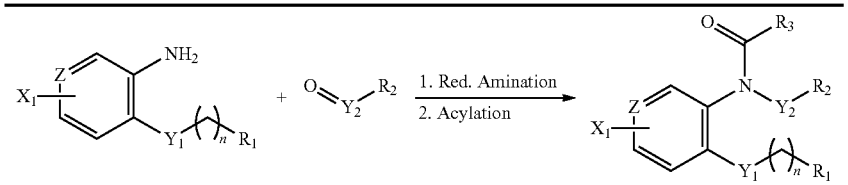
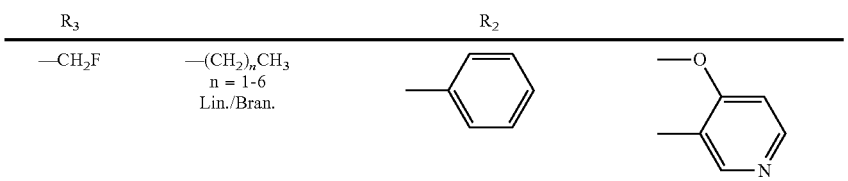
| R₃ | R₂ | | |
|---|---|---|---|
| —CH₂F | —(CH₂)ₙCH₃ n = 1-6 Lin./Bran. | 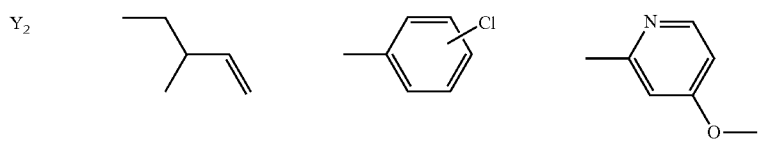 | |
| Y₂ | | | |
|---|---|---|---|
| Alkyl | 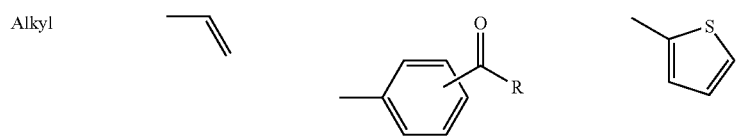 | | |
| 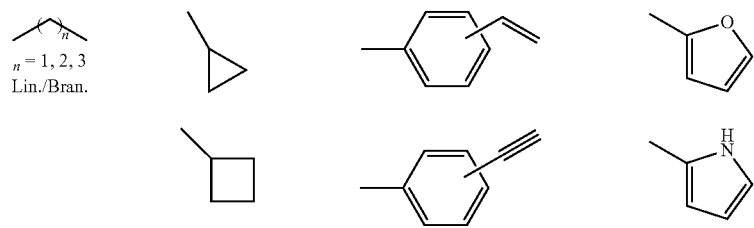 | | | |

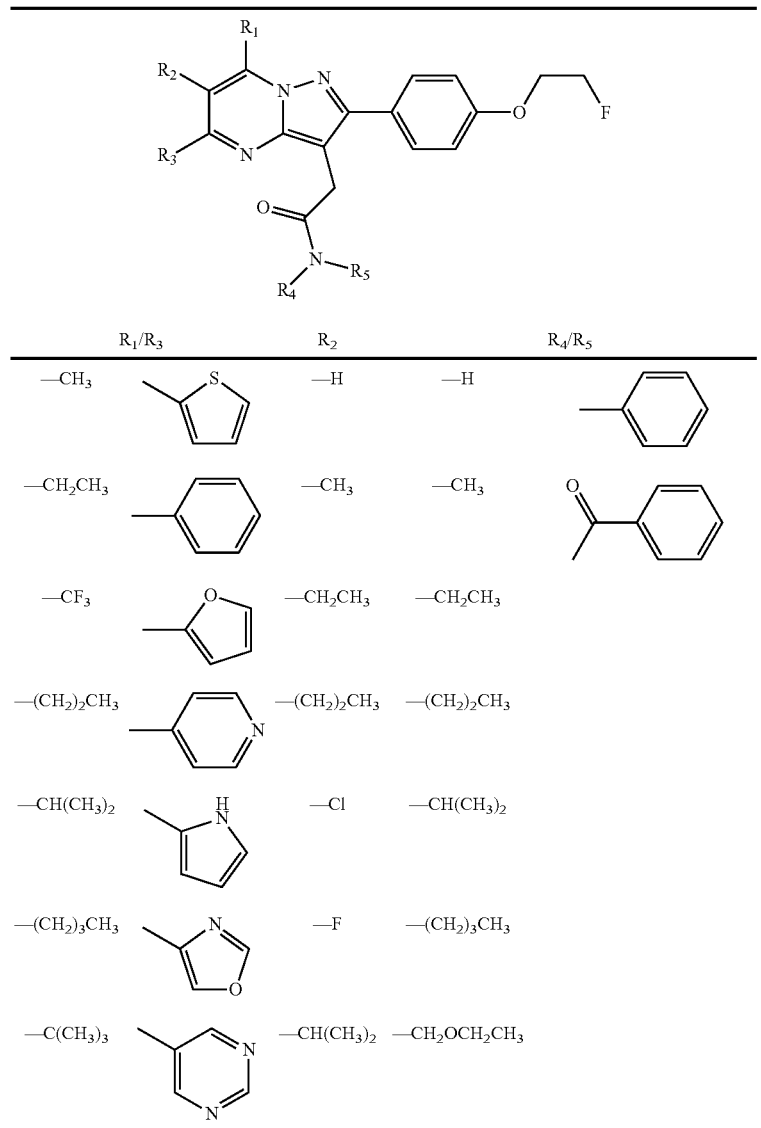

Example 2

Figure 8:
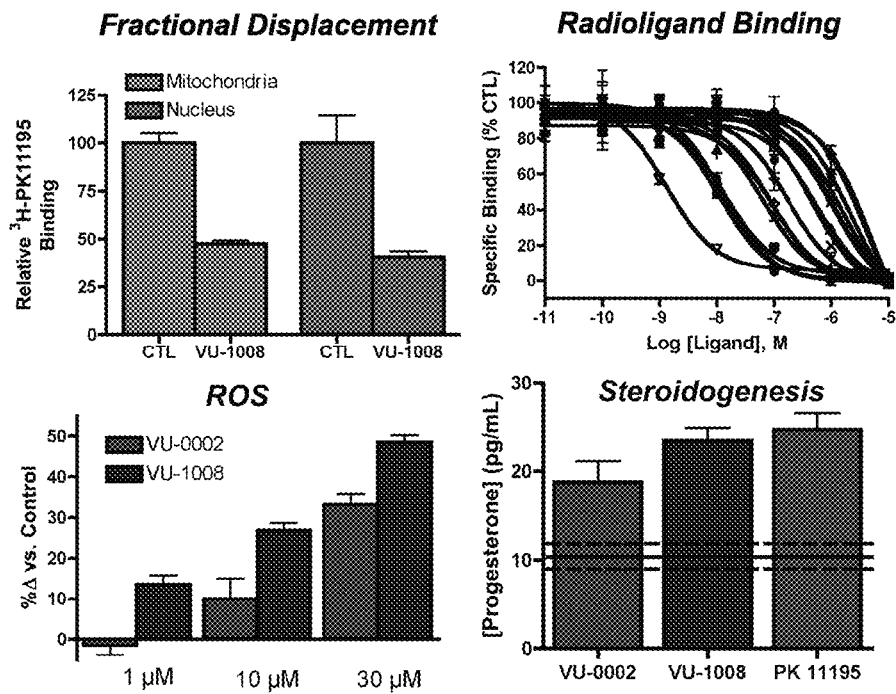
FIG. 8 shows tumor-centric' TSPO biochemical assays showing fractional radioligand displacement (mitochondria, nuclease) (top left), whole/fractional radioligand binding (top right), cellular production of reactive oxygen species (bottom left), and steroidogenesis (bottom right).

This example shows fractional displacement and radioligand binding. The characterization strategy can begin with a high-throughput fractional displacement assay developed in our laboratory (FIG. 8). This assay capitalizes upon the fact that PK 11195 binds nuclear and mitochondrial TSPO. Fractionated tumor lysate material containing an equivalent distribution of nuclear and mitochondrial TSPO (32) is incubated with [$^3$H]PK 11195 and candidate ligands. After incubation, protein is collected by centrifugation and microspotted in triplicate into high-density arrays (~1 uL). The resultant radioligand displacement of each assay is quantified using a high-resolution digital autoradiography imaging system (BiospaceLab). This assay, which boasts a throughput of >20-30 compounds/day, enables a rough, yet rapid determination of TSPO activity, as well as an estimate of the TSPO compartmentalization of novel candidates. Thus, compounds exhibiting poor binding affinity or localization are triaged prior to complicated, time consuming, and expensive assays.

Candidates exhibiting appreciable levels of fractional displacement (>75% CTL) will be subsequently advanced to traditional radioligand displacement, which provides a quantitative measure of binding affinity. Representative radioligand binding assays conducted in our laboratory are shown in FIG. 8. Given our focus of targeting TSPO expressed in tumors, affinity assays will be conducted in whole and fractionated tumor lysate. Compounds exhibiting poor TSPO affinity ($IC_{50}$>100 nM), as well as compounds with appreciable CBR activity ($IC_{50}$<500 nM), can be triaged.

Example 3

This example in intended to show a suitable procedure for labeling promising TSPO ligands with the positron-emitting isotope fluorine-18. Though we have the capability to produce carbon-11 in our Radiochemistry Core facility, the longer half-life (109.8 min) and routine availability of fluorine-18 make this isotope highly attractive for these studies. Our proposed methodologies will incorporate innovative (high-throughput, microfluidics) and traditional box-scale radiochemical techniques towards efficiently developing high-specific activity preparations.

Radiochemistry approach. Examples of novel compound development can emphasize N-fluoroacetyl aryloxyanilide and 2-phenyl-fluoroethyl pyrazolopyrimidine ether derivatives. These novel compounds can be labeled via published radiofluorination strategies that utilize bromoacetamide (aryloxyanilide) and tosylate ester (pyrazolopyrimidine) precursors. Using these approaches, we have produced high-specific activity preparations of [$^{18}$F]PBR06, [$^{18}$F]DPA-714, and novel probes [$^{18}$F]VUIIS-0005 and [$^{18}$F]VUIIS-1008.

Alternative labeling approaches. Should aliphatic fluorine-containing compounds prove to be unobtainable due to stability or reactivity concerns, a variety of analogs can be produced where the fluorine-18 label is placed on an aromatic ring. Such analogs can be labeled by nucleophilic aromatic substitution of a nitro- or trimethylammonium precursor when placed para to a suitable electron-withdrawing activating group. Labeling aromatic rings that do not possess an activating group, such as a carbonyl group, can be accomplished using diaryliodonium salt formation followed by fluoride displacement.

Figure 9:
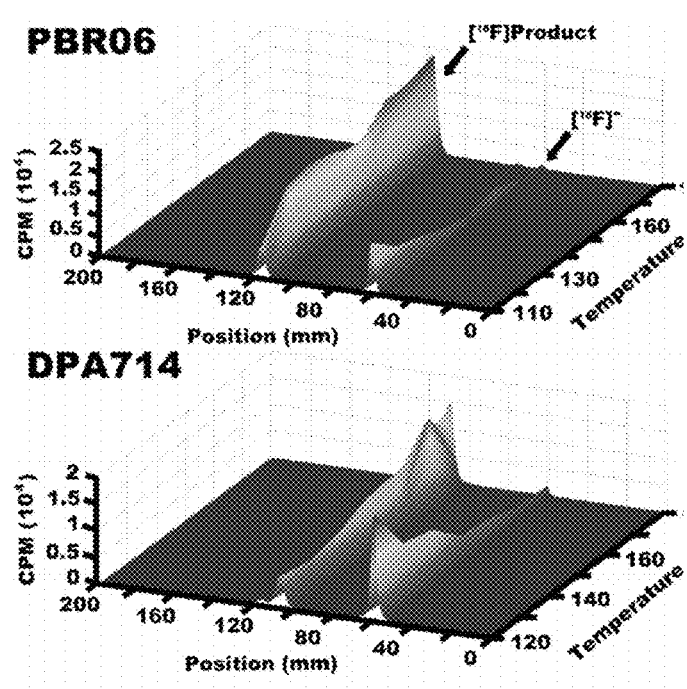
FIG. 9 shows data obtained with RadioTLC that illustrate the microfluidic production of [$^{18}$F]PBR06 and $^{18}$F-DPA-714, where the charts show [$^{18}$F]fluoride (60 mm, x-axis), product (120 mm, x-axis), and temperature (y-axis) for 20 sequential runs.

Microfluidics. The microfluidic radiolabeling approach of TSPO ligands in a Nanotek module. In preliminary studies, this approach has enabled rapid evaluation of labeling feasibility of known ([$^{18}$F]PBR06, [$^{18}$F]DPA-714) and novel compounds (FIG. 9). This approach lends itself particularly well towards establishing determinants that are time consuming by traditional box methods, including optimum solvent conditions, product/precursor stability, and validation of purification conditions.

Example 4

This example demonstrates in vivo imaging of examples of the present invention. Dynamic microPET imaging can be performed as in tumor-bearing and non-tumor-bearing rats. Briefly, rats are administered with 70-100 MBq/0.2 mL of $^{18}$F-labeled radiotracer via a jugular catheter while in a microPET Focus 220. Dynamic images (120 min) are collected, followed by CT for attenuation correction and cross-platform registration. For displacement studies, 'cold' analog (10 mg/kg) are injected via jugular catheter 30 min after radiotracer administration. Prior to PET scanning, tumors are localized in tumor-bearing rats using MRI, including $T_2$-weighted and diffusion-weighted scans. For longitudinal studies, tumor volumes are measured using a three-dimensional, $T_2$-weighted fast spin-echo sequence on a Varian 9.4 T horizontal bore imaging system.

In vivo radiometabolite analysis can be carried out to determine metabolism of $^{18}$F-labeled probes. This information is necessary for arterial input function correction in compartmental modeling studies. Radiometabolite analysis emphasizes HPLC methods similar to our published studies characterizing [$^{18}$F]PBR06 in rats. Alternately, thin-layer chromatography methodology can also be utilized as a simplified, albeit less analytically rigorous, approach. Probes demonstrating significant in vivo degradation beyond defluorination is further characterized by incubation of 'cold' analogues with commercially available rat and/or human liver microsomes supplemented with NADPH. In this way, major metabolites can be subsequently identified by a combination of LCMS, NMR spectroscopy, and independent chemical synthesis, if necessary.

A 3-compartment, 4-rate constant kinetic model can be used to characterize [$^{18}$F]PBR06 pharmacokinetics. Using COMKAT, model parameters are estimated for constants describing influx ($K_1$) and efflux ($k_2$) rates of radioligand diffusion between plasma and tissue compartments, and exchange between specific ($k_3$) and non-specific binding ($k_4$) compartments. These rate constants can be used to calculate the total volume of distribution ($V_T$) in tissues of interest. Modeling will be carried out for whole brain (excluding tumor) and tumor by fitting time-activity curves (TACs) of each region.

Example 5

This Example shows an example of quantitative, preclinical PET imaging of TSPO expression in glioma using [$^{18}$F]PBR06.

As indicated herein, translocator protein (TSPO) is an 18-kDa outer mitochondrial membrane protein involved in numerous cellular functions, including regulation of cholesterol metabolism, steroidogenesis, and apoptosis. Elevated expression of TSPO in oncology correlates with disease progression and poor survival, suggesting that molecular probes capable of assaying TSPO levels may have potential as cancer imaging biomarkers. In preclinical PET imaging studies, the present inventors have shown that [$^{18}$F]PBR06, is a probe for quantitative assessment of TSPO expression in glioma.

In this Example Glioma-bearing rats were imaged with [$^{18}$F]PBR06 in a microPET system. Dynamic acquisitions were acquired simultaneously upon injection of 70-100 MBq/0.2 mL [$^{18}$F]PBR06. Over the course of scanning, arterial blood was collected to derive the input function, with HPLC radiometabolite analysis performed on selected samples for arterial input function correction. Compartmental modeling of the PET data was performed using the corrected arterial input function. Specific tumor cell binding of PBR06 was evaluated by radioligand displacement of [$^3$H]PK 11195 with PBR06 in vitro and by displacement of [$^{18}$F]PBR06 with excess PBR06 in vivo. Immediately following imaging, tumor tissue and adjacent healthy brain were harvested for assay of TSPO protein levels by western blotting and immunohistochemistry.

[$^{18}$F]PBR06 was found to preferentially accumulate in tumors with modest uptake in contralateral brain, facilitating excellent contrast between tumor and adjacent tissue. Infusion with PBR06 (10 mg/kg) displaced [$^{18}$F]PBR06 binding by approximately 75%. The accumulation of [$^{18}$F]PBR06 in tumor tissues and adjacent brain agreed with ex vivo assay of TSPO protein levels by western blot and quantitative IHC.

This Example shows that [$^{18}$F]PBR06 is a tracer for visualization of TSPO-expressing tumors. Importantly, the close correlation between [$^{18}$F]PBR06 uptake and TSPO expression in tumor and normal tissues, coupled with the high degree of displaceable binding from both tumor and normal brain, represents a significant improvement over other TSPO imaging ligands previously evaluated in glioma. These data suggest the potential of [$^{18}$F]PBR06 to aid the elucidation of TSPO's role in oncology, as well as its potential development as a cancer imaging biomarker.

MRI was used to localize tumors. Rats were secured in a prone position in a 63 mm inner diameter radiofrequency (RF) coil and placed in a Varian 4.7 T horizontal bore imaging system (Varian Inc., Palo Alto, Calif.). A constant body temperature of 37° C. was maintained using heated air flow. An initial multislice gradient echo imaging sequence [repetition time (TR)=150 ms; echo time (TE)=3.5 ms; 128×128 matrix, 40×40 mm$^2$ FOV; 2 mm slice thickness] was used to acquire seven slices in each imaging plane (axial, coronal, sagittal) for proper positioning of subsequent scans. A multislice $T_2$-weighted fast-spin echo scan with 8 echoes and 8.6 ms echo spacing was then collected with TR=2000 ms, 32×32 mm$^2$ FOV, 128×128 matrix, number of acquisitions=16, and 8 coronal slices of 2 mm thickness. The same anatomical slices were then imaged at the same FOV and resolution using a diffusion-weighted spin echo sequence [TR=2000 ms; TE=35.4 ms; number of acquisitions=8; δ=4 ms; Δ=25 ms] at b-values of 0 and 600 s/mm$^2$.

PET/CT imaging was performed within 24 h of MR imaging in rats with confirmed tumors. Tumor-bearing rats were administered ~70-100 MBq/0.2 mL [$^{18}$F]PBR06 via a jugular catheter while in a microPET Focus 220 (Siemens Preclinical Solutions, Knoxville, Tenn., USA). Dynamic images (90 min) were collected, followed by CT (microCAT II, Siemens Preclinical Solutions) for attenuation correction. For displacement studies, cold PBR06 (10 mg/kg) was injected via jugular catheter 30 min after radiotracer administration.

The dynamic PET acquisition was divided into twelve, five-second frames for the first minute, followed by 89 sixty-second frames for the duration of the scan. Data from all possible lines of response (LOR) were saved in the list mode raw data format. The raw data was then binned into 3D sinograms with a span of 3 and ring difference of 47. The images were reconstructed into transaxial slices (128×128× 95) with voxel sizes of 0.095×0.095×0.08 cm$^3$, after applying scatter and attenuation corrections, using an iterative ordered subsets expectation maximization (OS-EM 2D) algorithm with 16 subsets and 4 iterations. Attenuation correction was accomplished by generating an attenuation map (sinogram) from the CT image. The CT image was first co-registered with the microPET image, segmented into air, soft tissue, and bone, and then projected into sinograms with a span of 47 and ring difference of 23.

Immediately following administration of [$^{18}$F]PBR06, arterial blood samples (50 μL) were collected at 10 s intervals during the first minute of scanning, followed by collection at 90 s and 2, 8, 12, 20, 30, 45, 60, 75, and 90 min. Plasma radioactivity was measured by first centrifuging blood samples (50 μL) at 14,000 rpm for 5 min in a microcentrifuge. Next, plasma (15 μL) was removed and measured in a NaI well counter (Capintec, Ramsey, N.J., USA).

Blood samples (200 μL) were collected (2, 25, 45 min) for radiometabolite analysis. Following centrifugation, plasma was extracted with acetonitrile:water (340 μL, 7.5:1, v/v). The mixture was centrifuged and the supernatant used for HPLC analysis. Radioanalysis was conducted as is known in the art. Radiochromatographic data were recorded and collected using a radioisotope detector (Bioscan, Washington, D.C., USA), decay-corrected to time zero of each radiochromatogram, and smoothed using a locally weighted scatter plot smoothing (LOWESS) method. The plasma time-activity curve (TAC) was corrected with the fraction of unchanged radioligand.

Whole brains were harvested and fixed in 4% formalin for 48 h, followed by paraffin embedding. For immunohistochemistry (IHC), tissues were collected and sectioned (5.0 μm thickness). TSPO immunoreactivity was assessed using a TSPO-specific rabbit polyclonal antibody that was a gift from Professor V. Papadopoulos of McGill University, Montreal, Canada. Immunoreactivity was assessed using a HRP Detection Kit (Dako, Glostrup, Denmark). For histology quantification, optical density measurements of multi-spectral image cubes were collected using a CRI Nuance camera and the total intensity of positive pixels determined.

For western blotting, protein (50 μg) from each sample was loaded into 10% gels and resolved by electrophoresis prior to transferring to polyvinylidene fluoride membranes. Membranes were blocked in tris-buffered saline 0.1% Tween-20 (TBST) containing 5% w/v milk. Membranes were immunoblotted with TSPO antibody. Probing occurred overnight at 4° C., (1:1,000 in TBST with 5% milk), followed by incubation for 1 h at RT with HRP secondary antibody (1:4000 in TBST with 5% milk). Chemiluminescence (ECLplus; GE Healthcare-Biosciences, Piscataway, N.J., USA) was used for protein detection.

Time-activity curves (TACs) were generated by manually segmenting three-dimensional volumes of interest over tumor and contralateral brain using ASIPro (Siemens Preclinical Solutions), avoiding areas of central necrosis if present. The arterial input function (AIF) was computed from plasma sampling during imaging and corrected for metabolism of the parent ligand. A 3-compartment, 4-rate constant kinetic model was used to characterize [$^{18}$F]PBR06 pharmacokinetics as previously described. Using the COMKAT software package, model parameters were estimated for constants for influx ($K_1$) and efflux ($k_2$) rates of radioligand diffusion between plasma and tissue compartments, and exchange between specific ($k_3$) and non-specific binding ($k_4$) compartments. Modeling was carried out for whole brain (excluding tumor) and tumor, individually, by fitting TACs of each region. In addition, using the first 60 min of data (beyond which, tracer was undetectable in blood), a graphical analysis method was used to estimate the total distribution volume (VT) for the whole brain (excluding tumor) and tumor, with goodness of fit evaluated by inspection.

Figure 10:
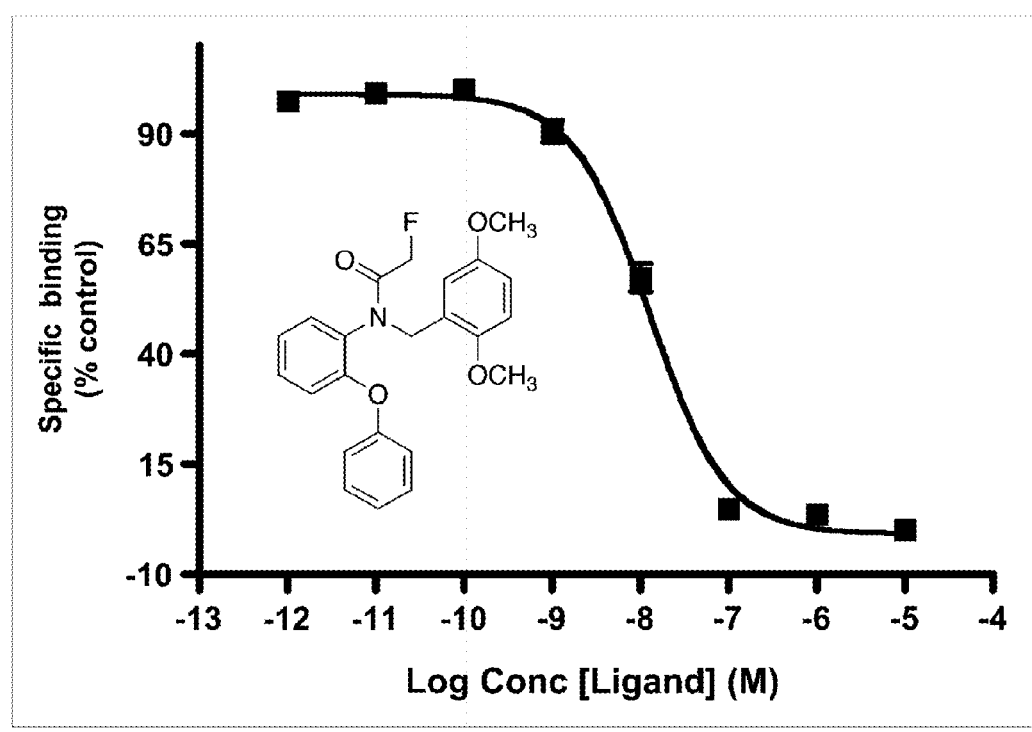
FIG. 10 shows the radioligand displacement of [$^3$H]PK 11195 using PBR06 in C6 glioma cell lysate (calculated $IC_{50=12}$ nM). Inset is the chemical structure of PBR06. Error bars denote percentage standard deviation corresponding to triplicate measurements.

Radioligand displacement of the high-affinity isoquinoline carboxamide TSPO ligand [$^3$H]PK 11195 was used to evaluate the specific binding of the non-radioactive analogue PBR06 in C6 glioma cell line homogenates in vitro (FIG. 10). In the example, PBR06 was highly specific for TSPO in C6 cell homogenates, exhibiting dose-dependent displacement of [$^3$H]PK 11195 to near-background levels. Non-linear regression analysis of the binding data yielded an $IC_{50}$ for PBR06 of approximately 12.6 nM in repeated studies.

Figure 2:
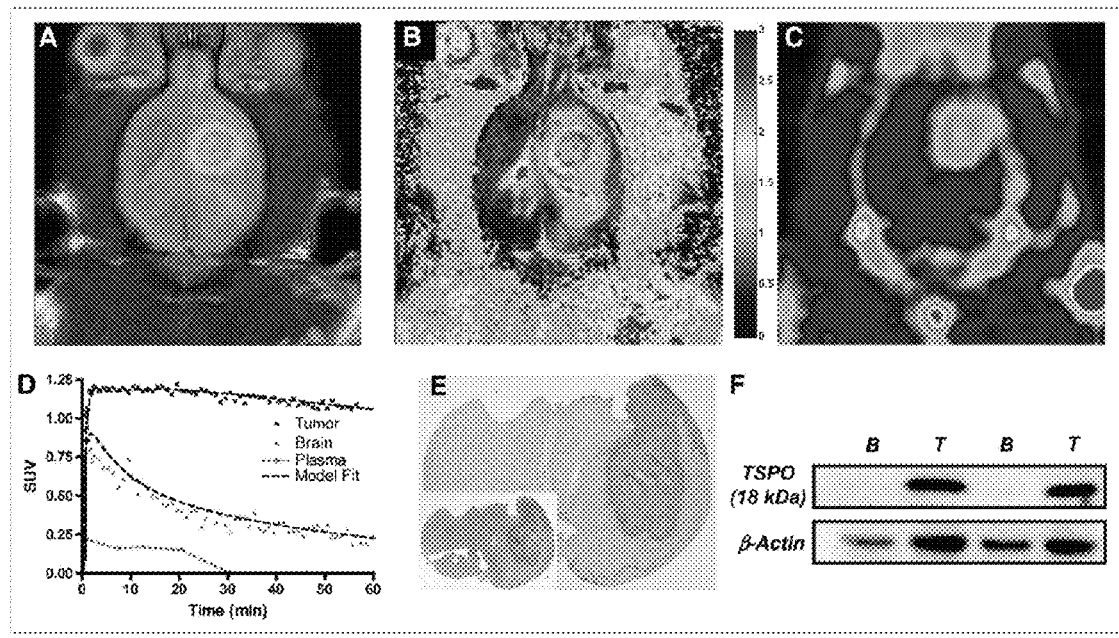
FIG. 2 shows $^{18}F$-PBR06 used to assess TSPO in C6 glioma. (A) and (B) show, respectively, $T_2$-weighted and diffusion-weighted MR images of a C6 glioma-bearing rat (the bar in the right-side of image (B) corresponds to units of diffusion in $\mu m^2/ms$). (C) Shows a PET image showing elevated uptake of $^{18}F$-PBR0 6 in tumor tissues compared to contralateral brain (summed dynamic scan 0-90 min). (D) Shows [$^{18}F$]PBR06 time-activity curves and model fit (three-compartment, four-parameter) for tumor (blue/square), contralateral brain (green/triangle), and plasma (red/circle-dashed), which demonstrate rapid tracer uptake in tumor and normal brain, followed by rapid clearance from plasma and normal tissue. Comparatively slow washout of [$^{18}F$]PBR06 was observed in tumor tissues, facilitating significant contrast between tumor and contralateral brain. (E) Shows serial histological analysis of a C6 glioma by standard hematoxylin and eosin (H&E) staining (inset) and immunohistochemistry for TSPO expression illustrating elevated TSPO expression within tumor tissue compared to contralateral brain. (F) Shows a western blot illustrating relative TSPO protein expression levels in matched contralateral brain tissue (B) and C6 glioma (7) tissues harvested from similar C6 glioma-bearing rat cohorts.
Figure 3:
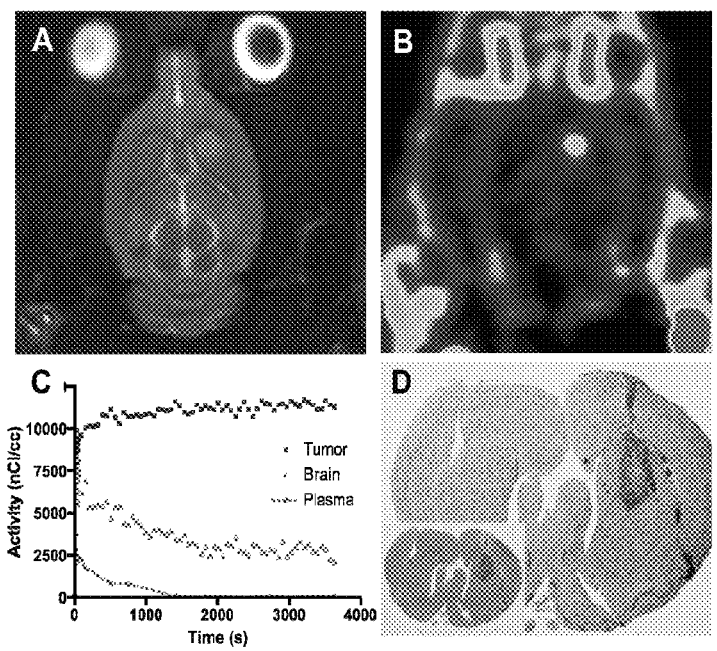
FIG. 3 shows [$^{18}F$]DPA-714 used to assess TSPO in C6 glioma. (A) Shows a $T_2$-weighted MRI of a C6 glioma-bearing rat. (B) Shows a PET image showing elevated uptake of [$^{18}F$]DPA-714 in tumor tissues and very modest uptake in contralateral brain. (C) Shows [$^{18}F$]DPA-714 time-activity curves for tumor (blue/square), contralateral brain (green/triangle), and plasma (red/circle-dashed). (D) Shows serial histological analysis of imaging-matched C6 glioma by standard H&E staining (inset) and immunohistochemistry for TSPO expression.

Prior to PET imaging, tumor-bearing animals were subjected to $T_2$-weighted and diffusion-weighted MRI performed at 4.7 T. In these studies, C6 tumors exhibited marked hyperintensity throughout the majority of the tumor, indicative of longer $T_2$ relaxation times compared to surrounding brain (white matter). Furthermore, a portion of the tumors examined exhibited central core regions characterized by shorter $T_2$ values compared to more peripheral regions (FIG. 2A). Tissues demonstrating long $T_2$ also exhibited increased diffusion consistent with edema typical of the C6 model (FIG. 2B). Dynamic PET imaging of [$^{18}$F]PBR06 illustrated that the majority of the uptake in the brain was localized to tumor tissue, with only minor uptake in adjacent normal areas of the brain (FIG. 2C). Total radioactivity levels in tumor tissue were approximately three- to four-fold higher than normal brain when compared over the last 20 minutes of the PET scan. We observed minor radioactivity in the skull that appeared to be consistent with $^{18}$F$^-$ uptake, as well as activity that appeared to be consistent with the olfactory epithelium. Across all animals studied, we found that tumor uptake tended to be slightly higher in more peripheral regions of the tumor, presumably consistent with the regions of highest proliferation and infiltrative disease. Some tumors imaged over the course of these studies exhibited modest levels of central necrosis, similar to that shown in FIG. 2. Within these tumor regions, only modest tracer uptake was observed. FIG. 2D illustrates a TAC for whole tumor, normal brain, and plasma activity for a typical 90 minute scan. We found that [$^{18}$F]PBR06 washed into both normal brain and tumor tissue rapidly, but the washout from tumor tissue was much slower compared to normal brain. Following the initial spike in the plasma activity consistent with tracer injection, [$^{18}$F]PBR06 rapidly cleared from plasma. Immediately following imaging, brains were harvested and processed for subsequent staining and IHC. Using standard H&E staining to localize the tumor (FIG. 2E inset), we found that TSPO immunoreactivity was significantly higher in the tumor than in normal brain (FIG. 2E).

Consistent with previous studies of TSPO expression in glioma, TSPO protein levels measured by IHC optical density were approximately 3.3-fold higher in tumor relative to normal brain tissue. Analogous to the accumulation of [$^{18}$F]PBR06, TSPO expression within the tumor appeared to be somewhat higher nearer the tumor periphery (FIG. 2E), suggesting higher TSPO density in areas of active tumor proliferation. As further confirmation of the TSPO expression density in the tumor compared to the contralateral brain, western blot analysis was performed on resected tumor tissue and contralateral normal brain. Similar to the IHC studies, analysis of the relative TSPO immunoreactivity (18 kDa band) from multiple subjects demonstrated that TSPO levels were approximately three-fold higher in the tumor relative to the contralateral brain tissue (FIG. 2F). Importantly, excellent agreement was observed between [$^{18}$F]PBR06 accumulation and TSPO protein levels measured by both IHC and western blot.

Figure 11:
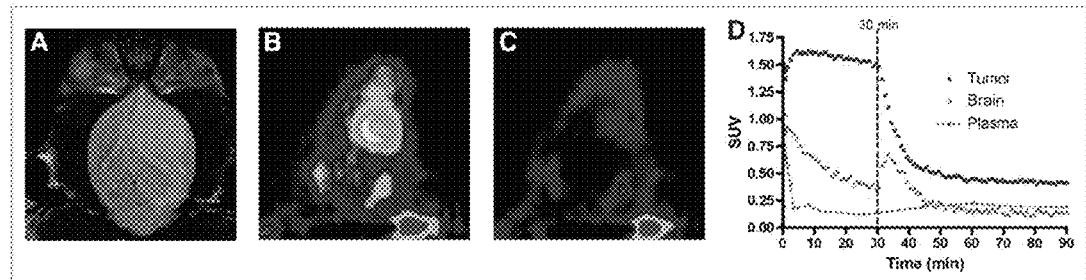
FIG. 11 shows in vivo displacement of [$^{18}$F]PBR06 in a C6 glioma-bearing rat. (A) Shows a $T_2$-weighted MR image of rat bearing a C6 glioma in the right brain hemisphere. (B) and (C) show PET images of relative [$^{18}$F]PBR06 uptake before and after intravenous infusion of excess PBR06, respectively. (D) Shows [$^{18}$F]PBR06 time-activity curves generated for tumor (blue/square), contralateral brain (green/triangle), and plasma (red/circle-dashed), illustrating that immediately following infusion of [$^{18}$F]PBR06 tumor activity drops to approximately 25% of the maximum uptake level, accompanied by a minor, transient tracer influx observed in the contralateral brain and elevated plasma activity. The data are representative of repeated imaging studies.

To evaluate the in vivo TSPO specificity of [$^{18}$F]PBR06, we carried out displacement studies in C6-bearing rats using the cold analog, PBR06. As shown in FIG. 11, during the dynamic PET study, excess (10 mg/kg) PBR06 was administered intravenously, 30 minutes following injection of [$^{18}$F]PBR06. Summation of the first 30 minutes of the PET scan prior to injection of PBR06 (0-30 min) demonstrated typical uptake characteristics of [$^{18}$F]PBR06 (FIG. 11B). However, summation of the final 30 minutes of the PET scan (60-90 min) demonstrated significant displacement of [$^{18}$F]PBR06 in normal brain and tumor tissue (FIG. 11C). Accordingly, TAC analysis (FIG. 11D) demonstrated that following injection of PBR06, tumor activity was reduced to approximately 25% of the peak tumor uptake. During tumor displacement, we observed a minor influx of tracer into normal brain that rapidly cleared, as well as elevated radioactivity in the plasma. In further studies, an additional injection of excess cold ligand, 45 minutes following [$^{18}$F]PBR06 injection, did not result in additional displacement of the radiotracer (data not shown), suggesting that the level of displaceable binding in these studies was approximately 75%.

Figure 12:
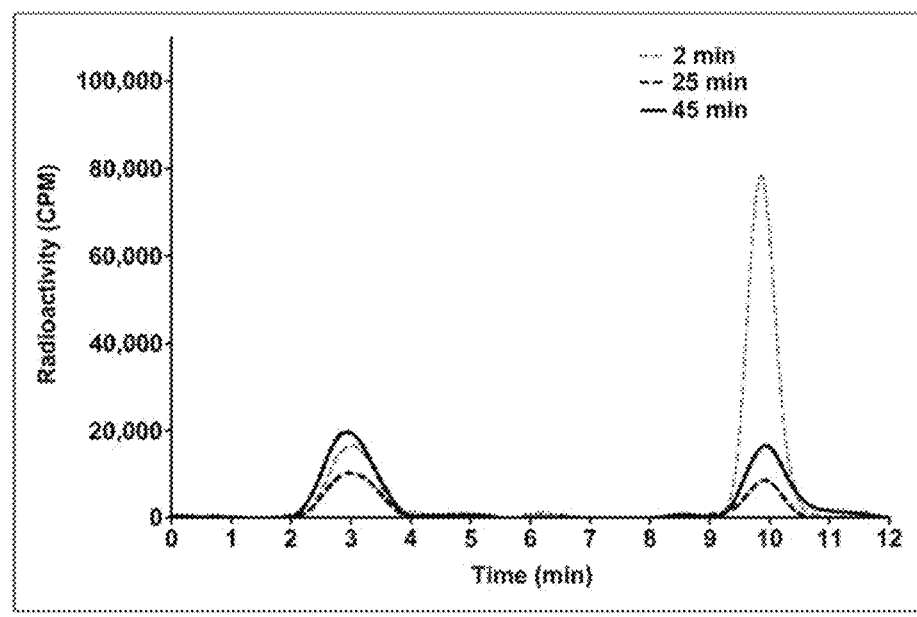
FIG. 12 shows HPLC radiochromatograms illustrating plasma composition of the parent ligand ([$^{18}$F]PBR06) and the primary radiometabolite $^{18}$F$^-$ as a function of time following tracer injection. The dashed gray line represents 2 minutes after injection with [$^{18}$F]PBR06, the dashed black line represents 25 after injection with [$^{18}$F]PBR06, and solid black line represents 25 after injection with [$^{18}$F]PBR06 and 15 minutes after cold PBR06 injection. At 2 and 25 minutes following injection of [$^{18}$F]PBR06, free $^{18}$F$^-$ (25% at 2.8 minutes, 62% at 30 minutes) and parent ligand (75% at 2.8 minutes, 38% at 30 minutes) are detectable in plasma. Following infusion of PBR06 30 minutes after administration of [$^{18}$F]PBR06, both the fraction of [$^{18}$F]PBR06 (57% at 45 minutes) and $^{18}$F$^-$ (43% at 45 minutes) were elevated in the plasma.

Arterial blood samples were collected to assay [$^{18}$F]PBR06 radiometabolites for correction of the AIF. FIG. 12 illustrates a typical activity corrected reversed-phase HPLC trace of a blood sample collected two minutes following injection of [$^{18}$F]PBR06. At this time point we noted the presence of both $^{18}$F$^-$ (retention time 2.8 min) and the parent ligand (10.1 min) in a respective ratio of ~1:3. Analogously, 25-30 min blood samples routinely demonstrated significantly decreased plasma levels of parent ligand and slightly decreased levels of $^{18}$F$^-$. In contrast to human studies using [$^{18}$F]PBR06, we did not observe additional radiometabolites during these studies. Plasma analysis of samples following displacement of [$^{18}$F]PBR06 with PBR06 exhibited elevated levels of both parent ligand and $^{18}$F$^-$, suggesting that tracer metabolism in this model is a plasma-specific event.

Previous human studies have demonstrated good fitting of [$^{18}$F]PBR06 imaging data to a 3-compartment, 4-kinetic parameter model for quantitative analysis in brain tissues. Utilizing this model and the metabolite-corrected AIF, $K_1$, $k_2$, $k_3$, and $k_4$ were solved for tumor tissue and normal brain (See the table, below).

| | Parameter estimations for [$^{18}$F]PBR06 uptake (mean ± S.E.). | | | |
|---|---|---|---|---|
| | $K_1/k_2$ (mL/g)* | $k_3$ (min$^{-1}$)* | $k_4$ (min$^{-1}$)* | $V_T$ (mL/g)†, |
| Tumor | 5.947 ± 1.982 | 0.3870 ± 0.1592 | 5.510E$^{-8}$ ± 5.501E$^{-8}$ | 63.90 ± 3.400 |

| | Parameter estimations for [$^{18}$F]PBR06 uptake (mean ± S.E.). | | | |
|---|---|---|---|---|
| | $K_1/k_2$ (mL/g)* | $k_3$ (min$^{-1}$)* | $k_4$ (min$^{-1}$)* | $V_T$ (mL/g)†, |
| Brain | 6.164 ± 2.049 | 0.0714 ± 0.0261 | 0.009450 ± 0.005532 | 13.07 ± 3.901 |
| P value | 0.9429 | 0.1221 | 0.1628 | 0.0006 |

N = 3*, 4†

Figure 13:
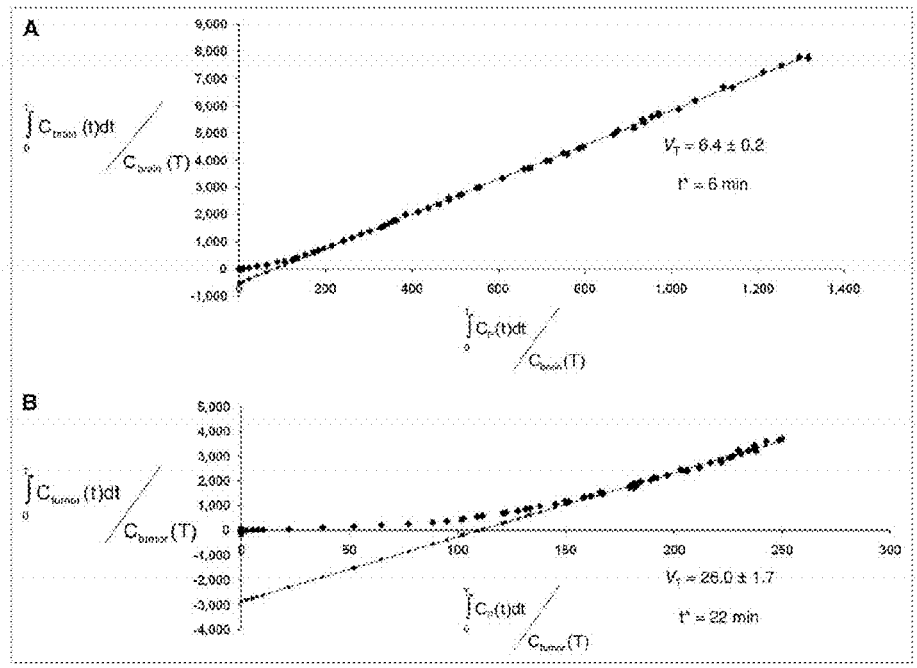
FIG. 13 shows a graphical analysis of the total distribution volume (VT) of one of the subjects studied. The fit was carried out for normal brain (A) and for tumor (B). The solid grey line is a linear regression of the data, and t* represents the start time for the linear regression. $C_{brain}(t)$, $C_p(t)$, and $C_{tumor}(t)$ represent the concentration of radiotracer at time (t) in, respectively, the brain, plasma, and tumor.

We noted good agreement for measured parameters in normal brain, particularly $k_3$ and $k_4$, when comparing our rat studies to values previously determined in non-human primates. Similarly, though studies describing direct estimation of parameters in tumor tissue using [$^{18}$F]PBR06 are unreported, it appeared that direct parameter estimation was possible in tumor tissue. Unlike normal brain, however, tumor tissues tended to exhibit $k_4$ values approaching zero. The very low $k_4$ values resulted in estimations of $V_T$ from tumor-derived parameters that were not supported by direct measures of TSPO density (IHC, WB). In contrast, graphical estimation of $V_T$, which does not depend upon direct measurement of $k_4$, yielded statistically significant values that closely mirrored TSPO expression levels in tumor compared to normal brain (FIG. 13(A-B)).

Example 6

This Example shows DPA-714 as a translational probe for quantification of TSPO levels in glioma.

In this example, glioma-bearing rats were imaged with [$^{18}$F]DPA-714 in a microPET system. Dynamic images were acquired simultaneously upon injection of [$^{18}$F]DPA-714 (70-100 MBq/0.2 mL). Arterial blood was collected to derive the input function (AIF), with HPLC radiometabolite analysis performed on selected samples for AIF correction. Compartmental modeling was performed using the corrected AIF. Specific tumor cell binding of DPA-714 was evaluated by radioligand displacement of [$^3$H]PK 11195 with DPA-714 in vitro and displacement of [$^{18}$F]DPA-714 with excess DPA-714 in vivo. Immediately following imaging, tumor and healthy brain tissues were harvested for validation by western blotting and immunohistochemistry.

[$^{18}$F]DPA-714 was found to preferentially accumulate in tumors with modest uptake in contralateral brain. Infusion with DPA-714 (10 mg/kg) displaced [$^{18}$F]DPA-714 binding by approximately 75%. Tumor uptake of [$^{18}$F]DPA-714 was similar to another high-affinity TSPO imaging ligand, [$^{18}$F]PBR06, and agreed with ex vivo assay of TSPO protein levels in tumor and healthy brain.

This example and others in connection with the present invention show the use of [$^{18}$F]DPA-714 for visualization of TSPO-expressing brain tumors. Additionally, it is shown that [$^{18}$F]DPA-714 is suitable for quantitative assay of tumor TSPO levels in vivo. Given the relationship between elevated TSPO levels and poor outcome in oncology, these studies suggest the potential of [$^{18}$F]DPA-714 PET to serve as a novel predictive cancer imaging modality. [$^{18}$F]DPA-714 was prepared analogously to published methods. In short, using a commercial apparatus (TRACERlab FXF-N, GE Medical Systems), aqueous [$^{18}$F]fluoride ion (~111 GBq) was dried by iterative cycles of addition and evaporation of acetonitrile, followed by complexation with K$^+$-K$^{+-2.2.2}$/K$_2$CO$_3$. The complex was reacted with 4-(3-(2-(diethylamino)-2-oxoethyl)-5,7-dimethylpyrazolo[1,5-a]pyrimidin-2-yl)phenethyl 4-methylbenzenesulfonate (3.0 mg) at 165° C. for 5 min in dimethyl sulfoxide (0.6 mL). Purification of [$^{18}$F]DPA-714 was carried out using reversed-phase HPLC (C18, Dynamax 250×21.4 mm; Varian) eluted at 6.0 mL/min with 10 mM $NaH_2PO_4$ buffer (pH 6.70) and ethanol (47.5:52.5; v/v). [$^{18}$F]DPA-714 was collected, washed with 120 mL water (deionized), and eluted from a C18 Sep-Pak with ethanol (1.0 mL) into a sterile flask loaded with saline (9.0 mL). Typical specific activities were ≥418 TBq/mmol.

MRI was used to localize the C6 tumors.

PET/CT imaging was performed within 24 h of MR imaging in rats with confirmed tumors.

Immediately following administration of [$^{18}$F]DPA-714, arterial blood samples (50 µL) were collected at 10-s intervals during the first minute of scanning, followed by collection at 90 s, and 2, 8, 12, 20, 30, 45, 60, 75, and 90 min. Blood samples (50 µL) were centrifuged at 14,000 RPM for 5 min in a microcentrifuge. The plasma (15 µL) was then removed and the radioactivity measured in a NaI well counter (Capintec).

Briefly, arterial blood (200 µL) was collected at 2, 12, 30, 60, and 90 min. Following centrifugation, plasma was extracted with acetonitrile:water (340 µL, 7:1, v/v). The mixture was centrifuged and the supernatant used for reversed phase HPLC analysis using 0.1 M aqueous ammonium acetate ($NH_4$)OAc (pH 10) and acetonitrile (30:70; v/v) at 1 mL/min on a C18 Dynamax 250×4.6 mm (Varian) column. Radiochromatographic data were recorded and collected using a radioisotope detector (Bioscan), decay-corrected to time zero of each radiochromatogram, and smoothed using a locally weighted scatter plot smoothing method. The plasma time-activity curve was corrected according to the fraction of unchanged radioligand.

Whole brains were harvested and fixed in 4% formalin for 48 h, followed by paraffin embedding for immunohistochemistry (IHC). Tissue sections of 5.0 µm thickness were taken and TSPO immunoreactivity was assessed using a TSPO-specific rabbit polyclonal antibody. Immunoreactivity was assessed using an HRP Detection Kit (Dako). Hematoxylin and eosin (H&E) staining was used to quantify cell density and tumor localization. For histology quantification, optical density measurements of multi-spectral image cubes were collected using a CRI Nuance camera and the total intensity of positive pixels was determined as reported previously.

Time-activity curves (TACs) were generated by manually drawing three-dimensional volumes of interest over tumor and contralateral brain using ASIPro (Siemens). The arterial input function (AIF) was computed from plasma sampling during imaging and corrected for metabolism of the parent ligand. Both a 2-compartment, 2-rate constant kinetic model and a 3-compartment, O-rate constant kinetic model were used to characterize [$^{18}$F]DPA-714 pharmacokinetics with COMKAT software package. In the 2-compartment, g-rate constant kinetic model, we determined model parameters for the influx ($K_1$) and efflux ($k_2$), rate constants of the radioligand diffusion between the plasma and tissue compartments. In the 3-compartment, 4-rate constant kinetic model, we determined model parameters for influx ($K_1$) and efflux ($k_2$) and exchange constants between specific binding ($k_3$) and free ligand (including non-specific binding) ($k_4$) compartments for both normal brain tissue and tumor. For the 3-compartment, 4-rate constant kinetic model, the total volume of distribution (VT) was then calculated using the equation $V_T=(K_1/k_2)(1+k_3/k_4)$ for the whole brain (excluding tumor) and for the tumor. Additionally, using the first 60 minutes of data (beyond which, tracer was undetectable in blood), a graphical analysis method was used to estimate the total distribution volume for the whole brain (excluding tumor) and tumor.

Figure 14:
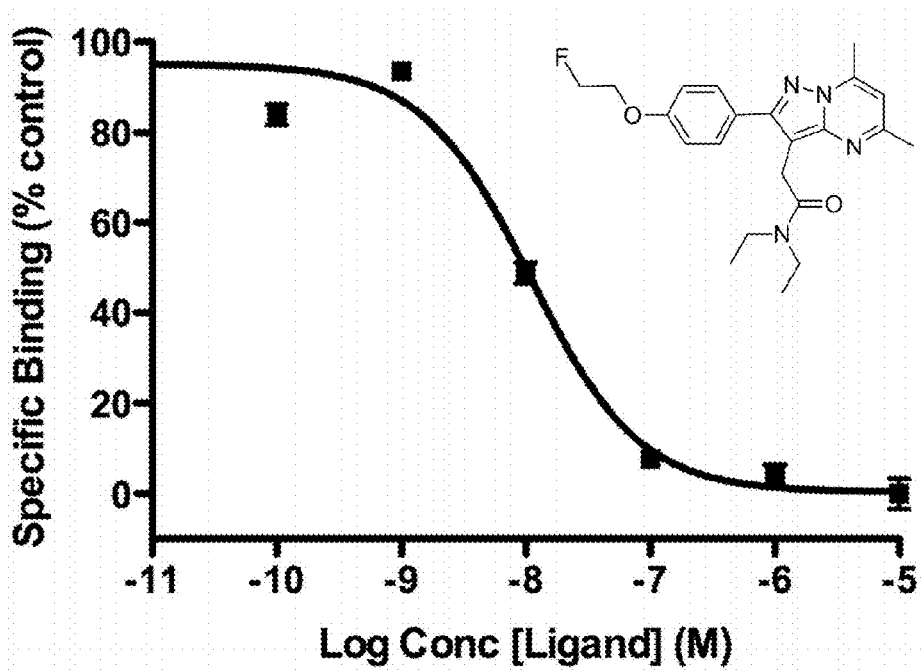
FIG. 14 shows the radioligand displacement of [$^3$H]PK 11195 using DPA-714 in C6 glioma cell lysate (calculated $IC_{50}$=10.9 nM). Inset is the chemical structure of DPA-714.

Previous studies explored [$^{18}$F]DPA-714 within the context of neuroinflammation. Our interest in assaying TSPO expression in glioma led us to evaluate the specific binding of DPA-714 in glioma cell line homogenates (FIG. 14). We found DPA-714 to be highly specific for TSPO, exhibiting dose-dependent displacement of the isoquinoline carboxamide [$^3$H]PK 11195 to near-background levels. Non-linear regression analysis of the binding data yielded an $IC_{50}$ for DPA-714 of approximately 10.9 nM, similar to our previous observations with the aryloxyanilide PBR06.

Figure 15:
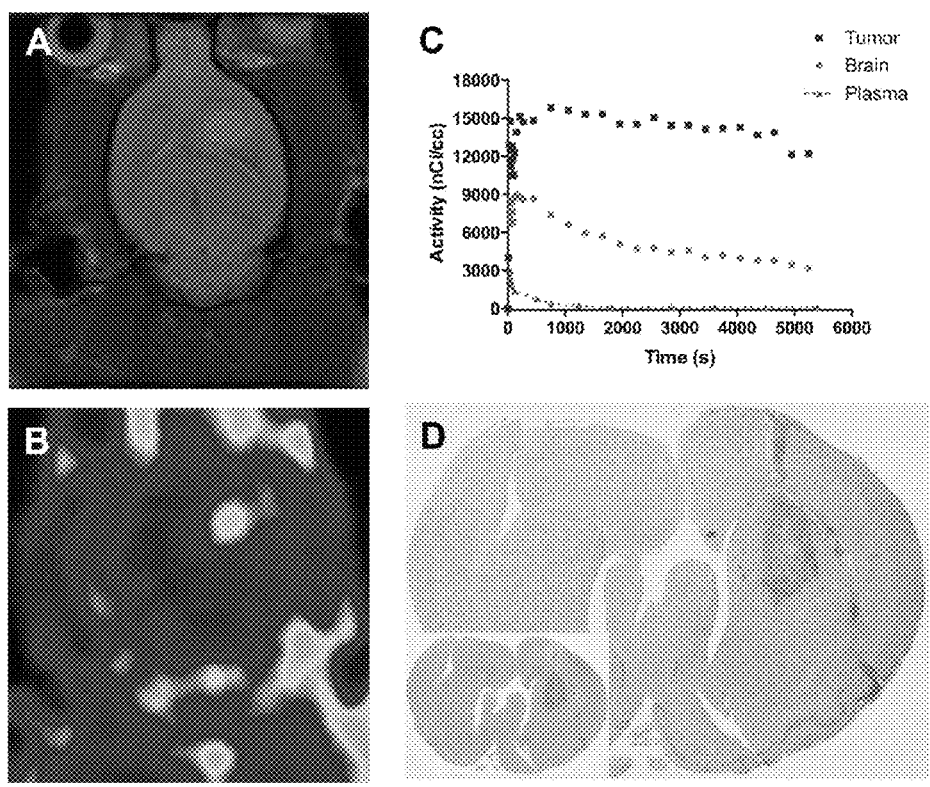
FIG. 15 shows (A) a $T_2$-weighted MR image of a rat bearing a C6 glioma in the right hemisphere, (B) a PET image obtained from a dynamic scan of [$^{18}$F]DPA-714 PET (summed dynamic scan, 0-90 min), (C) [$^{18}$F]DPA-714 time-activity curves for tumor (blue/square), brain (green/circle), and plasma (red/triangle-dashed), and (D) an immunohistochemical analysis of TSPO expression in C6 glioma, and inset a standard H&E staining of a serial tissue section.
Figure 21:
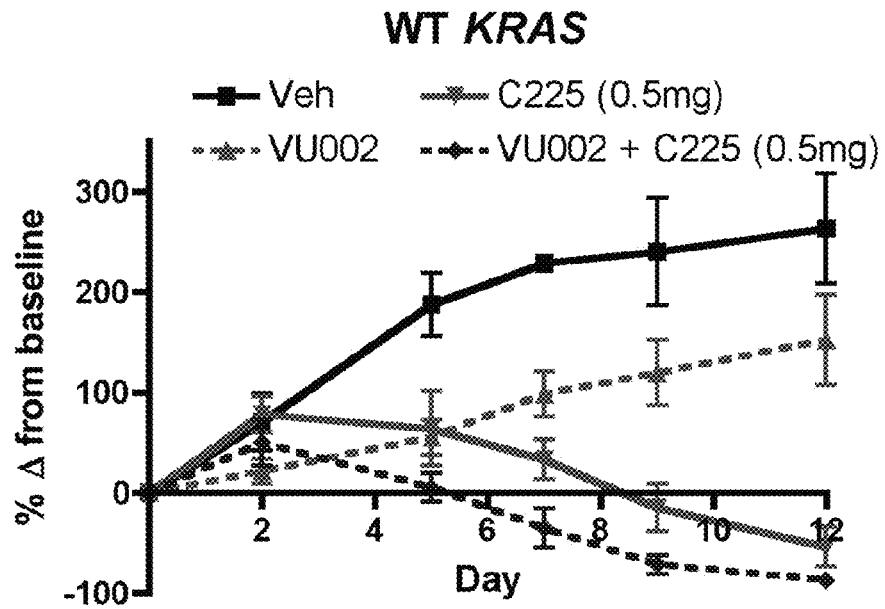
FIGS. 21-23 are graphs demonstrating the synergistic effect of administering compounds of the present invention with known cancer drugs.

Prior to PET imaging with [$^{18}$F]DPA-714, brain tumors were localized using $T_2$-weighted MRI. Similar to our previous observations, C6 tumors exhibited marked hyperintensity indicative of longer $T_2$ relaxation times compared to surrounding brain (FIG. 15A). Dynamic PET imaging of [$^{18}$F]DPA-714 illustrated that the majority of the uptake in the brain was localized to tumor tissue, with only modest accumulation in adjacent, normal areas of the brain (FIG. 15B). Over the last 20 minutes of the PET scan, total radioactivity levels in tumor tissue were approximately four-fold higher than normal brain. Over the course of imaging, a modest level of radioactivity localized to the skull, indicating defluorination that was later confirmed by HPLC radiometabolite analysis. Minor accumulation of [$^{18}$F]DPA-714 was observed in the olfactory epithelium and Harderian glands, which had little impact on brain tumor imaging. FIG. 15C illustrates a typical TAC for tumor, normal brain, and plasma activity for a typical 90 minute scan. We found that [$^{18}$F]DPA-714 washed into both normal brain and tumor tissue rapidly, but washout from tumor tissue was much slower compared to normal brain. Following the initial spike in plasma activity consistent with tracer injection, [$^{18}$F]DPA-714 rapidly cleared from plasma. Imaging-matched brains were processed for staining and IHC. Using standard H&E staining to localize the tumor (FIG. 15D inset), we found that TSPO immunoreactivity was significantly higher in the tumor than in normal brain (FIG. 21D). Consistent with previous studies of TSPO expression in glioma, TSPO protein levels measured by IHC optical density were three- to four-fold higher in tumor relative to normal brain tissue. Overall, we found excellent agreement between [$^{18}$F]DPA-714 accumulation and TSPO protein levels as measured by IHC.

Figure 16:
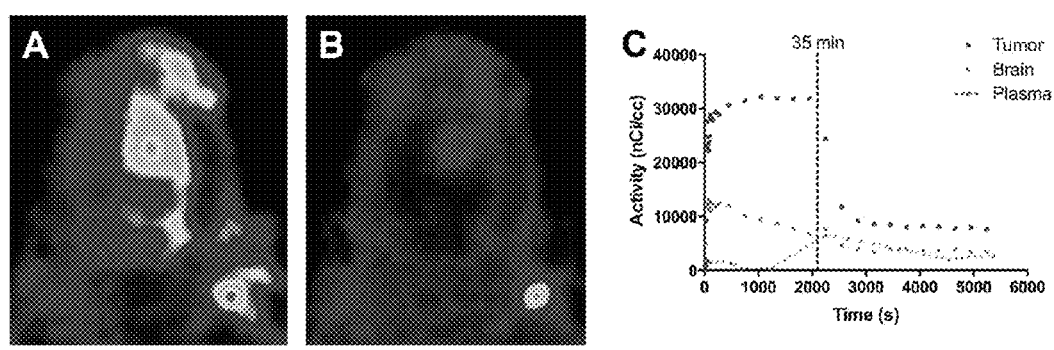
FIG. 16 shows in vivo displacement of [$^{18}$F]DPA-714 in a C6 glioma-bearing rat. (A) and (B) show PET images of relative [$^{18}$F]DPA-714 uptake before and after intravenous infusion of excess DPA-714, respectively. (C) shows [$^{18}$F]DPA-714 time-activity curves generated for tumor (blue/square), brain (green/circle), and plasma (red/circle-dashed).

To evaluate the in vivo TSPO specificity of [$^{18}$F]DPA-714, we carried out displacement studies in C6-bearing rats using DPA-714. During the dynamic PET study, excess (10 mg/kg) DPA-714 was administered intravenously, 30 minutes following injection of [$^{18}$F]DPA-714. Summation of the first 30 minutes of the PET scan prior to injection of DPA-714 (0-30 min) demonstrated typical uptake characteristics of [$^{18}$F]DPA-714 (FIG. 16A). However, summation of the final 30 minutes of the PET scan (60-90 min) demonstrated significant displacement of [$^{18}$F]DPA-714 in normal brain and tumor tissue (FIG. 16B). Accordingly, TAC analysis (FIG. 16C) demonstrated that following injection of DPA-714, tumor activity was reduced by approximately 75% of the peak tumor uptake. Interestingly, the minor fraction of non-displaceable tumor activity from the study shown appeared to be associated with an area of central necrosis.

Figure 17:
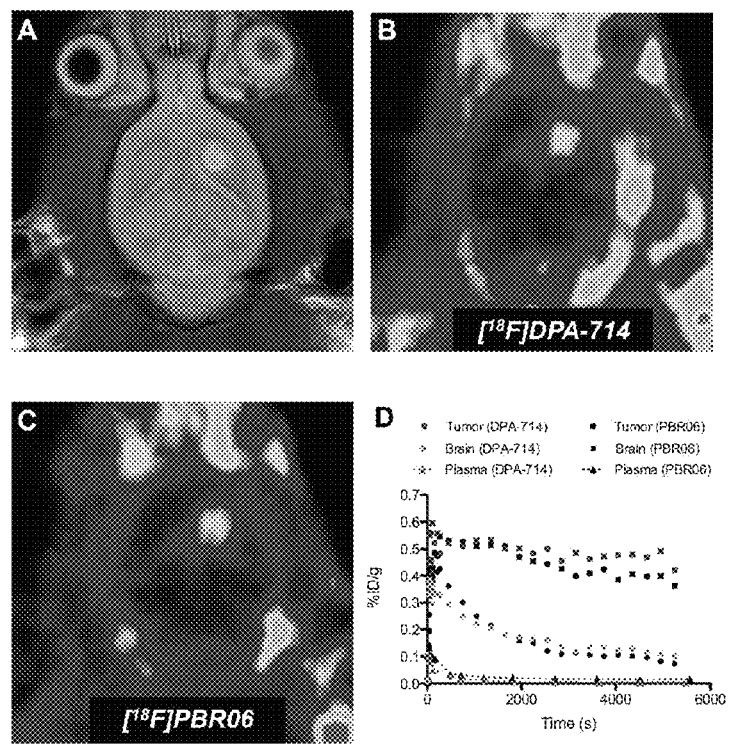
FIG. 17 shows a comparison of [$^{18}$F]PBR06 and [$^{18}$F]DPA-714 in the same glioma-bearing rat. (A) Shows a $T_2$-weighted MR image of a rat bearing C6 glioma in the right hemisphere. (B) and (C) show, respectively, a [$^{18}$F]PBR06 image and a [$^{18}$F]DPA-714 image (both summed dynamic scan over the last 30 minutes). (D) Shows [$^{18}$F]DPA-714 time-activity curves generated for tumor (blue/square), contralateral brain (green/circle), plasma (red/triangle-dashed) as well as corresponding [$^{18}$F]PBR06 time-activity curves shown in black.

To further evaluate the in vivo performance of [$^{18}$F]DPA-714 in tumor studies, we compared the localization and relative tissue uptake of this tracer to an aryloxyanilide TSPO PET ligand, [$^{18}$F]PBR06 directly in C6 glioma-bearing cohorts. A representative study is shown in FIG. 17. Tumors were initially localized with $T_2$-weighted MRI (FIG. 17A). Subsequently, serial dynamic PET imaging studies utilizing [$^{18}$F]PBR06 (FIG. 17B) or [$^{18}$F]DPA-714 (FIG. 17C) were carried out approximately 24 hours apart. As shown in FIG. 17, both tracers exhibited similar localization to tumor tissue, with only modest retention in the normal brain. Both tracers exhibited similarly rapid clearance from plasma and normal brain. However, TAC analysis illustrated that [$^{18}$F]DPA-714 was retained in tumor tissue to a somewhat greater extent than [$^{18}$F]PBR06, which manifested as a modestly higher signal-to-noise ratio (tumor/normal) for [$^{18}$F]DPA-714 over the last 30 minutes of the PET scan.

Detectable [$^{18}$F]DPA-714 radiometabolites included free [$^{18}$F]fluoride (retention time 2.5 min) and a single radiometabolite more hydrophilic than DPA-714 (retention time 4.0 min, parent tracer retention time 5.0 min). As shown in Table 1, immediately following intravenous injection of [$^{18}$F]DPA-714, the parent tracer accounted for approximately 95% of the whole plasma radioactivity. Over the scan duration, the proportion of parent ligand in plasma diminished at a rate roughly proportional to apparent defluorination. Levels of the observed hydrophilic radiometabolite were relatively constant beyond the first 10 minutes of the scan, suggesting that appearance of this species was offset by further metabolism and/or subsequent clearance.

Figure 18:
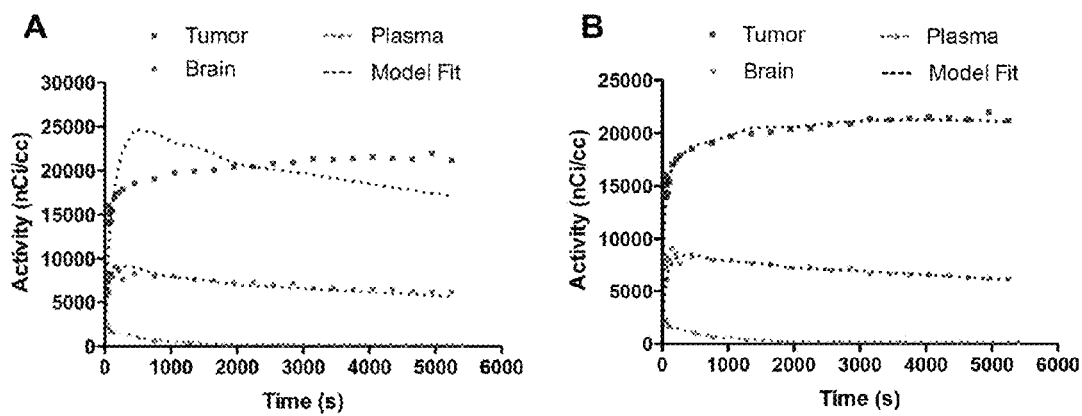
FIG. 18 shows a pharmacokinetic model fit of [$^{18}$F]DPA-714 time-activity curves to (A) a 2-compartment, 2-kinetic parameter model, and (B) a 3-compartment, 4-kinetic parameter model. Time-activity curves for tumor (blue/square), brain (green/circle), and plasma (red/triangle-dashed) are shown with the associated model fit.
Figure 19:
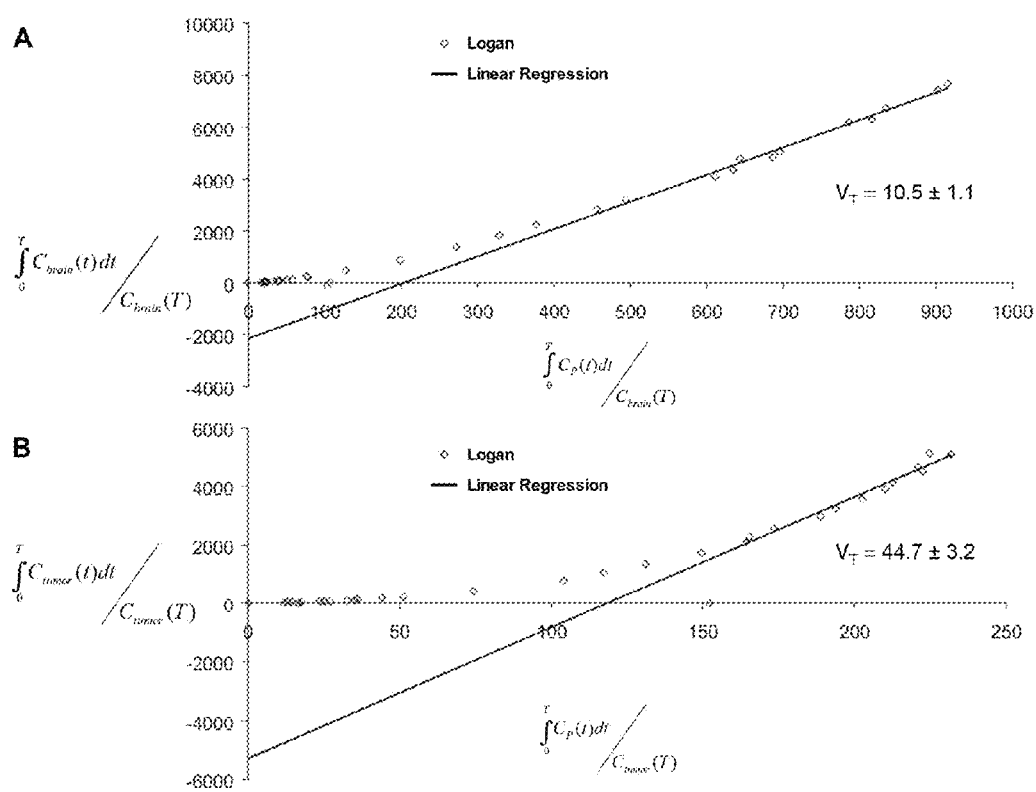
FIG. 19 shows a graphical analysis of the total distribution volume (VT) of one of the subjects studied. The fit was carried out for normal brain (A) and for tumor (B). The solid grey line is a linear regression of the data. $C_{brain}(t)$, $C_p(t)$, and $C_{tumor}(t)$ represent the concentration of radiotracer at time (t) in, respectively, the brain, plasma, and tumor.

To describe the pharmacokinetics of [$^{18}$F]DPA-714, we evaluated a 2-compartment, 2-kinetic parameter and a 3-compartment, 4-kinetic parameter model. The kinetic modeling results demonstrated that the 3-compartment, 4-kinetic parameter model fits the experimental data better than the 2-compartment, 2-kinetic parameter model (FIG. 18(A-B). Utilizing this 3-compartment, 4-kinetic parameter model and the metabolite-corrected AIF, $K_1/k_2$ and $k_3/k_4$ were determined for the tumor tissue and normal brain (Table 2). Similarly, though studies describing direct estimation of parameters in tumor tissue using [$^{18}$F]DPA-714 are unreported, it appeared that direct parameter estimation was possible in tumor tissue. Compared with normal brain, tumor tissues tended to exhibit a higher $K_1/k_2$ and $k_3/k_4$ (Table 2). Estimation of $V_T$ contrast based on kinetic parameters and graphical estimation (FIG. 19) of $V_T$ was performed both in brain and tumor. The ratios of $V_T$ between tumor and brain from these two estimations were identical to each and yielded statistically significant values that closely mirrored TSPO expression (Table 2).

TABLE 1

HPLC Radiometabolite Analysis of [$^{18}$F]DPA-714 (mean ± SD).

| P.I. Time | % [$^{18}$F]DPA-714 | % $^{18}$F- | % Metabolite |
|---|---|---|---|
| 2 (N = 7) | 95 ± 6.0 | 2 ± 3.3 | 3 ± 3.7 |
| 12 (N = 7) | 68 ± 7.4 | 13 ± 6.7 | 19 ± 5.8 |
| 30 (N = 7) | 44 ± 8.9 | 37 ± 5.4 | 19 ± 8.8 |
| 60 (N = 7) | 27 ± 6.2 | 50 ± 15.0 | 23 ± 7.3 |
| 90 (N = 5) | 22 ± 17.8 | 64 ± 12.1 | 14 ± 3.8 |

TABLE 2

Parameter Estimations for [$^{18}$F]DPA-714 Uptake (mean ± S.E.).

| | $K_1/k_2$ (mL/g) | $k_3/k_4$ | $V_T$ (mL/g)† | $V_T$ (mL/g)‡ |
|---|---|---|---|---|
| Tumor (N = 11) | 6.867 ± 1.226 | 8.913 ± 1.155 | 70.033 ± 14.729 | 57.440 ± 11.742 |
| Brain (N = 11) | 3.619 ± 0.551 | 4.024 ± 0.842 | 15.963 ± 3.566 | 14.570 ± 2.823 |
| P value | 0.0762 | 0.0021 | 0.0017 | 0.0029 |

From kinetic parameters†.
From graphical analysis‡.

In summary, this example shows the use of a compound of the present invention for visualization of TSPO-expressing brain tumors, and its suitability for quantitative assaying of tumor TSPO levels in vivo. Given the relationship between elevated TSPO levels and poor outcome in oncology, these studies suggest the potential of compounds of the present invention to serve as a novel predictive cancer imaging modality.

Example 7

Figure 20:
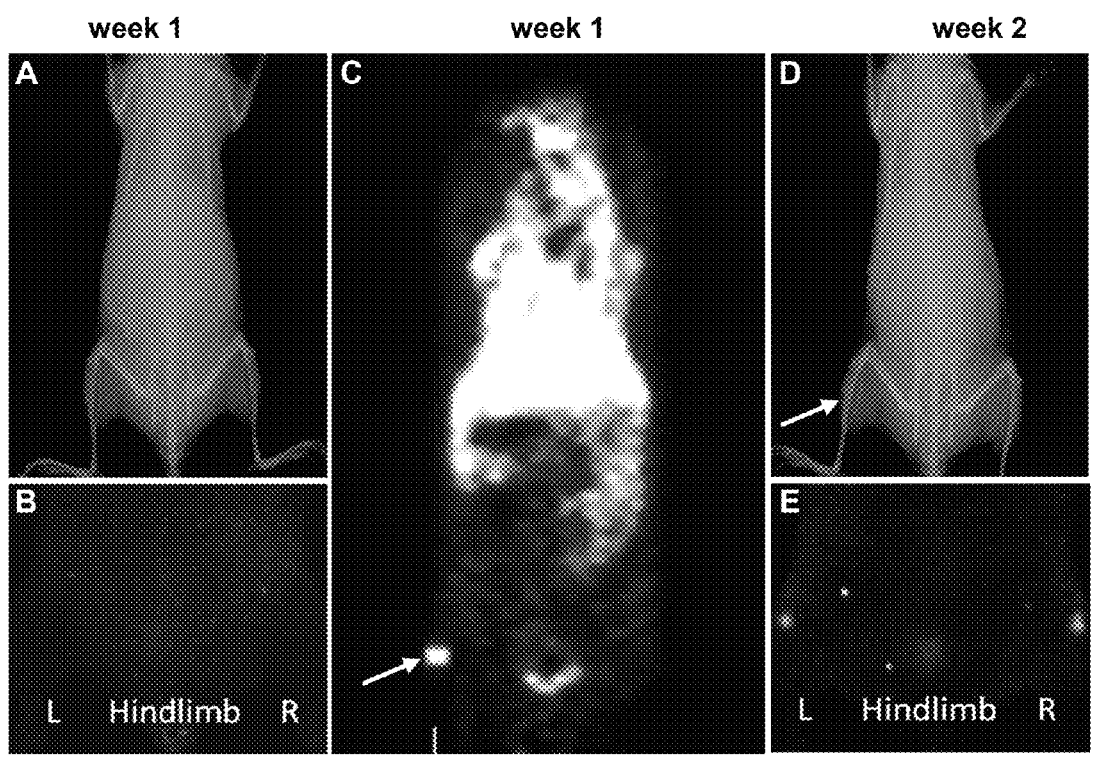
FIG. 20 shows TSPO imaging detects tumors in bone lwk before detection by Faxitron or fluorescence. A) Faxitron B) Maestro images 2 weeks after tumor cell inoculation, with no detectable lesions. C) Clearly visible lesion detected in the L-tibia by TSPO-PET imaging at week 2. D) Faxitron E) Maestro image of the same mouse 1 week later (3 weeks after tumor cell inoculation), showing small lesions. Additionally, TSPO imaging was able to detect lesions in sites that are difficult to detect by fluorescence/Faxitron, such as the forelimbs.

Example 7 shows the biodistribution and tumor uptake of an 18F-labeled aryloxyanilide-based TSPO ligand ([18F] VUIIS-1018) in a nude mouse one week following intracardiac (IC) injection of MDA-MB-231 cells. Lesions are clearly visible 1 week prior to detection by faxitron analysis (bone loss) and GFP (tumor) cells. FIG. 20 shows TSPO imaging detects tumors in bone 1 wk before detection by Faxitron or Fluorescence. A) Faxitron B) Maestro images 2 weeks after tumor cell inoculation, with no detectable lesions. C) Clearly visible lesion detected in the L-tibia by TSPO-PET imaging at week 2. D) Faxitron E) Maestro image of the same mouse 1 week later (3 weeks after tumor cell inoculation), showing small lesions. Additionally, TSPO imaging was able to detect lesions in sites that are difficult to detect by fluorescence/faxitron, such as the forelimbs.

Example 8

Therapy

Figure 22:
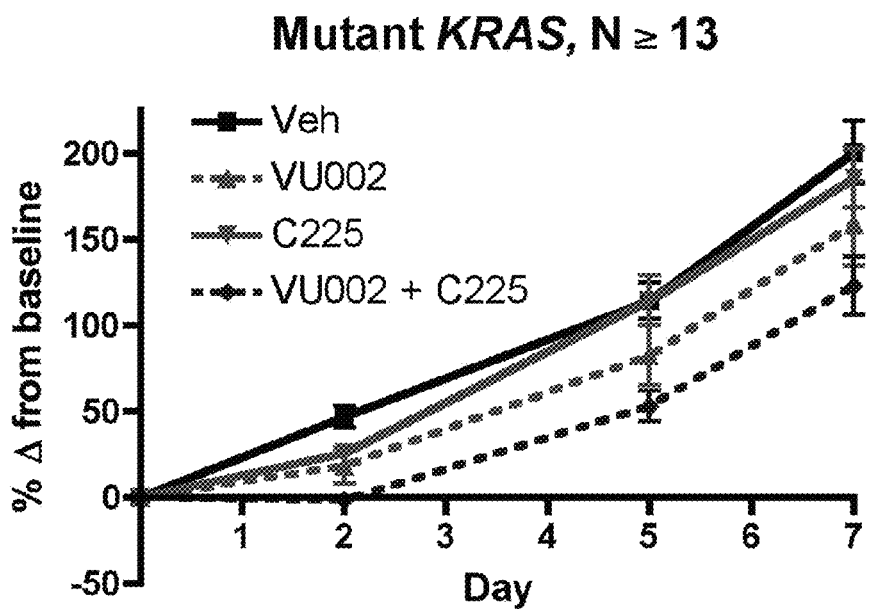

This example shows a TSPO ligand of the present invention, PBR06, demonstrating an in vivo synergistic effect with a known epidermal growth factor receptor (EGFR) inhibitor, Cetuximab, enhancing therapeutic efficacy. This synergism is shown with both wild type (WT) and mutant KRAS colorectal cancer (CRC) cohorts (mice). We also show that the TSPO ligand is well tolerated among the test subjects and that complimentary pathway inhibition is a superior and unexpected route of therapy. See FIGS. 21 and 22.

Example 9

Figure 23:
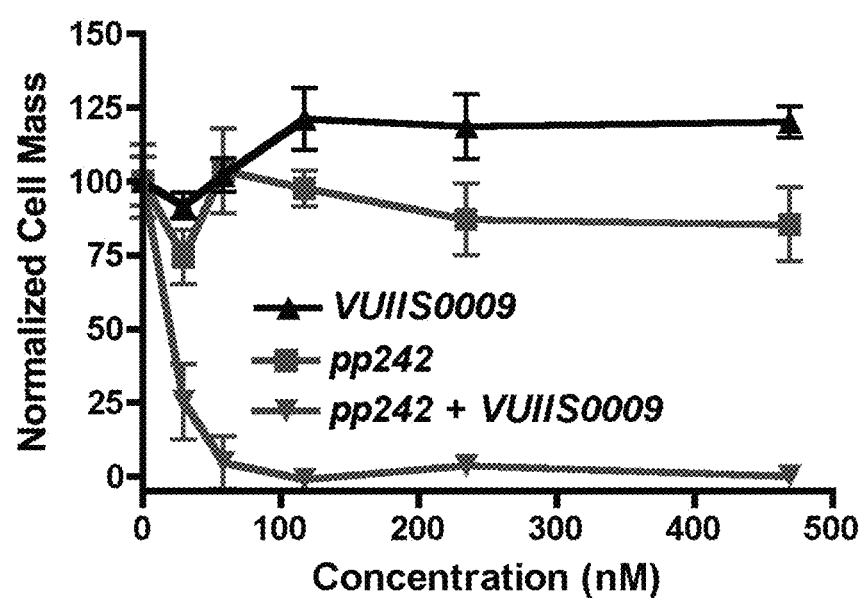

This example shows a TSPO ligand of the present invention, VUIIS0009, demonstrating an in vitro synergistic effect with a known mammalian target of rapamycin (mTOR) inhibitor pp242. This synergism is shown in HCT-116 colorectal cancer (CRC) cells bearing KRAS and PIK3CA mutations. See FIG. 23.

Example 10

This Example shows that TSPO compounds of the present invention enhance C225 efficacy in a WT KRAS CRC cell line.

The data show treatment of DiFi human CRC cells in vitro with C225, a TSPO ligand (PBR06, VUIIS-0001), or the combination of these agents. (PBR06 concentrations=0, 10 nm+, 100 nM++, 1 µM+++, 10 uM++++; C225 concentrations=0.5 µg/mL+, 5.0 µg/mL++). In these studies, cultured cells were exposed to drug for 24 hr, harvested, and the protein levels of various markers were assayed by immunoblotting. In single agent dose escalation studies we found that increasing concentrations of PBR06 induced modestly elevated levels of pERK. A suboptimal dose of C225 (+) was found to be in sufficient to yield pERK inhibition, but a 10× higher dosage (++) fully inhibited pERK levels. As determined by cleaved caspase 3 levels, apoptosis was induced by the elevated dosage of C225 (++) only. As a measure of cell cycle arrest, p27 levels were found to increase in a concentration-dependant fashion following treatment with PBR06, resulting in significantly elevated p27 following treatment with only 10 nM PBR06. Levels of p27 were also modestly elevated by the lower dosage of C225 (+) and proportionately higher in the highest dosage of C225 (++). Consistent with activation of cAMP signaling stemming from the production and cell utilization of progesterone, we found pPKA elevated following treatment with the TSPO ligand. The lower dosage of C225 also appeared to induce pPKA to some extent.

Combinations of C225 and the TSPO were more effective at inducing cell cycle arrest and apoptosis than either single agent alone. In combining the lowest dosage of C225, which was ineffective as a single agent, with the all dosages of PBR06 evaluated, we found that significantly elevated levels of p27 could be achieved indicating cell cycle arrest. This assay was complemented by the observation of diminished cyclin D1 levels concomitant with elevated p27, indicating growth factor and effective cell cycle withdrawal. The fact that p27 levels were elevated, in conjunction with diminished cyclin D1, in spite of elevated pERK levels with combinations of low-dose C225 and PBR06 suggests that pERK has translocated from the nucleus, its primary oncogenic intracellular location, to the mitochondria to facilitate TSPO-mediated cholesterol metabolism. In cellular fractionation studies utilizing these conditions (10C, below), we found pERK to be localized at the mitochondria in levels proportional to the overall intracellular activation shown in 10B, below. Importantly, when pERK is present at the mitchondria it appears to no longer serve as an oncogene, rendering C225 more effective in DiFi cells. In addition to the cell cycle arrest observed when combining PBR06 and both low (+) and high (++) dose C225 in DiFi cells, we found elevated levels of cleaved caspase 3, indicative of mitochondrial apoptosis. Importantly, we found that similar or higher levels of cleaved caspase 3 could be achieved with combination low-dose C225 and PBR06 compared to the highest dose of C225 alone (++). These data suggest that combining a TSPO ligand with C225 in a WT KRAS CRC cell line results in an approximately 10-fold enhancement in the efficacy of C225.

See FIG. 24 (a).

Example 11

This Examples shows that a TSPO ligand of the present invention enhances C225 efficacy in a mutant KRAS CRC cell line.

Here, the present inventors illustrate that that combining a TSPO ligand with C225 results in cell cycle arrest and apoptosis unobtainable with either agent alone. (PBR06 concentrations=0, 10 nm+, 100 nM++, 1 μM+++, 10 uM++++; C225 concentrations=0.511 g/mL+, 5.0 μg/mL++, 25 μg/mL+++). In these studies, HCT116 p53−/− human CRC cells were exposed to drug for 24 h, harvested, and the protein levels of various markers were assayed by immunoblotting. In single agent dose escalation studies we found that increasing concentrations of PBR06 induced modestly elevated levels of pERK. No concentrations of C225 were found to inhibit pERK, induce p27, or caspase 3 cleavage in this model. However, in combination, we found that pERK could be fully inhibited at elevated concentrations of C225 with PBR06. Importantly, even at the lowest concentration of C225, combination with PBR06 at all concentrations resulted in elevated p27, indicating cell cycle arrest. Furthermore, at all but the lowest concentration of PBR06, significant levels of cleaved caspase 3 were induced, indicating substantial apoptosis. These data suggest that combining a TSPO ligand with e225 in a mutant KRAS CRC cell line results C225 efficacy.

Figure 24A:
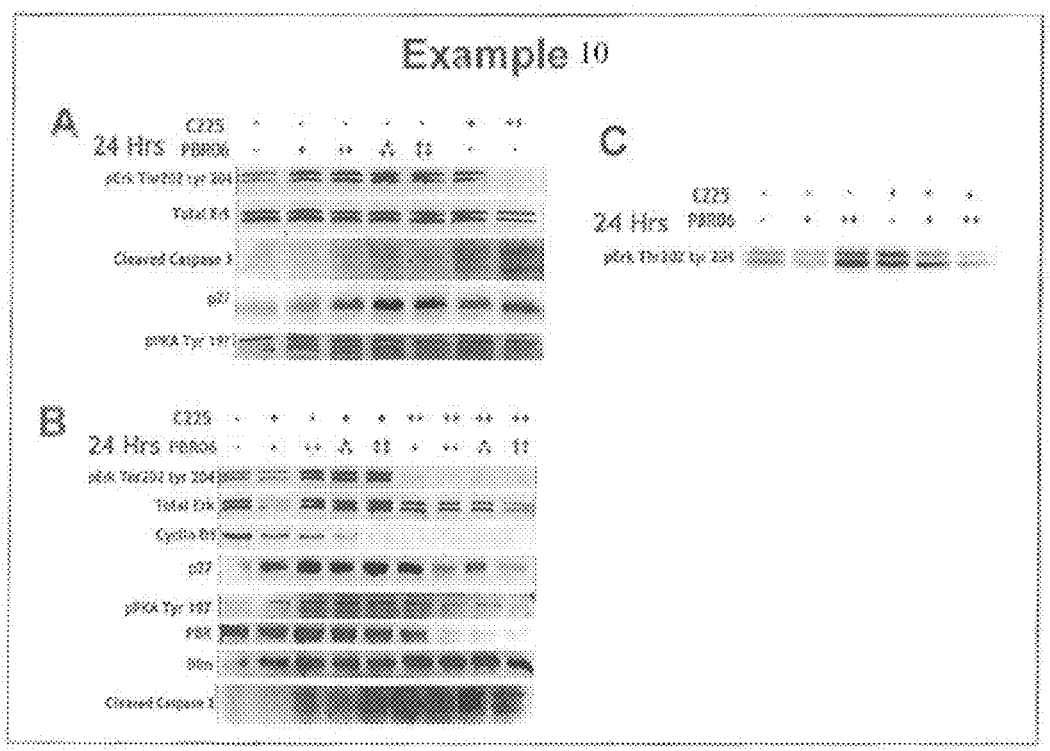
FIG. 24 (a)-(c) is data that show TSPO compounds of the present invention enhance C225 efficacy in a (a) WT KRAS CRC cell line, (b) mutant KRAS CRC cell line, and (c) a mutant B-RAF CRC cell line.
Figure 24B:
Figure 24B:
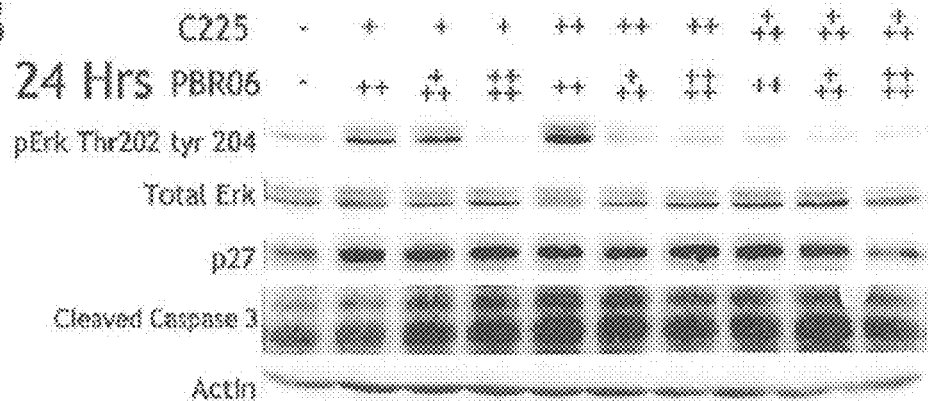

See FIG. 24(b).

Example 12

This example shows TSPO ligand-dependent C225 efficacy in a mutant B-RAF CRC cell line.

Here, the present inventors show that combining a TSPO ligand with C225 results in cell cycle arrest unobtainable with either agent alone. (PBR06 concentrations=0, 10 nm+, 100 nM++, 1 μM+++, 10 μM++++; C225 concentrations=0.5 μg/mL+, 5.0 μg/mL++, 25 μg/mL+++). In these studies, LIM 2405 human CRC cells were exposed to drug for 24 h, harvested, and the protein levels of various markers were assayed by immunoblotting. In single agent dose escalation studies we found that increasing concentrations of PBR06 resulted in elevated levels of pERK, but C225 had little or no effect. At the highest dosage of C225 (+++), we noted some induction of p21 by C225. In combination with C225, PBR06 resulted in significant induction of p21 at even the lowest dosages of C225 tested. These data suggest that combining a TSPO ligand with C225 in a mutant B-RAF CRC cell line results C225 efficacy.

Figure 24C:
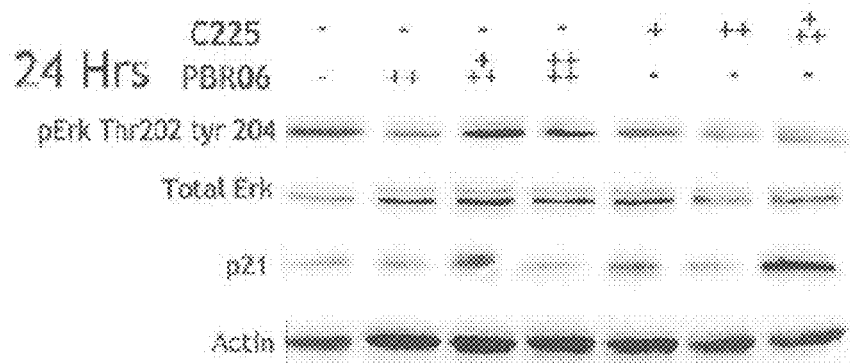
Figure 24C:
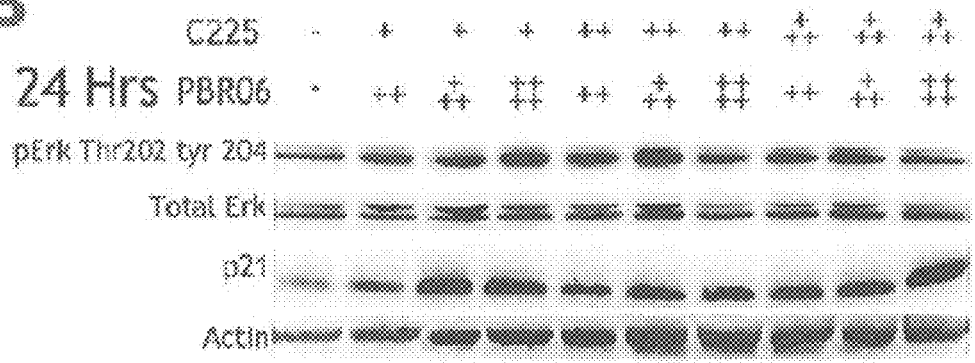

See FIG. 24(c).

Example 13

This Example shows TSPO-PET imaging in a novel mouse model of CRC with compounds of the present invention.

The Lrig1-CreERT2;Apcfl/+mouse model of colorectal cancer (CRC) has been described. Tumors arising in the Lrig1-CreERT2;Apcfl/+mouse exhibit similar characteristics to human CRC tumors, including up-regulation of translocator protein (TSPO) and Wnt signaling early after tumorigenesis. Tumors in the Lrig1-CreERT2;Apcfl/+mouse were detected using TSPO-targeted PET imaging with an embodiment of the present invention, 18F-VUIIS1008. In wild type mice low 18F-VUIIS1008 uptake was observed in the mouse colon.

Methods:

Mouse Model

All studies were conducted in accordance with federal and institutional guidelines. Lrig1-CreERT2/+mice (35) were crossed to Apcfl/+mice to generate Lrig1-CreERT2/+; Apcfl/+mice. Six to eight week old mice were injected with 2 mg tamoxifen (Sigma Aldrich) intraperitoneally for three consecutive days to induce tumor formation. Mice were imaged approximately 100 days after injection of tamoxifen and then sacrificed Colonoscopy Colonoscopy (KARL STORZ-SCB Endoscope System) was performed monthly beginning two months after tamoxifen induction. Mice are anesthetized and immobilized using 2% isofluorane anesthesia in 100% oxygen at 2 L/min. Tumor formation within a single mouse was tracked over time. Upon visual detection of distal colon tumors mice were designated for PET imaging.

PET Imaging

PET imaging was performed using a dedicated small animal PET scanner (Concorde Microsystems Focus 220) as described. Briefly, mice were maintained under 2% isofluorane anesthesia in 100% oxygen at 2 L/min and kept warm via a circulating water heating pad during the PET scan. Animals were administered 7.4-9.3 MBq of [$^{18}$F]-VUIIS1008 intravenously and allowed free access to food and water during a 50 minute uptake period and a 20 minute PET acquisition. Scans were reconstructed using OSEM3D/MAP. The resulting three-dimensional reconstructions had a voxel size of 0.474 mm in the x-y plane and 0.796 mm inter-slice and were visualized using ASIPro software (Siemens).

Tissue Microarray

After institutional review board approval, 99 primary colorectal cancer and normal colonic mucosa tissue samples were collected from patients treated at Vanderbilt University Medical Center. Samples were histologically verified and representative regions were selected in inclusion in the TMA. Each tumor was sampled in duplicate using 1 mm cores. Each tumor sample, for each biomarker were scored in triplicate on an ordinal intensity scale ranging from 0 (no expression) to 3. The average score for each biomarker was calculated and a patient was considered "high expressing" for the biomarker if the average score was greater than 1.34. Since and individual sample was considered positive if the score was greater than 1, a score of 1.33 occurs among 3 samples for a pair of 1's and a single 2 (4/3=1.33).

Immunohistochemistry

Excised colon tumors from the Lrig1-CreERT2;Apcfl/+ mice were fixed in 10% formalin for 24 h and transferred to 70% ethanol. Both the mouse tumors and the human CRC TMAS were blocked in paraffin and sectioned prior to immunostaining for TSPO and B-catenin. Tissues were evaluated by an GI pathologist.

Results

Distal Colon Tumors in Lrig1-CreERT2;Apcfl/+Mice Express High Levels of Tspo and β-Catenin Lrig1-CreERT2;Apcfl/+mice were sacrificed approximately 100 days following induction of colorectal tumors via tomoxifen injection. At approximately 100 days, tumors were easily visualized on serial colonoscopy. Tumors presented as large polyps arising from the normal lumen (FIG. 25A). Upon sacrifice, gross examination of the colon reveals multiple large tumors in the distal colon, however few, if any, tumors in other parts of the large intestine (FIG. 25B). Histological evaluation of fixed colons revealed robust Tspo (FIG. 25C) and 3-catenin (FIG. 25D) in the tumor polyp, while relatively low expression of both markers in areas of normal colon. Tspo and β-catenin showed similar localization in the tumor polyps, showing greater staining intensity in regions of low differentiation.

18F-VUIIS-1008 Uptake is Greater in the Distal Colon of Lrig1-CreERT2;Apcfl/+ than in Wild Type Mice To assess the ability of 18F-VUIIS1008 PET to detect colon tumors, Lrig1-CreERT2;Apcfl/+ with known tumors were imaged along with wild type control mice. Wild type mice imaged with 18F-VUIIS1008 demonstrated low tracer uptake in the colon (FIG. 26A), however high uptake was observed in the lungs consistent with *** as well as the liver and kidneys corresponding to clearance of the tracer. Lrig1-CreERT2;Apcfl/+mice with colonoscopy confirmed tumors demonstrated increased, focal uptake in the distal colon compared to adjacent non-tumor tissue and wild type controls (FIG. 26B/C). Similar uptake in the lungs, liver, and kidneys was observed in the Lrig1-CreERT2;Apcfl/+mice compared to the wild type mice.

Expression of TSPO and β-Catenin in Human Colorectal Tumors

Figure 27:
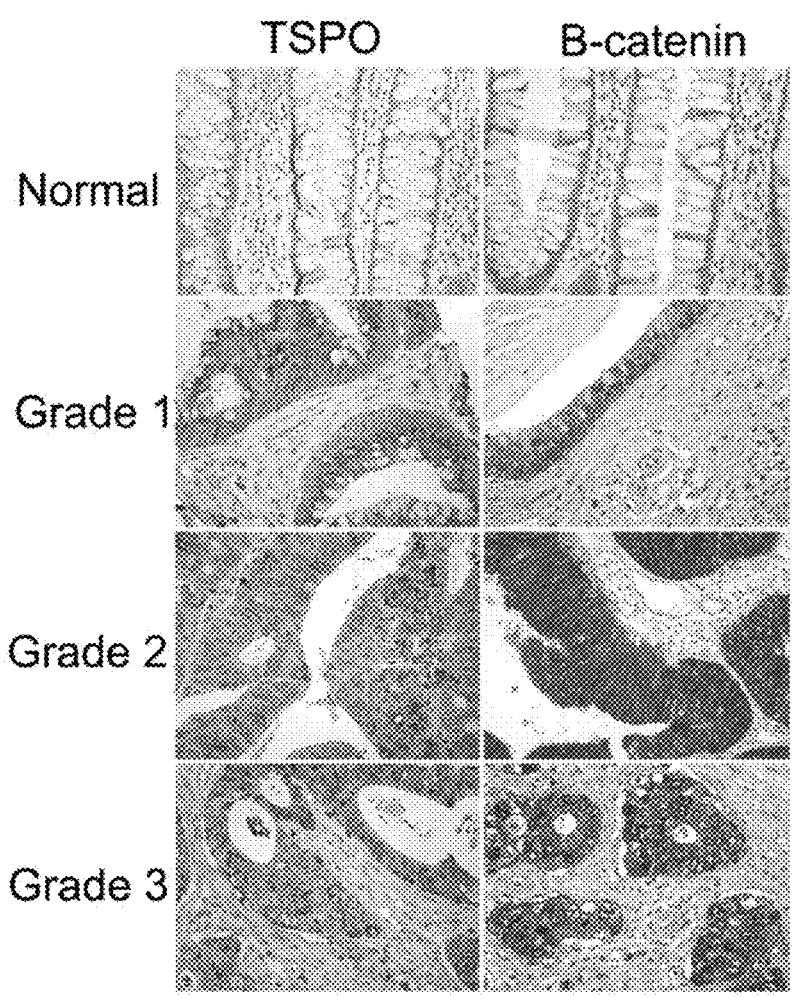
FIG. 27 shows TSPO and B-catenin are increased in CRC compared to normal tissue. Low levels of both TSPO and B-catenin expression are observed in normal colon tissue. Grade 1, grade 2, and grade 3 CRCs demonstrate increased TSPO and B-catenin expression.

To assess the potential utility of TSPO-targeted imaging in a clinical setting, TSPO and β-catenin protein expression were evaluated in human colorectal tumors. Low TSPO and β-catenin expression were observed in non-tumor colon tissue, similar to that in the Lrig1-CreERT2;Apcfl/+mouse model (FIG. 27). TSPO and β-catenin expression were greatly increased in grade 1, 2 and 3 tumors compared to normal tissue, and showed similar morphology to tumors arising in the Lrig1-CreERT2;Apcfl/+mouse model (FIG. 27). Across 84 tumors, high TSPO expression was noted in 54 (64.29%) tumors including 9/11 (81.82%) of grade 1 tumors (see the table, below). In contrast, the widely used marker of proliferation, Ki67, showed high expression in 43/89 (48.31%) tumors, and only 4/12 (33.33%) of grade 1 tumors showed high expression.

TABLE

Distribution of TSPO and Ki67 expression levels in human CRC.

| Marker | Grade | Low | High | Total |
|---|---|---|---|---|
| TSPO | 1 | 2 (18.18%) | 9 (81.82%) | 11 |
|  | 2 | 24 (43.64%) | 31 (56.36%) | 55 |
|  | 3 | 4 (22.22%) | 14 (77.78%) | 18 |
| Total: |  | 30 | 54 | 84 |
| Ki67 | 1 | 8 (66.67%) | 4 (33.33%) | 12 |
|  | 2 | 28 (50%) | 28 (50%) | 56 |
|  | 3 | 10 (47.62%) | 11 (52.38%) | 21 |
| Total: |  | 46 | 43 | 89 |

Figure 25:
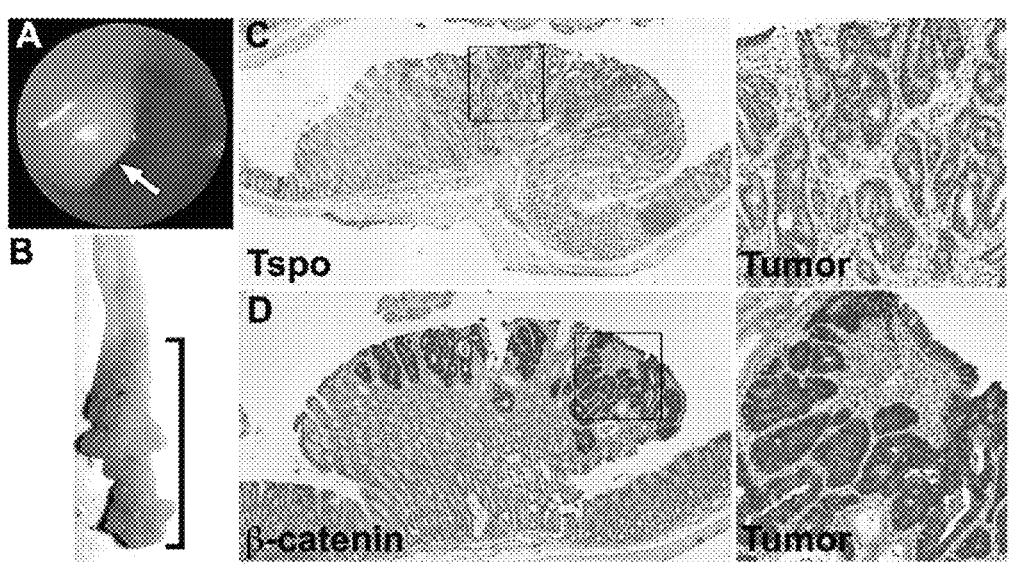
FIG. 25 shows TSPO and β-catenin are expressed at high levels in tumors arising in Lrig1-CreERT2;Apcfl/+ mice. At approximately 100 days following tomxifen injection, large tumors are detected by colonoscopy (A) and are observed throughout the distal colon (B). Elevated TSPO expression is observed in the tumor compared to normal tissues (B). Similarly, β-catenin expression is increased in the tumor than adjacent normal tissue. Histological evaluation of fixed colons revealed robust Tspo (C) and β-catenin (D) in the tumor polyp, while relatively low expression of both markers in areas of normal colon. Tspo and β-catenin showed similar localization in the tumor polyps, showing greater staining intensity in regions of low differentiation.
Figure 26:
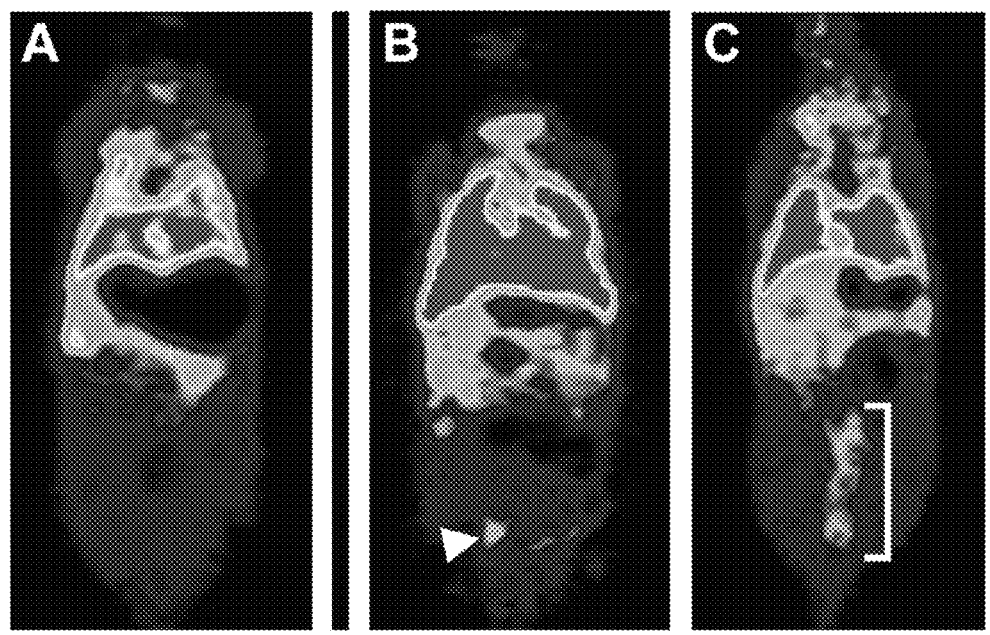
FIG. 26 shows 18F-VUIIS1008 can detect tumors in the distal colon in Lrig1-CreERT2;Apcfl/+ mice. Wld type control mice show little 18F-VUIIS1008 uptake in the distal colon (A). 18F-VUIIS PET can visualize lesions in the distal colon arising in Lrig1-CreERT2;Apcfl/+ mice (B,C).

The present inventors tested the ability of TSPO-targeted PET to detect colon tumors arising in the genetically engineered Lrig1-CreERT2;Apcfl/+mouse. The Lrig1-CreERT2; Apcfl/+mouse provides a clinically relevant mouse model of CRC that develops large lesions in the distal colon. Tumors arising in the Lrig1-CreERT2;Apcfl/+mouse at 100 days following tomoxifen induction express high levels of TSPO compared to non-tumor colon tissue (FIG. 25). PET imaging with 18F-VUIIS1008 demonstrated uptake in the colons of Lrig1-CreERT2;Apcfl/+mice consistent with the known presence of tumors in the distal colon while low uptake was observed in wild type mice (FIG. 26).

In human CRC tumors, TSPO expression was higher for all tumor grades compared to normal colon tissue. Morphologically, TSPO staining was similar between human tumors and tumors in the Lrig1-CreERT2;Apcfl/+mouse model. Additionally, B-catenin staining was increased similarly to TSPO staining in all tumor grades compared to normal colon, and the Lrig1-CreERT2;Apcfl/+model was morphologically similar to human tissues. Taken together, the Lrig1-CreERT2;Apcfl/+mouse model appears to be a faithful representation of human disease.

As high TSPO expression has been observed in a number of cancer types (REFS) as well as poorer prognosis, TSPO is an attractive imaging biomarker. In our analysis of human colorectal cancers as well as the Lrig1-CreERT2;Apcfl/+ mouse, TSPO expression is increased in concordance with β-catenin in all tumor grades, suggesting that TSPO may potentially be a marker of WNT signaling. Indeed, increased TSPO gene expression has been observed in concordance with up-regulation of Wnt in breast cancer, however additional studies will be needed to confirm this association. Additionally, increased TSPO expression is observed in low grade tumors compared to the gold standard clinical marker of proliferation, Ki67. These results suggest that TSPO-PET may be useful in detection of early tumors, which are currently difficult to detect using current clinical standards.

The Lrig1-CreERT2;Apcfl/+mouse model features a tumor microenvironment more similar to human CRC than many of the commonly utilized mouse models. TSPO-PET imaging represents an opportunity to assess disease progression, and possibly treatment response, in preclinical trials. This study demonstrates that imaging colon tumors with 18F-VUIIS1008 PET is feasible and is potentially clinically important.

Example 14

This Example shows TSPO ligand-dependent C225 efficacy in mouse models of pancreatic cancer.

Figure 28:
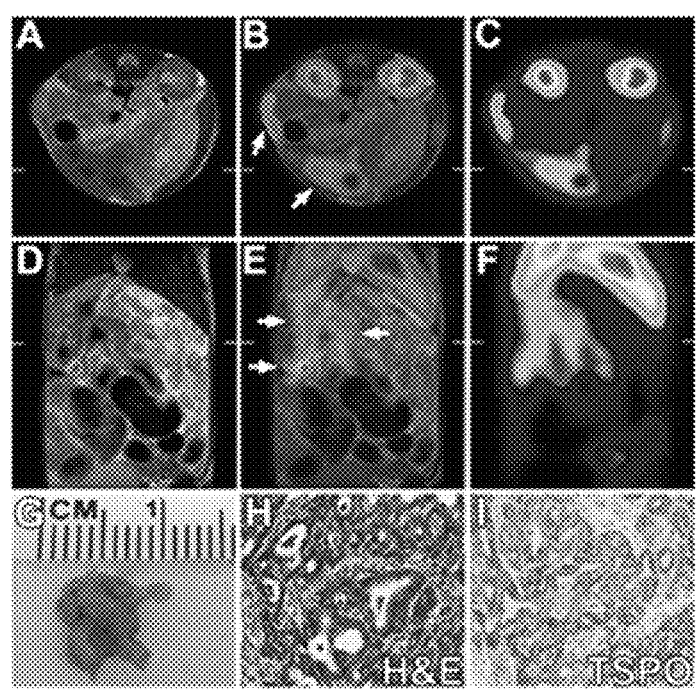
FIG. 28 shows in vivo PET imaging with $^{18}$F-VU11S-1018 visualizes a pancreatic cancer in Ptf1a$^{cre/+}$;LSL-Kras$^{G12D}$;Tgfbr2$^{fl/fl}$ mouse. High-field MRI (A), MRI/PET fusions (B) and PET image (C), transverse view shown. Arrows denote tumor visualized in this imaging slice. Kidneys (top of image) and spleen (lower right) are also visible. Coronal views (MRI, (D): MRI/PET fusion, (E): and PET, (F) show tumor uptake (arrows) and accumulation in the liver. Immediately following imaging, mice were sacrificed and the tumors resected. Excellent agreement was also observed when comparing tracer accumulation, gross tumor morphology (G), and histology (H and I).

The present inventors have carried out PET imaging of six-week old Ptf1a$^{cre/+}$;LSL-Kras$^{G12D}$;Tgfbr2$^{fl/fl}$ mice using a compound of the present invention, $^{18}$F-VUIIS-1018. In tumor-bearing animals, three-dimensional dynamic PET data were registered with high-field (9.4 T) MRI data, enabling correlations between tracer accumulation and anatomy. The resulting PET images shown are summed 90-minute dynamic acquisitions. As expected from previous experience with this tracer in mice, accumulation of $^{18}$F-VUIIS-1018 was observed in kidney and liver (FIG. 28), as well as minor uptake in myocardium (not shown) and spleen. Importantly, intense, focal uptake of $^{18}$F-VUIIS-1018 was also observed in tumor tissue (FIG. 28B, arrows on transverse view; FIG. 28E, arrows on coronal view) that by far exceeded uptake in surrounding normal tissues, including small bowel and spleen. Quantification of tracer uptake revealed the percentage of the injected dose per gram of tissue (% ID/g) was approximately 11% for tumor tissue and 3% for adjacent small bowel, which resulted in excellent imaging contrast between tumor and surrounding normal tissue (>3:1). Immediately following imaging, mice were sacrificed and the tumors resected. Excellent agreement was also observed when comparing tracer accumulation, gross tumor morphology (FIG. 28G), and histology (FIGS. 28H and 28I).

Example 15

This Example demonstrates that embodiments of the present invention are useful as TSPO PET probes for glioma imaging.

VUIIS1008, has a sub-nanomolar binding affinity against [$^3$H]PK11195, demonstrating a 30 fold higher binding affinity compared with DPA-714 and PBR06 in C6 cell lysate.

Before PET imaging with $^{18}$F-VUIIS1008, brain tumors were localized with T2-weighted MRI. Similar to pervious observations, the C6 tumors exhibited marked hyperintensity indicative of longer T2 relaxation times, compared with the surrounding healthy brain. Dynamic PET of $^{18}$F-VUIIS1008 illustrated most of the uptake in the brain was localized to the tumor, with only modest accumulation in the adjacent, normal brain. Similar to the imaging of $^{18}$F-DPA-714, accumulation of $^{18}$F-VUIIS1008 was observed in the olfactory epithelium, harderian glands and tongue, where TSPO has a high expression. After the initial spike in radioactivity consistent with tracer injection, $^{18}$F-VUIIS1008 rapidly cleared from the plasma. Imaging-matched brains were processed for staining and immunohistochemistry. Using standard hematoxylin and eosin staining to localize the tumor, the present inventors discovered that TSPO expression was significant higher in tumor than in the adjacent healthy brain. Overall, the present inventors discovered that $^{18}$F-VUIIS 1008 demonstrated a specific uptake of the tracer in tumor, mirroring TSPO expression in tumor and normal tissues and constructing an excellent agreement between $^{18}$F-VUIIS1008 accumulation and TSPO expression levels in the tumor and brain.

Compared with $^{18}$F-DPA714, $^{18}$F-VUIIS1008 exhibited a similar clearance and accumulation in brain, while a faster clearance and a slower accumulation in tumor, indicating a novel in vivo performance in glioma-bearing rats.

In order to fully characterize TSPO expression profile in the healthy tissues and C6 cells, this example includes subcellular studies. The present inventors separated two fractions of tissue and C6 cell lysates based on the density difference. Of these two fractions, the light one mainly contains mitochondria, while the heavy one mainly contains nuclei according to the electron microscope images (Supplemental Data). Based on these two fractions, we performed western blot to determine TSPO expression profile in a variety of healthy tissues and C6 cell lysates. Interestingly, in this study, we found a dominate expression of TSPO in the heavy fraction instead of the light one in C6 cell and kidney lysate. This is different from other healthy tissues such as heart, brain, lung and liver, in which TSPO is expressed mainly in the light fraction instead of the heavy one. Different localization of TSPO turns to have a specific function for the tumor cell growth, which is indicated in previously published results (Reference). Based on this difference, we envision that probes that can bind to the heavy fraction TSPO will bind to the tumor specifically. Thus, we evaluated the binding potential of VUIIS1008 in different fractions. With the compartmental binding assay, the present inventors discovered a comparable high binding affinity of VUIIS1008 in both two fractions (see the table, below), demonstrating a high tumor binding specificity. This is different from PBR06, another TSPO ligand featuring a different scaffold with VUIIS1008, turns to bind to the light fraction selectively with a high binding affinity (Table).

In vivo PET imaging performed with 18F-VUIIS1008 demonstrated a specific uptake of the tracer in tumor, clearly mirroring TSPO expression in tumor and normal tissues. Compared with $^{18}$F-PBR06 and $^{18}$F-DPA714, this tracer exhibited a similar clearance and accumulation in brain, while a faster clearance and a slower accumulation in tumor, indicating a novel in vivo performance in glioma-bearing rats. Meanwhile, this probe also demonstrates a faster uptake compared with 18F-DPA-714, which is demonstrated by the low radioactivity of the plasma in the dynamic scan after the injection. HPLC radiometabolite assay with the plasma extraction also demonstrates a high stability of this probe in the 90 min dynamic PET scan. In order to fully evaluate the novel performance of $^{18}$F-VUIIS1008, we have also determined $^{18}$F-VUIIS 1008 pharmacodynamics with arterial input function. As shown below, the present inventors checked three different models and found that the 4-tissue-6-parameter model is suitable to depict the VUIIS1008 performance based on the goodness-of-fit. Compared with DPA-714, VUIIS1008 has another new compartment detected which features a near-zero K6 in the tumor instead of brain, indicating a strong tumor binding irreversibility.

Mean ± SE compartmental transfer rates for rats with C6 brain glioma injected with [18F]VUIIS1008 and imaged in a microPET for 90 min.

| Compartment Model | Region | $K_1$ (mL/g/min) | $k_2$ (min$^{-1}$) | $k_3$ (min$^{-1}$) | $k_4$ (min$^{-1}$) | $k_5$ (min$^{-1}$) | $k_6$ (min$^{-1}$) | $V_T^\dagger$ (calculated) | $\chi^{2\ddagger}$ |
|---|---|---|---|---|---|---|---|---|---|
| 1-tissue | Tumor | 0.3535 ± 0.1086 | 0.0964 ± 0.0187 | | NA | | | 3.6 ± 0.6 | 55.6 |
| | Brain | 0.3161 ± 0.1124 | 0.3048 ± 0.1350 | | | | | 1.3 ± 0.2 | 53 |

Mean ± SE compartmental transfer rates for rats with C6 brain glioma injected with [18F]VUIIS1008 and imaged in a microPET for 90 min.

| Compartment Model | Region | $K_1$ (mL/g/min) | $k_2$ (min$^{-1}$) | $k_3$ (min$^{-1}$) | $k_4$ (min$^{-1}$) | $k_5$ (min$^{-1}$) | $k_6$ (min$^{-1}$) | $V_T$† (calculated) | $\chi^2$‡ |
|---|---|---|---|---|---|---|---|---|---|
| 2-tissue | Tumor | 0.5448 ± 0.1120 | 1.2413 ± 0.8028 | 0.1300 ± 0.0587 | 0.0234 ± 0.0046 | NA | | 4.6 ± 0.8 | 10.3 |
| | Brain | 0.5856 ± 0.2171 | 2.0217 ± 1.2077 | 0.2903 ± 0.1801 | 0.0912 ± 0.0407 | | | 1.7 ± 0.4 | 22.8 |
| 3-tissue | Tumor | 0.6449 ± 0.2034 | 2.9459 ± 1.5810 | 0.4597 ± 0.3151 | 0.1371 ± 0.0831 | 0.2304 ± 0.1073 | 0.0574 ± 0.0252 | 6.4 ± 1.8 | 10.5 |
| | Brain | 0.6925 ± 0.2052 | 3.7619 ± 1.3831 | 0.8194 ± 0.6241 | 0.2569 ± 0.1888 | 0.5314 ± 0.1953 | 0.1748 ± 0.0789 | 1.4 ± 0.2 | 21.6 |

†$V_T$ (total distribution volume) was calculated as $K_1/k_2$, $K_1/k_2(1 + k_3/k_4)$, and $K_1/k_2(1 + k_3/k_4 + k_3/k_4)$ for the plasma plus one-, two-, and three-tissue compartment model, respectively.
‡$\chi^2$: goodness of fit, the lower the number is the better fit was achieved.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

Unless otherwise indicated, all numbers expressing quantities of ingredients, properties such as reaction conditions, and so forth used herein are to be understood as being modified in all instances by the term "about."

Accordingly, unless indicated to the contrary, the numerical parameters set forth in the herein are approximations that may vary depending upon the desired properties sought to be determined by the present invention.

All publications cited herein are expressly incorporated herein by reference in their entirety.

We claim:

1. A compound of the following formula:

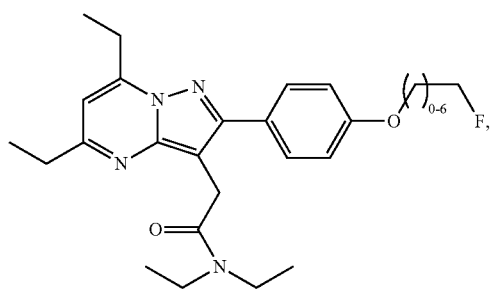

or a pharmaceutically acceptable salt thereof.

2. A compound of the following formula:

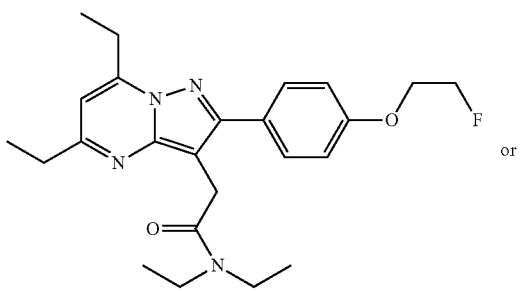

or

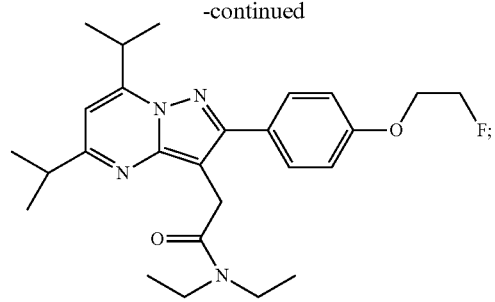

or a pharmaceutically acceptable salt thereof.

3. A pharmaceutical composition comprising a compound of claim 1, or a pharmaceutically acceptable salt thereof and a pharmaceutically acceptable carrier.

4. A pharmaceutical composition comprising a compound of claim 2, or a pharmaceutically acceptable salt thereof, and a pharmaceutically acceptable carrier.

5. A method of imaging a molecular event in a sample, comprising:
(a) administering a probe with an affinity for a target, the probe being selected from a compound of the following formula:

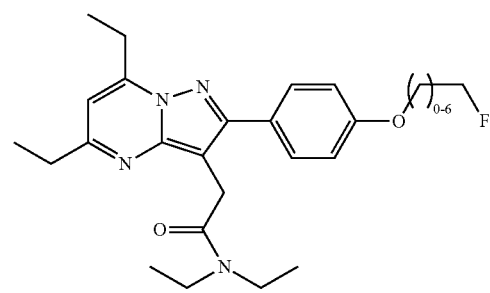

or a pharmaceutically acceptable salt thereof; and
(b) detecting a signal from said probe.

6. The method of claim 5, wherein the sample is at least one of cells, tissue, cellular tissue, serum, cell extract, bodily fluids.

7. The method of claim 5, wherein the administering step is in vivo or in vitro.

8. The method of claim 5, wherein the detecting step is with PET imaging.

9. The method of claim 5, wherein the molecular event is cell proliferation.

10. The method of claim 5, further comprising the step of analyzing said signal to diagnose a disease state.

11. The method of claim 10, further comprising the steps of administering a second probe, detecting a second signal, and comparing a first signal with the second signal to determine the progress of a disease state.

12. The method of claim 11, wherein a treatment step for said disease state occurs between administering steps.

13. The compound of claim 1, wherein the fluorine atom is $^{18}$F.

14. The compound of claim 2, wherein the fluorine atom is $^{18}$F.

15. The compound of claim 3, wherein the fluorine atom is $^{18}$F.

16. The compound of claim 4, wherein the fluorine atom is $^{18}$F.

17. The method of claim 5, wherein the fluorine atom is $^{18}$F.

\* \* \* \* \*

UNITED STATES PATENT AND TRADEMARK OFFICE
CERTIFICATE OF CORRECTION

PATENT NO. : 9,458,161 B1  
APPLICATION NO. : 13/669437  
DATED : October 4, 2016  
INVENTOR(S) : Manning et al.

Page 1 of 1

It is certified that error appears in the above-identified patent and that said Letters Patent is hereby corrected as shown below:

On the Title Page

Item (73), Assignee  
"Vanderblit University" should be --Vanderbilt University--

Signed and Sealed this  
Thirty-first Day of January, 2017

Michelle K. Lee  
*Director of the United States Patent and Trademark Office*